(12) United States Patent
DeSimone et al.

(10) Patent No.: US 9,381,158 B2
(45) Date of Patent: *Jul. 5, 2016

(54) NANOPARTICLE FABRICATION METHODS, SYSTEMS, AND MATERIALS FOR FABRICATING ARTIFICIAL RED BLOOD CELLS

(71) Applicant: The University of North Carolina at Chapel Hill, Chapel Hill, NC (US)

(72) Inventors: Joseph M. DeSimone, Chapel Hill, NC (US); Edward T. Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 375 days.

This patent is subject to a terminal disclaimer.

(21) Appl. No.: 13/904,517

(22) Filed: May 29, 2013

(65) Prior Publication Data

US 2013/0336884 A1    Dec. 19, 2013

Related U.S. Application Data

(63) Continuation of application No. 12/374,182, filed as application No. PCT/US2007/016935 on Jul. 27, 2007, now Pat. No. 8,465,775.

(60) Provisional application No. 60/833,736, filed on Jul. 27, 2006.

(51) Int. Cl.
*A61K 9/14* (2006.01)
*A61K 9/16* (2006.01)
(Continued)

(52) U.S. Cl.
CPC .............. *A61K 9/1641* (2013.01); *A61K 9/0026* (2013.01); *A61K 9/5146* (2013.01); *A61K 9/5153* (2013.01); *A61K 35/18* (2013.01); *A61K 38/42* (2013.01); *A61K 47/34* (2013.01); *A61K 51/1244* (2013.01); *A61L 27/18* (2013.01);
(Continued)

(58) Field of Classification Search
None
See application file for complete search history.

(56) References Cited

U.S. PATENT DOCUMENTS 4,990,283 A    2/1991    Visca et al.
5,869,103 A    2/1999    Yeh et al.
(Continued)

FOREIGN PATENT DOCUMENTS

JP    57-025911    2/1982
JP    2001-158031 A    6/2001
(Continued)

OTHER PUBLICATIONS

M Nichols. "Factors Affecting Size and Swelling of Poly(ethylene glycol) Hydrogel Microspheres Formed in Aqueous Sodium Sulfate Solutions." Washington University of St. Louis, Jan. 2009, All Theses and Dissertations (ETDs). Paper 485. pages: front page, pp. i-vii and 1-57 (65 total sheets).*
(Continued)

*Primary Examiner* — Isaac Shomer
(74) *Attorney, Agent, or Firm* — Alston & Bird LLP

(57) ABSTRACT

A plurality of artificial red blood cell particles includes each particle of the plurality being substantially monodisperse and each particle having a largest common linear dimension of about 5 μm to about 10 μm. The particles can also have a modulus configured such that a particle of the plurality of particles can pass through a tube having an inner diameter of less than about 3 μm.

13 Claims, 43 Drawing Sheets

(51) Int. Cl.
*A61K 9/51* (2006.01)
*A61K 35/18* (2015.01)
*A61K 38/42* (2006.01)
*A61L 27/18* (2006.01)
*A61K 9/00* (2006.01)
*A61K 47/34* (2006.01)
*A61K 51/12* (2006.01)

(52) U.S. Cl.
CPC ............... *A61K9/16* (2013.01); *A61L 2400/12* (2013.01); *Y10S 514/832* (2013.01); *Y10T 428/2982* (2015.01)

(56) References Cited

U.S. PATENT DOCUMENTS

| | | | |
|---|---|---|---|
| 5,879,326 | A | 3/1999 | Godshall et al. |
| 6,660,151 | B1 | 12/2003 | Lessmollmann et al. |
| 6,669,961 | B2 | 12/2003 | Kim et al. |
| 8,465,775 | B2 * | 6/2013 | DeSimone ........... A61K 9/5146 424/489 |
| 2002/0132007 | A1 * | 9/2002 | Randolph ............ A61K 9/1694 424/486 |
| 2003/0071016 | A1 | 4/2003 | Shih et al. |
| 2004/0096662 | A1 * | 5/2004 | Lanphere ............... A61F 2/0036 428/402 |
| 2005/0201988 | A1 | 9/2005 | Acharya et al. |
| 2006/0127352 | A1 | 6/2006 | Hubbell et al. |

FOREIGN PATENT DOCUMENTS

| | | |
|---|---|---|
| JP | 2005-095733 | 4/2005 |
| KR | 2003-0062492 A | 7/2003 |
| WO | WO 99/34831 A1 | 7/1999 |
| WO | WO 03/092785 A1 | 11/2003 |

OTHER PUBLICATIONS

Bhadra, D., et al., "PEGylated Peptide-Based Bendritic Nanoparticulate Systems for Delivery of Artemether," *Journal of Drug Delivery Science and Technology*, 2005, pp. 65-73, vol. 15(1).

Dictionary Definition for the word "particle." http://www.thefreedictionary.com/p/particie, accessed Aug. 9, 2012, 3 printed pages.

Linderkamp, O., et al., "Geometry of Neonatal and Adult Red Blood Cells," *Pediatric Research*, 1983, pp. 250-253, vol. 17.

Minamitani, H., et al., "Analysis of Elasticity and Deformability of Erythrocytes Using Micro-Channel Flow System and Atomic Force Microscope," *1st International IEEE-EMBS Special Topic Conference on Microtechnologies in Medicine in & Biology*, Poster 43, Oct. 12-14, 2000, pp. 68-71.

Riley, T., et al., Use of Viscoelastic Measurement for Investigating Interparticle Interactions in Dispersions of Micellar-Like Poly(lactic acid)-poly(ethylene glycol) Nanoparticles, *Langmuir*, 2002, pp. 7663-7668, vol. 18.

Thefreedictionary.com. Definition of "artificial". http://www.thefreedictionary.com.com/p/artificial, accessed Mar. 2, 2012, 3 printed pages.

Vauthier, C., et al., "Measurement of the Density of Polymeric Nanoparticulate Drug Carriers by Isopycnic Centrifugation," *Journal of Nanoparticle Research*, 1999, pp. 411-418, vol. 1.

Xin, A., et al., "In vitro Degradation Behavior of Photopolymerized PEG Hydrogels as Tissue Engineering Scaffold," *Proceedings of the 28th IEEE, EMBS Annual International Conference*, Aug. 30-Sep. 3, 2006, pp. 2091-2093.

* cited by examiner

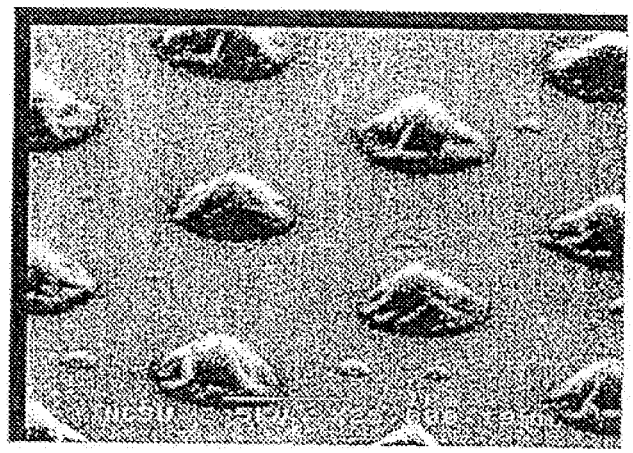
FIGURE 29
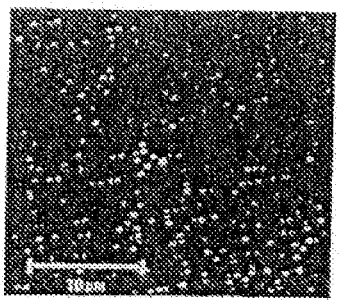 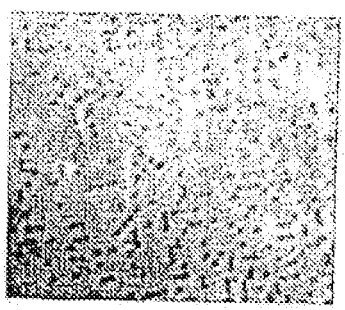 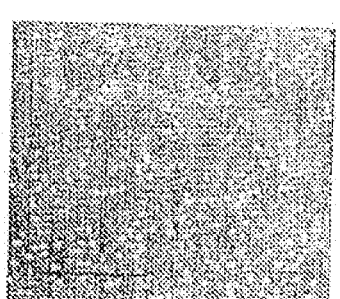
FIGURE 30A   FIGURE 30B   FIGURE 30C

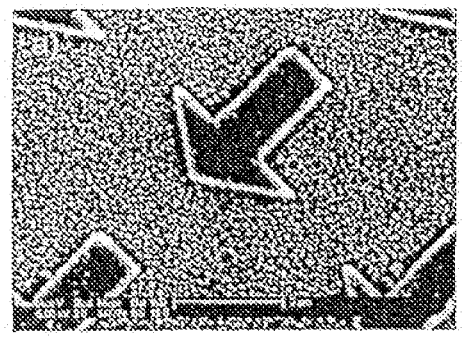
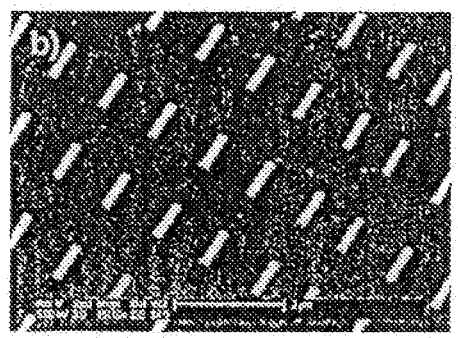
FIGURE 36A          FIGURE 36B
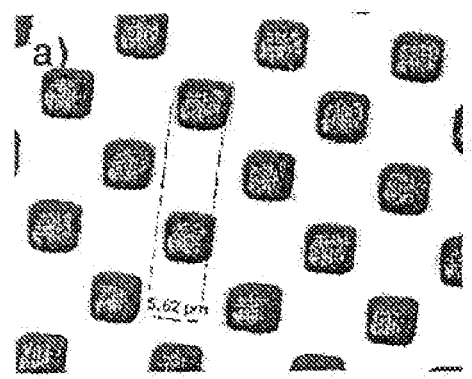
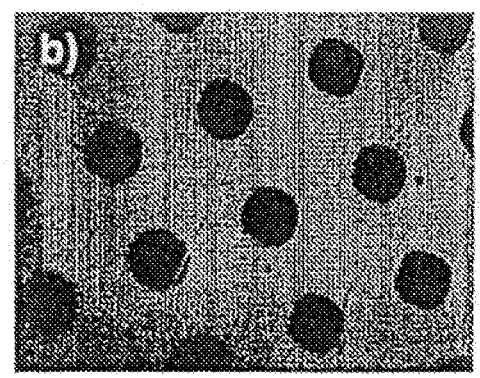
FIGURE 37A          FIGURE 37B

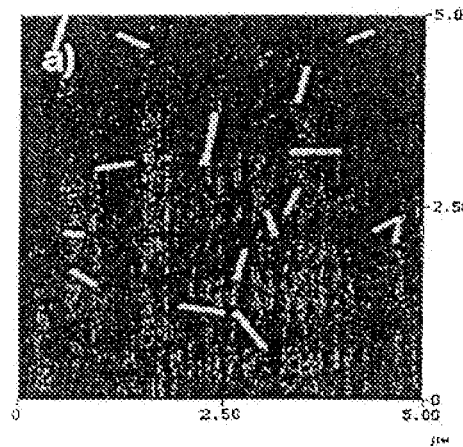 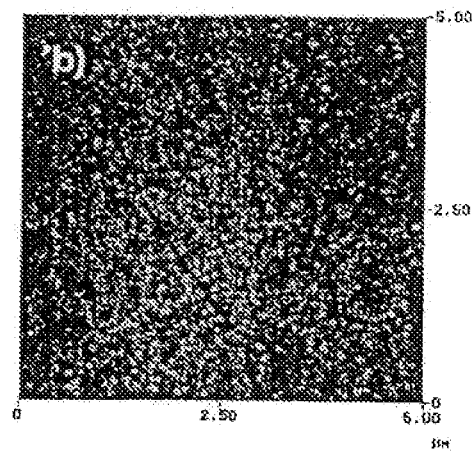
FIGURE 38A          FIGURE 38B
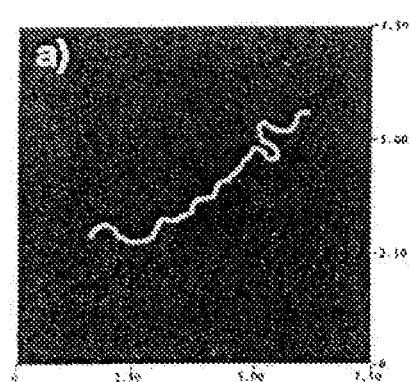 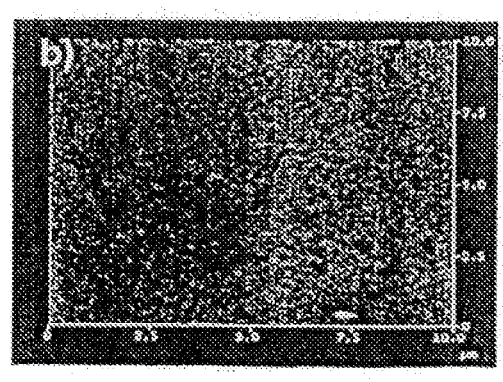
FIGURE 39A          FIGURE 39B CY-3 labeled Avidin attached to the periphery of PRINT particles FITC-biotin FAB attached to PRINT particle through avidin DIC Overlay

NANOPARTICLE FABRICATION METHODS, SYSTEMS, AND MATERIALS FOR FABRICATING ARTIFICIAL RED BLOOD CELLS

CROSS REFERENCE TO RELATED APPLICATIONS

This application is a continuation of U.S. application Ser. No. 12/374,182, filed Oct. 15, 2009, which is a National Phase of International Application No. PCT/US2007/016935, filed Jul. 27, 2007, which claims priority to U.S. Provisional Application No. 60/833,736, filed Jul. 27, 2006, the entire contents of each are incorporated herein by reference.

This application is also a continuation-in-part of PCT International Patent Application Serial NO. PCT/US06/23722, filed Jun. 19, 2006, which is incorporated herein by reference in its entirety.

INCORPORATION BY REFERENCE

All documents referenced herein are hereby incorporated by reference as if set forth in their entirety herein, as well as all references cited therein.

GOVERNMENT INTEREST

This invention was made with U.S. Government support under Grant No. CHE-9876674 awarded by the National Science Foundation and from the Office of Naval Research Grant No. N00014-02-1-0185. The government has certain rights in the invention.

TECHNICAL FIELD

Generally, this invention relates to micro and/or nano scale particle fabrication. More particularly, the micro and/or nano scale particles are fabricated to mimic red blood cells.

ABBREVIATIONS

° C.=degrees Celsius
cm=centimeter.
DBTDA=dibutyltin diacetate
DMA=dimethylacrylate
DMPA=2,2-dimethoxy-2-phenylacetophenone
EIM=2-isocyanatoethyl methacrylate
FEP=fluorinated ethylene propylene
Freon 113=1,1,2-trichlorotrifluoroethane
g=grams
h=hours
Hz=hertz
IL=imprint lithography
kg=kilograms
kHz=kilohertz
kPa=kilopascal
MCP=microcontact printing
MEMS=micro-electro-mechanical system
MHz=megahertz
MIMIC=micro-molding in capillaries
mL=milliliters
mm=millimeters
mmol=millimoles
mN=milli-Newton
m.p.=melting point
mW=milliwatts
NCM=nano-contact molding
NIL=nanoimprint lithography
nm=nanometers
PDMS=polydimethylsiloxane
PEG=poly(ethylene glycol)
PFPE=perfluoropolyether
PLA=poly(lactic acid)
PP=polypropylene
Ppy=poly(pyrrole)
psi=pounds per square inch
PVDF=poly(vinylidene fluoride)
PTFE=polytetrafluoroethylene
SAMIM=solvent-assisted micro-molding
SEM=scanning electron microscopy
S-FIL="step and flash" imprint lithography
Si=silicon
Tg=glass transition temperature
Tm=crystalline melting temperature
TMPTA=trimethylolpropane triacrylate
μm=micrometers
UV=ultraviolet
W=watts

BACKGROUND

Mammalian red blood cells are critical for the delivery of oxygen to body tissues and the exchange of carbon dioxide from body tissues. One critical feature of red blood cells (RBC) is their ability to severely deform in shape to pass through intercellular gaps of sinusoids in the spleen and capillaries. Disorders of red blood cells can enhance rigidification of red blood cells and reduce their ability to pass through intercellular gaps and capillaries. Such rigidification is a key feature of the biology and pathophysiology of malaria (Miller, et al. *Nature* (2002); Cooke, et al. *Adv. Parasitology* (2001); and Glenister, et. al *Blood* (2002); each of which is incorporated herein by reference). Sickle cell anemia is another RBC-based condition which is caused by elongated RBCs. Furthermore, over time RBCs stiffen and aged red blood cells are removed from the body after about 120 days. Therefore, there exists a need to fabricate an artificial RBC which can deform in size to pass through intercellular gaps and capillaries and carry and exchange oxygen with carbon dioxide.

SUMMARY

According to some embodiments, an artificial red blood cell includes a plurality of particles where each particle of the plurality of particles is substantially monodisperse. In some embodiments, each particle has a largest linear dimension of about 5 μm to about 10 μm and a modulus less than about 1 MPa. In some embodiments, a particle of the plurality of particles can pass through a tube having an inner diameter of less than about 3 μm.

According to some embodiments, an artificial red blood cell includes a plurality of substantially monodisperse particles, where each particle has substantially a disc shape. In some embodiments, each particle has a diameter of about 5 μm to about 10 μm. In some embodiments, each particle has a porosity configured to give the particle a modulus such that the particle can pass through a tube having an inner diameter of less than about 3 μm.

According to some embodiments, the particles include poly(ethylene glycol). In some embodiments, the particles include perfluoropolyether.

According to some embodiments, the particles may include surface functionality and/or cargo. In some embodiments, the cargo is capable of binding and releasing oxygen.

In some embodiments, particles are used to obtain sustained and modulated drug delivery. The design and development of such systems, mathematical modeling of transport from these systems and the in vivo use of these devices accumulate to their impact and potential use in a variety of disease states. Measurement of drug distribution in vascular tissue using quantitative fluorescence microscopy of the particles disclosed herein is one such system.

In some embodiments, particles can be fabricated from biocompatible materials with solubility and/or philicity control. The mesh density and charge can be altered to control factors such as modulus and release of cargo. In some embodiments, particles can be designed with stimulated degradation for cargo release. Due to the unique manufacturing method, described in pending PCT application PCT/US06/23722 filed on Jun. 19, 2006 which is incorporated herein by reference in its entirety including all references cited therein, monodisperse particles can be made with shape and size specificity.

According to some embodiments, particles may carry a wide variety of cargos. Particles may incorporate therapeutics, such as small molecules, proteins, oligos, siRNAs, and pDNA, imaging beacons for PET, SPECT, MR, and ultrasound, as well as organelles. In some embodiments, no chemical modification of the cargo is needed. High loadability is also possible.

In some embodiments, particles are amenable to surface functionalization for targeting and enhanced circulation. In some embodiments, ligands on the surface allow for tailored bioavailability and enhanced electrostatic or steric stabilization. Non-spherical particles have a unique ability to increase the number of surface ligands per cargo volume. The particles are also amenable to all dosage forms, including injectables, oral, inhalation, and dermatological.

BRIEF DESCRIPTION OF THE DRAWINGS

Reference is made to the accompanying drawings in which are shown illustrative embodiments of the presently disclosed subject matter, from which its novel features and advantages will be apparent.

FIG. 5A represents an SEM image of red blood cells in a capillary. FIG. 5B represents a schematic diagram of a red blood cell. FIG. 5C represents an image of red blood cells in a 7 μm capillary.

FIG. 10A is a brush polymer master. FIG. 10B is a PFPE-DMA mold templated from a brush polymer master.

FIG. 29 is a scanning electron micrograph of 500-nm conical shaped Ppy particles.

FIGS. 30A-30C are fluorescence confocal micrographs of 200-nm isolated trapezoidal particles of PEG diacrylate that contain fluorescently tagged DNA. FIG. 30A is a fluorescent confocal micrograph of 200 nm trapezoidal PEG nanoparticles which contain 24-mer DNA strands that are tagged with CY-3. FIG. 30B is optical micrograph of the 200-nm isolated trapezoidal particles of PEG diacrylate that contain fluorescently tagged DNA. FIG. 30C is the overlay of the images provided in FIGS. 30A and 30B, showing that every particle contains DNA.

FIGS. 36A and 36B are a scanning electron micrograph of mold fabrication from electron-beam lithographically generated masters. FIG. 36A is a scanning electron micrograph of silicon/silicon oxide masters of 3 micron arrows. FIG. 36B is a scanning electron micrograph of silicon/silicon oxide masters of 200-nm×800-nm bars.

FIGS. 37A and 37B are an optical micrographic Image of mold fabrication from photoresist masters. FIG. 37A is a SU-8 master. FIG. 37B is a PFPE-DMA mold templated from a photolithographic master.

FIGS. 38A and 38B are an atomic force micrograph of mold fabrication from Tobacco Mosaic Virus templates. FIG. 38A is a master. FIG. 38B is a PFPE-DMA mold templated from a virus master.

FIGS. 39A and 39B are an atomic force micrograph of mold fabrication from block copolymer micelle masters. FIG. 39A is a polystyrene-polyisoprene block copolymer micelle. FIG. 39B is a PFPE-DMA mold templated from a micelle master.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Formation of Isolated Micro- and/or Nanoparticles

Figure 1A:
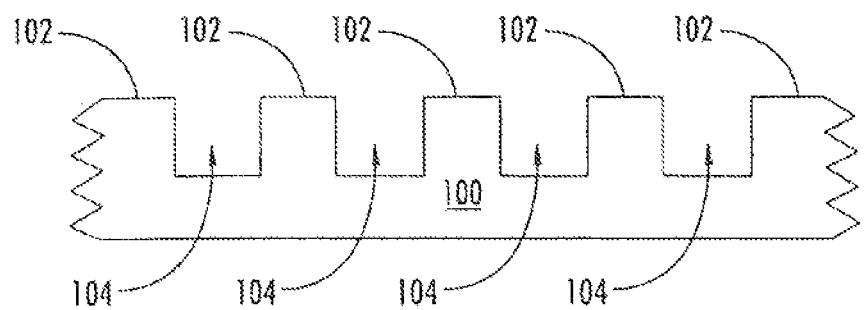
FIGS. 1A-1D are a schematic representation of an embodiment of the presently disclosed method for preparing a patterned template.

In some embodiments, the presently disclosed subject matter provides isolated micro- and/or nanoparticles and methods for making the isolated micro- and/or nanoparticles. In some embodiments, the process for making the isolated micro and/or nanoparticles includes initially forming a patterned substrate. Turning now to FIG. 1A, a patterned master 100 is provided. Patterned master 100 includes a plurality of non-recessed surface areas 102 and a plurality of recesses 104. In some embodiments, patterned master 100 includes an etched substrate, such as a silicon wafer, which is etched in the desired pattern to form patterned master 100.

Figure 1B:
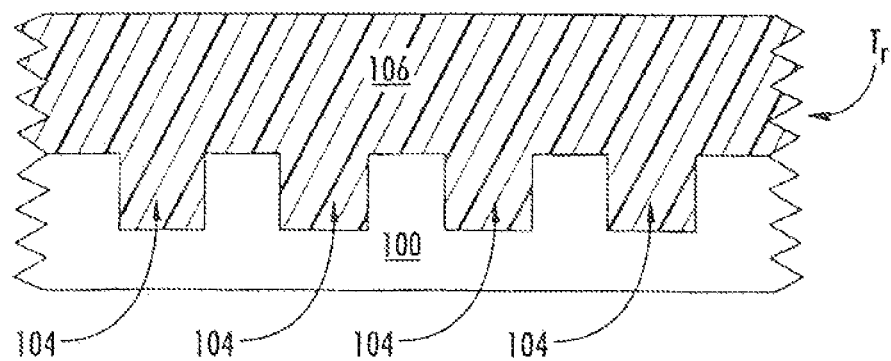

Referring now to FIG. 1B, a liquid material 106, for example, a liquid fluoropolymer composition, such as a PFPE-based precursor, is then poured onto patterned master 100. Liquid material 106 is treated by treating process $T_r$, for example exposure to UV light, actinic radiation, or the like, thereby forming a treated liquid material 108 in the desired pattern.

Figure 1C:
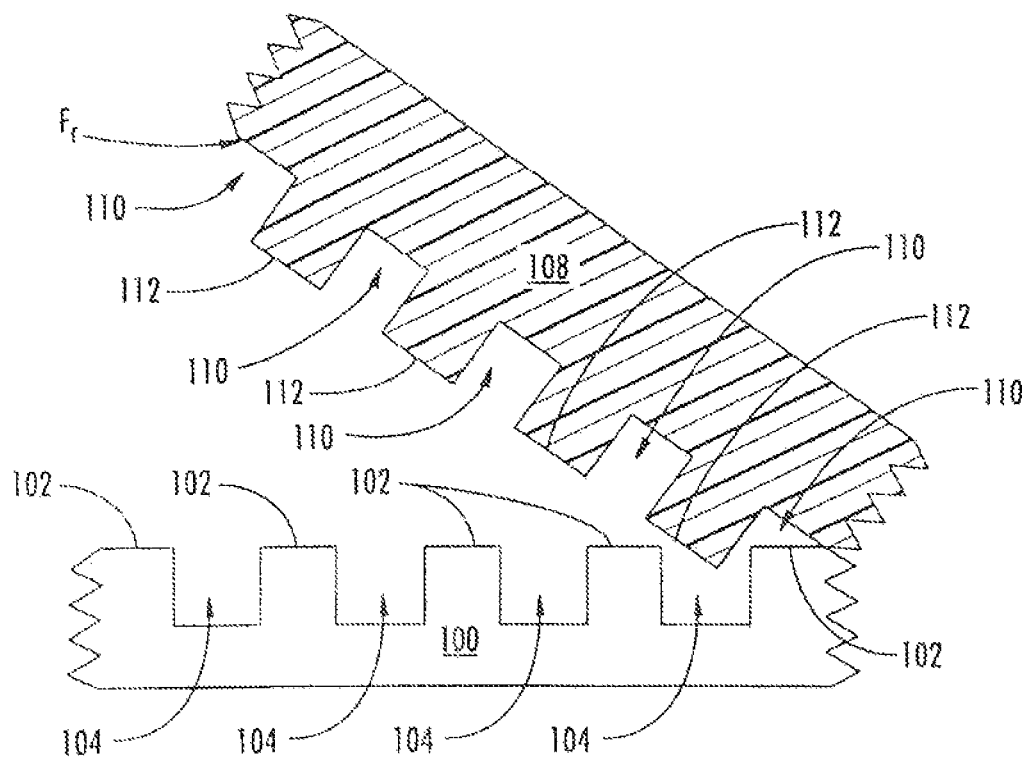
Figure 1D:
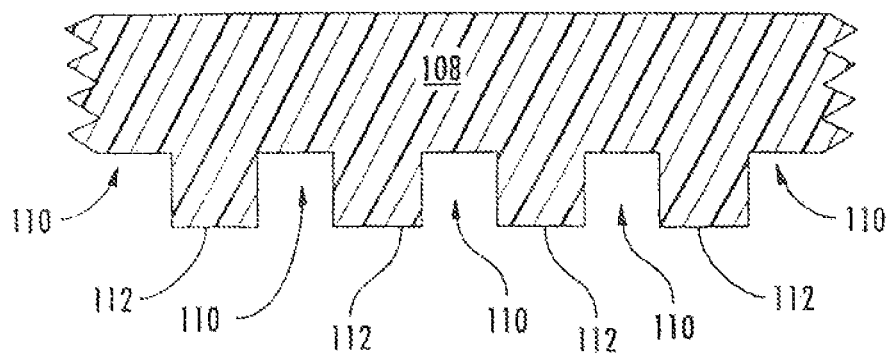

Referring now to FIGS. 1C and 1D, a force Fr is applied to treated liquid material 108 to remove it from patterned master 100. As shown in FIGS. 1C and 1D, treated liquid material 108 includes a plurality of recesses 110, which are mirror images of the plurality of non-recessed surface areas 102 of patterned master 100. Continuing with FIGS. 1C and 1D, treated liquid material 108 includes a plurality of first patterned surface areas 112, which are mirror images of the plurality of recesses 104 of patterned master 100. Treated liquid material 108 can now be used as a patterned template for soft lithography and imprint lithography applications. Accordingly, treated liquid material 108 can be used as a patterned template for the formation of isolated micro- and nanoparticles.

In some embodiments, the patterned template includes a patterned template formed by a replica molding process. In some embodiments, the replica molding process includes: providing a master template; contacting a liquid material with the master template; and curing the liquid material to form a patterned template.

In some embodiments, the master template includes, without limitation, one or more of a template formed from a lithography process, a naturally occurring template, combinations thereof, or the like. In some embodiments, the natural template is selected from one of a biological structure and a self-assembled structure. In some embodiments, the one of a biological structure and a self-assembled structure is selected from the group including a naturally occurring crystal, an enzyme, a virus, a protein, a micelle, and a tissue surface.

In some embodiments, the method includes modifying the patterned template surface by a surface modification step. In some embodiments, the surface modification step is selected from the group including a plasma treatment, a chemical treatment, and an adsorption process. In some embodiments, the adsorption process includes adsorbing molecules selected from the group including a polyelectrolyte, a poly(vinylalcohol), an alkylhalosilane, and a ligand.

Figure 2A:
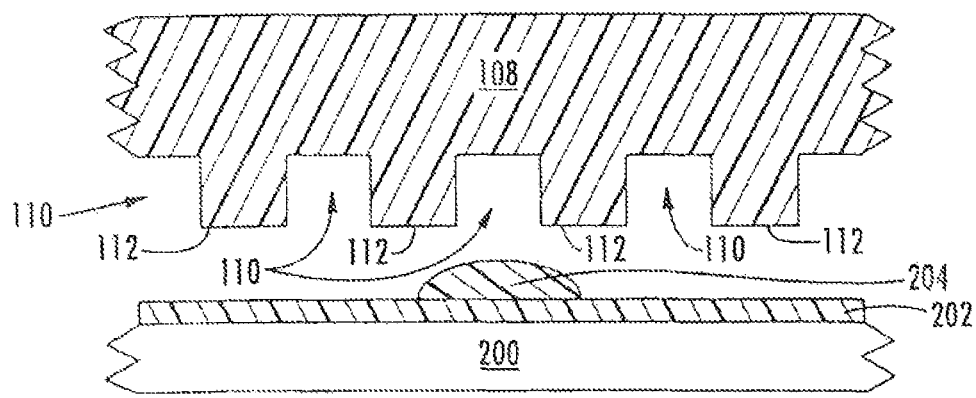
FIGS. 2A-2F are a schematic representation of the presently disclosed method for forming one or more micro- and/or nanoscale particles.

Referring now to FIG. 2A, in some embodiments, a substrate 200, for example, a silicon wafer, is treated or is coated with a non-wetting material 202. In some embodiments, non-wetting material 202 includes an elastomer (such a solvent resistant elastomer, including but not limited to a PFPE elastomer) that can be further exposed to UV light and cured to form a thin, non-wetting layer on the surface of substrate 200. Substrate 200 also can be made non-wetting by treating substrate 200 with non-wetting agent 202, for example a small molecule, such as an alkyl- or fluoroalkyl-silane, or other surface treatment. Continuing with FIG. 2A, a droplet 204 of a curable resin, a monomer, or a solution from which the desired particles will be formed is then placed on the coated substrate 200.

Figure 2B:
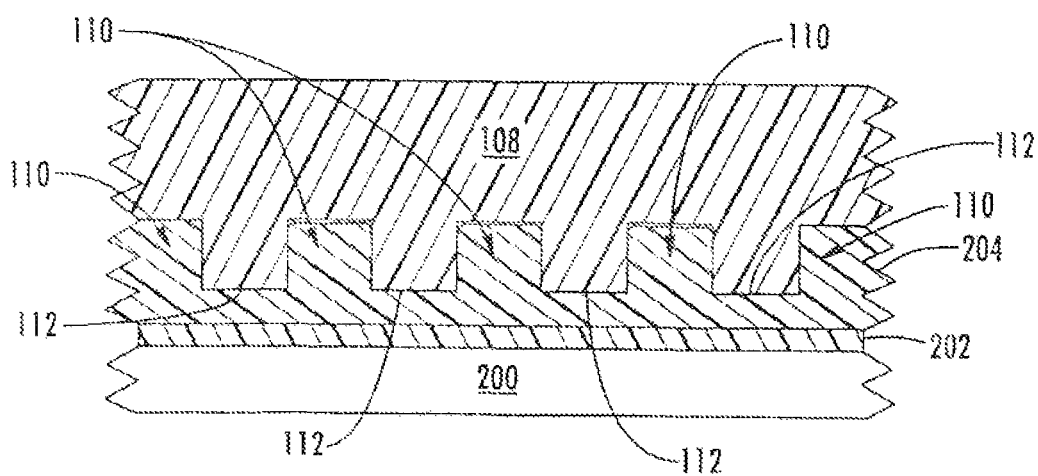

Referring now to FIG. 2A and FIG. 2B, patterned template 108 (as shown in FIG. 1D) is then contacted with droplet 204 of a particle precursor material so that droplet 204 fills the plurality of recessed areas 110 of patterned template 108.

Figure 2C:
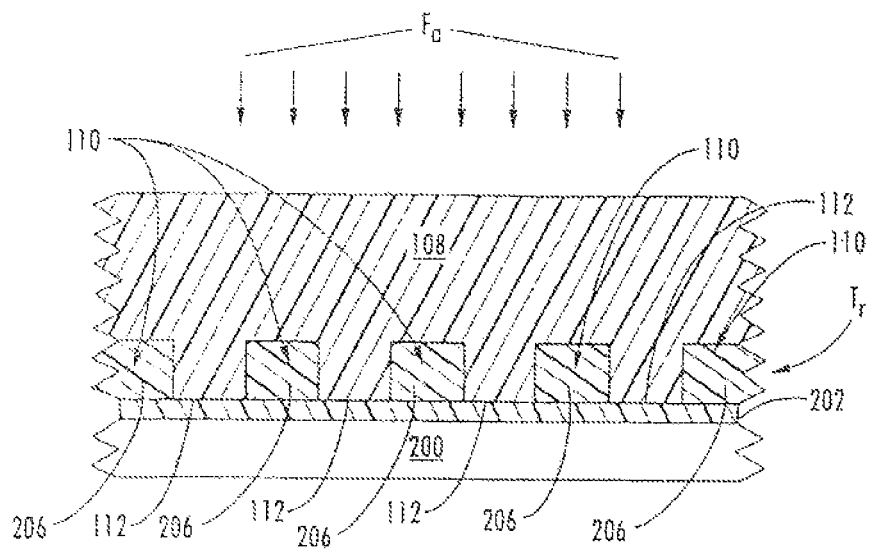
Figure 2D:
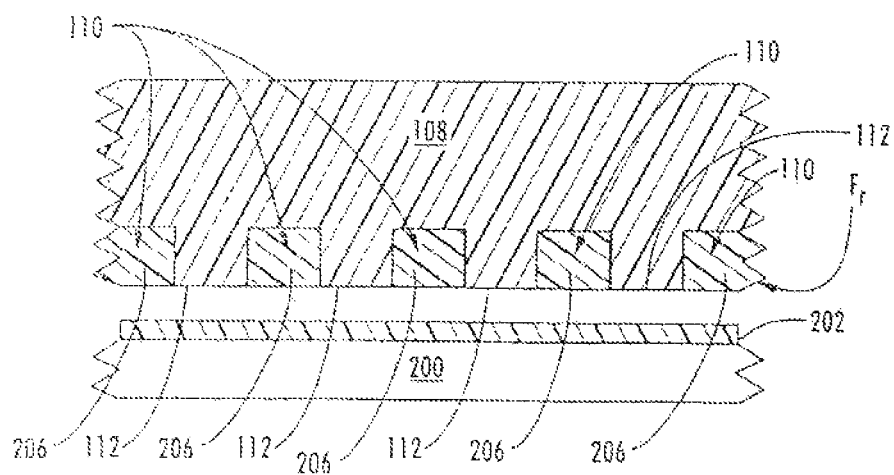

Referring now to FIGS. 2C and 2D, in some embodiments a force $F_a$ is applied to patterned template 108. While not wishing to be bound by any particular theory, once force $F_a$ is applied, the affinity of patterned template 108 for non-wetting coating or surface treatment 202 on substrate 200 in combination with the non-wetting behavior of patterned template 108 and surface treated or coated substrate 200 causes droplet 204 to be excluded from all areas except for recessed areas 110. Further, in embodiments essentially free of non-wetting or low wetting material 202 with which to sandwich droplet 204, a "scum" layer forms that interconnects the objects being stamped.

Continuing with FIGS. 2C and 2D, the particle precursor material filling recessed areas 110, e.g., a resin, monomer, solvent, combinations thereof, or the like, is then treated by a treating process $T_r$, e.g., photocured, UV-light treated, or actinic radiation treated, through patterned template 108 or thermally cured while under pressure, to form a plurality of micro- and/or nanoparticles 206. In some embodiments, a material, including but not limited to a polymer, an organic compound, or an inorganic compound, can be dissolved in a solvent, patterned using patterned template 108, and the solvent can be released.

Continuing with FIGS. 2C and 2D, once the material filling recessed areas 110 is treated, patterned template 108 is removed from substrate 200. Micro- and/or nanoparticles 206 are confined to recessed areas 110 of patterned template 108. In some embodiments, micro- and/or nanoparticles 206 can be retained on substrate 200 in defined regions once patterned template 108 is removed.

According to other embodiments, substrate 200 is not utilized and the material filling recessed areas 110 that becomes micro and/or nanoparticles 206 enters recessed areas 110 through capillary force, wetting characteristics, passive filling, active filling, or the like as described elsewhere herein.

Figure 2E:
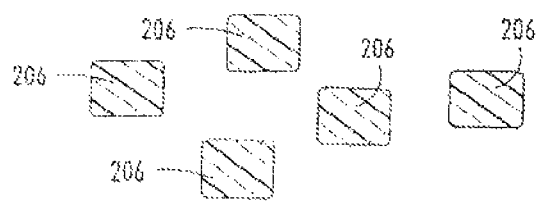

Referring now to FIGS. 2D and 2E, micro- and/or nanoparticles 206 can be removed from patterned template 108 to provide freestanding particles by a variety of methods, which include but are not limited to: (1) applying patterned template 108 to a surface that has an affinity for the particles 206; (2) deforming patterned template 108, or using other mechanical methods, including sonication, in such a manner that the particles 206 are naturally released from patterned template 108; (3) swelling patterned template 108 reversibly with supercritical carbon dioxide or another solvent that will extrude the particles 206; (4) washing patterned template 108 with a solvent that has an affinity for the particles 206 and will wash them out of patterned template 108; (5) applying patterned template 108 to a liquid that when hardened physically entraps particles 206; (6) applying patterned template 108 to a material that when hardened has a chemical and/or physical interaction with particles 206.

Figure 2F:
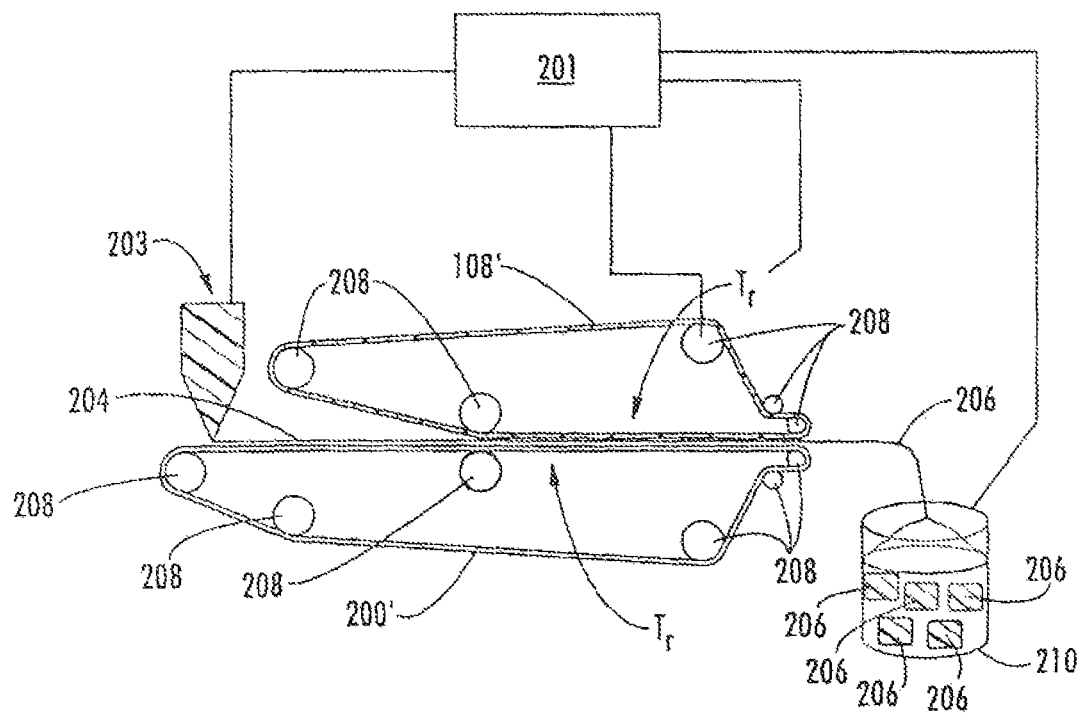

In some embodiments, the method of producing and harvesting particles includes a batch process. In some embodiments, the batch process is selected from one of a semi-batch process and a continuous batch process. Referring now to FIG. 2F, an embodiment of the presently disclosed subject matter wherein particles 206 are produced in a continuous process is schematically presented. An apparatus 199 is provided for carrying out the process. Indeed, while FIG. 2F schematically presents a continuous process for particles, apparatus 199 can be adapted for batch processes, and for providing a pattern on a substrate continuously or in batch, in accordance with the presently disclosed subject matter and based on a review of the presently disclosed subject matter by one of ordinary skill in the art.

Continuing, then, with FIG. 2F, droplet 204 of liquid material is applied to substrate 200' via reservoir 203. Substrate 200' can be coated or not coated with a non-wetting agent. Substrate 200' and pattern template 108' are placed in a spaced relationship with respect to each other and are also operably disposed with respect to each other to provide for the conveyance of droplet 204 between patterned template 108' and substrate 200'. Conveyance is facilitated through the provision of pulleys 208, which are in operative communication with controller 201. By way of representative non-limiting examples, controller 201 can include a computing system, appropriate software, a power source, a radiation source, and/or other suitable devices for controlling the functions of apparatus 199. Thus, controller 201 provides for power for and other control of the operation of pulleys 208 to provide for the conveyance of droplet 204 between patterned template 108' and substrate 200'. Particles 206 are formed and treated between substrate 200' and patterned template 108' by a treating process $T_R$, which is also controlled by controller 201. Particles 206 are collected in an inspecting device 210, which is also controlled by controller 201. Inspecting device 210 provides for one of inspecting, measuring, and both inspecting and measuring one or more characteristics of particles 206. Representative examples of inspecting devices 210 are disclosed elsewhere herein.

By way of further exemplifying embodiments of particle harvesting methods described herein, reference is made to FIGS. 3A-3F and FIGS. 4A-4G. In FIGS. 3A-3C and FIGS. 4A-4C particles which are produced in accordance with embodiments described herein remain in contact with an article 3700, 3800. The article 3700, 3800 can have an affinity for particles 3705 and 3805, respectively, or the particles can simple remain in the mold recesses following fabrication of the particles therein. In one embodiment, article 3700 is a patterned template or mold as described herein and article 3800 is a substrate as described herein.

Figure 3A:
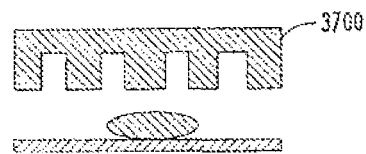
FIGS. 3A-3F are schematic representations of one embodiment of a method of the presently disclosed subject matter for harvesting particles from an article.
Figure 3B:
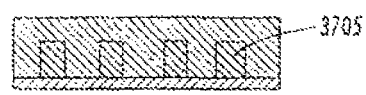
Figure 3C:
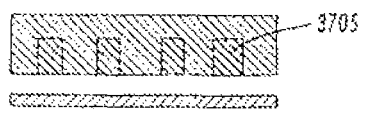
Figure 3D:
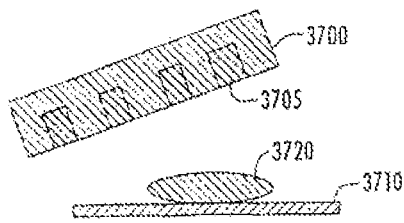
Figure 3E:
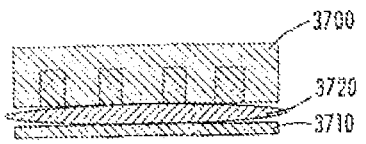
Figure 3F:
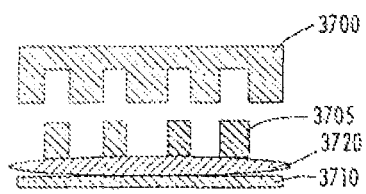
Figure 4A:
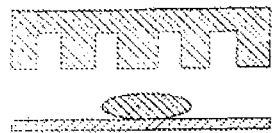
FIGS. 4A-4G are schematic representations of one embodiment of a method of the presently disclosed subject matter for harvesting particles from an article.
Figure 4B:
Figure 4C:
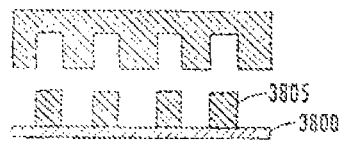
Figure 4D:
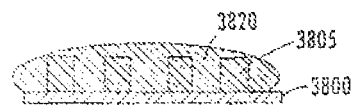
Figure 4E:
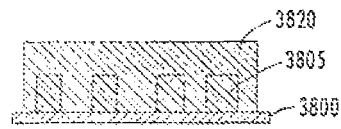
Figure 4F:
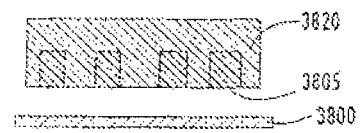
Figure 4G:
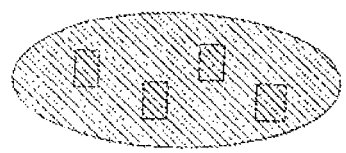

Referring now to FIGS. 3D-3F and FIGS. 4D-4G, material 3720, 3820 having an affinity for particles 3705, 3805 is put into contact with particles 3705, 3805 while particles 3705, 3805 remain in communication with articles 3700, 3800. In the embodiment of FIG. 3D, material 3720 is disposed on surface 3710. In the embodiment of FIG. 4D, material 3820 is applied directly to article 3800 having particles 3820. As illustrated in FIGS. 3E, 4D in some embodiments, article 3700, 3800 is put in engaging contact with material 3720, 3820. In one embodiment material 3720, 3820 is thereby dispersed to coat at least a portion of substantially all of particles 3705, 3805 while particles 3705, 3805 are in communication with article 3700, 3800 (e.g., a patterned template). In one embodiment, illustrated in FIGS. 3F and 4F, articles 3700, 3800 are substantially disassociated with material 3720, 3820. In one embodiment, material 3720, 3820 has a higher affinity for particles 3705, 3805 than any affinity between article 3700, 3800 and particles 3705, 3805. In FIGS. 3F and 4F, the disassociation of article 3700, 3800 from material 3720, 3820 thereby releases particles 3705, 3805 from article 3700, 3800 leaving particles 3705, 3805 associated with material 3720, 3820.

In one embodiment material 3720, 3820 has an affinity for particles 3705 and 3805. For example, material 3720, 3820 can include an adhesive or sticky surface such that when it is applied to particles 3705 and 3805 the particles remain associated with material 3720, 3820 rather than with article 3700, 3800. In other embodiments, material 3720, 3820 undergoes a transformation after it is brought into contact with article 3700, 3800. In some embodiments that transformation is an inherent characteristic of material 3705, 3805. In other embodiments, material 3705, 3805 is treated to induce the transformation. For example, in one embodiment material 3720, 3820 is an epoxy that hardens after it is brought into contact with article 3700, 3800. Thus, when article 3700, 3800 is pealed away from the hardened epoxy, particles 3705, 3805 remain engaged with the epoxy and not article 3700, 3800. In other embodiments, material 3720, 3820 is water that is cooled to form ice. Thus, when article 3700, 3800 is stripped from the ice, particles 3705, 3805 remain in communication with the ice and not article 3700, 3800. In one embodiment, the particle in connection with ice can be melted to create a liquid with a concentration of particles 3705, 3805. In some embodiments, material 3705, 3805 include, without limitation, one or more of a carbohydrate, an epoxy, a wax, polyvinyl alcohol, polyvinyl pyrrolidone, polybutyl acrylate, a polycyano acrylate and polymethyl methacrylate. In some embodiments, material 3720, 3820 includes, without limitation, one or more of liquids, solutions, powders, granulated materials, semi-solid materials, suspensions, combinations thereof, or the like.

In some embodiments, the plurality of recessed areas includes a plurality of cavities. In some embodiments, the plurality of cavities includes a plurality of structural features. In some embodiments, the plurality of structural features have a dimension ranging from about 10 microns to about 1 nanometer in size. In some embodiments, the plurality of structural features have a dimension ranging from about 1 micron to about 100 nm in size. In some embodiments, the plurality of structural features have a dimension ranging from about 100 nm to about 1 mm in size. In some embodiments, the plurality of structural features have a dimension in both the horizontal and vertical plane.

In some embodiments, the method of producing particles includes positioning the patterned template and the substrate in a spaced relationship to each other such that the patterned template surface and the substrate face each other in a predetermined alignment.

In some embodiments, an article is contacted with the layer of liquid material and a force is applied to the article to thereby remove the liquid material from the one of the patterned material and the substrate. In some embodiments, the article is selected from the group including a roller, a "squeegee" blade type device, a nonplanar polymeric pad, combinations thereof, or the like. In some embodiments, the liquid material is removed by some other mechanical apparatus.

In some embodiments, the contacting of the patterned template surface with the substrate forces essentially all of the disposed liquid material from between the patterned template surface and the substrate.

In some embodiments, the treating of the liquid material includes a process selected from the group including a thermal process, a phase change, an evaporative process, a photochemical process, and a chemical process.

In some embodiments, the mechanical force is applied by contacting one of a doctor blade and a brush with the one or more particles. In some embodiments, the mechanical force is applied by ultrasonics, megasonics, electrostatics, or magnetics means.

In some embodiments, the method includes harvesting or collecting the particles. In some embodiments, the harvesting or collecting of the particles includes a process selected from the group including scraping with a doctor blade, a brushing process, a dissolution process, an ultrasound process, a megasonics process, an electrostatic process, and a magnetic process. In some embodiments, the harvesting or collecting of the particles includes applying a material to at least a portion of a surface of the particle wherein the material has an affinity for the particles. In some embodiments, the material includes an adhesive or sticky surface. In some embodiments, the material includes, without limitation, one or more of a carbohydrate, an epoxy, a wax, polyvinyl alcohol, polyvinyl pyrrolidone, polybutyl acrylate, a polycyano acrylate, a polyhydroxyethyl methacrylate, a polyacrylic acid and polymethyl methacrylate. In some embodiments, the harvesting or collecting of the particles includes cooling water to form ice (e.g., in contact with the particles). In some embodiments, the presently disclosed subject matter describes a particle or plurality of particles formed by the methods described herein. In some embodiments, the plurality of particles includes a plurality of monodisperse particles. According to some embodiments, monodisperse particles are particles that have a physical characteristic that falls within a normalized size distribution tolerance limit. According to some embodiments, the size characteristic, or paramater, that is analyzed is the surface area, circumference, a linear dimension, mass, volume, three dimensional shape, shape, or the like.

According to some embodiments, the particles have a normalized size distribution of between about 0.80 and about 1.20, between about 0.90 and about 1.10, between about 0.95 and about 1.05, between about 0.99 and about 1.01, between about 0.999 and about 1.001, combinations thereof, and the like. Furthermore, in other embodiments the particles have a mono-dispersity. According to some embodiments, dispersity is calculated by averaging a dimension of the particles. In some embodiments, the dispersity is based on, for example, surface area, length, width, height, mass, volume, porosity, combinations thereof, and the like.

In some embodiments, the particle or plurality of particles is selected from the group including a semiconductor device, a crystal, a drug delivery vector, a gene delivery vector, a disease detecting device, a disease locating device, a photovoltaic device, a porogen, a cosmetic, an electret, an additive, a catalyst, a sensor, a detoxifying agent, an abrasive, such as a CMP, a micro-electro-mechanical system (MEMS), a cellular scaffold, a taggant, a pharmaceutical agent, and a biomarker. In some embodiments, the particle or plurality of particles include a freestanding structure.

According to some embodiments, a material can be incorporated into a particle composition or a particle according to the present invention, to treat or diagnose diseases including, but not limited to, Allergies; Anemia; Anxiety Disorders; Autoimmune Diseases; Back and Neck Injuries; Birth Defects; Blood Disorders; Bone Diseases; Cancers; Circulation Diseases; Dental Conditions; Depressive Disorders; Digestion and Nutrition Disorders; Dissociative Disorders; Ear Conditions; Eating Disorders; Eye Conditions; Foodborne Illnesses; Gastrointestinal Diseases; Genetic Disorders; Heart Diseases; Heat and Sun Related Conditions; Hormonal Disorders; Impulse Control Disorders; Infectious Diseases; Insect Bites and Stings; Institutes; Kidney Diseases; Leukodystrophies; Liver Diseases; Mental Health Disorders; Metabolic Diseases; Mood Disorders; Neurological Disorders; Organizations; Personality Disorders; Phobias; Pregnancy Complications; Prion Diseases; Prostate Diseases; Registries; Respiratory Diseases; Sexual Disorders; Sexually Transmitted Diseases; Skin Conditions; Sleep Disorders; Speech-Language Disorders; Sports Injuries; Thyroid Diseases; Tropical Diseases; Vestibular Disorders; Waterborne Illnesses; and other diseases such as found at: http://www.mic.ki.se/Diseases/Alphalist.html, which is incorporated herein by reference in its entirety including each reference cited therein.

In some embodiments, the method of producing particles includes tailoring the chemical composition of these materials and controlling the reaction conditions, whereby it is then possible to organize the biorecognition motifs so that the efficacy of the particle is optimized. In some embodiments, the particles are designed and synthesized so that recognition elements are located on the surface of the particle in such a way to be accessible to cellular binding sites, wherein the core of the particle is preserved to contain bioactive agents, such as therapeutic molecules. In some embodiments, a non-wetting imprint lithography method is used to fabricate the objects, wherein the objects are optimized for a particular application by incorporating functional motifs, such as biorecognition agents, into the object composition. In some embodiments, the method further includes controlling the microscale and nanoscale structure of the object by using methods selected from the group including self-assembly, stepwise fabrication procedures, reaction conditions, chemical composition, crosslinking, branching, hydrogen bonding, ionic interactions, covalent interactions, and the like. In some embodiments, the method further includes controlling the microscale and nanoscale structure of the object by incorporating chemically organized precursors into the object. In some embodiments, the chemically organized precursors are selected from the group including block copolymers and core-shell structures.

IA. Micro and Nano Particles

Dimensions

According to some embodiments of the presently disclosed subject matter, a particle is formed that has a shape corresponding to a mold (e.g., the particle has a shape reflecting the shape of the mold within which the particle was formed) having a desired shape and is less than about 100 μm in a given dimension (e.g. minimum, intermediate, or maximum dimension). In some embodiments, the particle is a nano-scale particle. According to some embodiments, the nano-scale particle has a dimension, such as a diameter or linear measurement that is less than 500 micron. The dimension can be measured across the largest portion of the particle that corresponds to the parameter being measured. In other embodiments, the dimension is less than 250 micron. In other embodiments, the dimension is less than 100 micron. In other embodiments, the dimension is less than 50 micron. In other embodiments, the dimension is less than 10 micron. In other embodiments, the dimension is between 1 nm and 1,000 nm. In some embodiments, the dimension is less than 1,000 nm. In other embodiments, the dimension is between 1 nm and 500 nm. In yet other embodiments, the dimension is between 1 nm and 100 nm.

According to some embodiments, particles formed in the patterned templates described herein are less than about 10 μm in a dimension. In other embodiments, the particle is between about 10 μm and about 1 μm in dimension. In yet further embodiments, the particle is less than about 1 μm in dimension. According to some embodiments the particle is between about 1 nm and about 500 nm in a dimension. According to other embodiments, the particle is between about 10 nm and about 200 nm in a dimension. In still further embodiments, the particle is between about 80 nm and 120 nm in a dimension. According to still more embodiments the particle is between about 20 nm and about 120 nm in dimension. The dimension of the particle can be a predetermined dimension, a cross-sectional diameter, a circumferential dimension, or the like.

According to further embodiments, the particles include patterned features that are about 2 nm in a dimension. In still further embodiments, the patterned features are between about 2 nm and about 200 nm. In other embodiments, the particle is less than about 80 nm in a widest dimension.

According to other embodiments, the particles produced by the methods and materials of the presently disclosed subject matter have a poly dispersion index (i.e., normalized size distribution) of between about 0.80 and about 1.20, between about 0.90 and about 1.10, between about 0.95 and about 1.05, between about 0.99 and about 1.01, between about 0.999 and about 1.001, combinations thereof, and the like. Furthermore, in other embodiments the particle has a monodispersity. According to some embodiments, dispersity is calculated by averaging a dimension of the particles. In some embodiments, the dispersity is based on, for example, surface area, length, width, height, mass, volume, porosity, combinations thereof, and the like.

According to other embodiments, particles of many predetermined regular and irregular shape and size configurations can be made with the materials and methods of the presently disclosed subject matter. Examples of representative particle shapes that can be made using the materials and methods of the presently disclosed subject matter include, but are not limited to, non-spherical, spherical, viral shaped, bacteria shaped, cell shaped, rod shaped (e.g., where the rod is less than about 200 nm in diameter), chiral shaped, right triangle shaped, fiat shaped (e.g., with a thickness of about 2 nm, disc shaped with a thickness of greater than about 2 nm, or the like), bi-concave disc shaped, annular shaped with or without an opening in its center, boomerang shaped, combinations thereof, and the like.

Composition

The particle can be of an organic material or an inorganic material and can be one uniform compound or component or a mixture of compounds or components. In some embodiments, an organic material molded with the materials and methods of the present invention includes a material that includes a carbon molecule. According to some embodiments, the particle can be of a high molecular weight material. According to some embodiments, a particle is composed of a matrix that has a predetermined surface energy. In some embodiments, the material that forms the particle includes more than about 50 percent liquid. In some embodiments, the material that forms the particle includes less than about 50 percent liquid. In some embodiments, the material that forms the particle includes less than about 10 percent liquid.

In some embodiments, the material from which the particles are formed includes, without limitation, one or more of a polymer, a liquid polymer, a solution, a monomer, a plurality of monomers, a polymerization initiator, a polymerization catalyst, an inorganic precursor, an organic material, a natural product, a metal precursor, a pharmaceutical agent, a tag, a magnetic material, a paramagnetic material, a ligand, a cell penetrating peptide, a porogen, a surfactant, a plurality of immiscible liquids, a solvent, a charged species, combinations thereof, or the like.

In some embodiments, the monomer includes butadienes, styrenes, propene, acrylates, methacrylates, vinyl ketones, vinyl esters, vinyl acetates, vinyl chlorides, vinyl fluorides, vinyl ethers, acrylonitrile, methacrylonitrile, acrylamide, methacrylamide allyl acetates, fumarates, maleates, ethylenes, propylenes, tetrafluoroethylene, ethers, isobutylene, fumaronitrile, vinyl alcohols, acrylic acids, amides, carbohydrates, esters, urethanes, siloxanes, formaldehyde, phenol, urea, melamine, isoprene, isocyanates, epoxides, bisphenol A, alcohols, chlorosilanes, dihalides, dienes, alkyl olefins, ketones, aldehydes, vinylidene chloride, anhydrides, saccharide, acetylenes, naphthalenes, pyridines, tactams, lactones, acetals, thiiranes, episulfide, peptides, derivatives thereof, and combinations thereof.

In yet other embodiments, the polymer includes polyamides, proteins, polyesters, polystyrene, polyethers, polyketones, polysulfones, polyurethanes, polysiloxanes, polysilanes, cellulose, amylose, polyacetals, polyethylene, glycols, poly(acrylate)s, poly(methacrylate)s, poly(vinyl alcohol), poly(vinylidene chloride), poly(vinyl acetate), poly(ethylene glycol), polystyrene, polyisoprene, polyisobutylenes, poly (vinyl chloride), poly(propylene), poly(lactic acid), polyisocyanates, polycarbonates, alkyds, phenolics, epoxy resins, polysulfides, polyimides, liquid crystal polymers, heterocyclic polymers, polypeptides, conducting polymers including polyacetylene, polyquinoline, polyaniline, polypyrrole, polythiophene, and poly(p-phenylene), dendimers, fluoropolymers, derivatives thereof, combinations thereof.

In some embodiments, the particle includes a biodegradable polymer. In other embodiments, the polymer is modified to be a biodegradable polymer (e.g., a poly(ethylene glycol) that is functionalized with a disulfide group). In some embodiments, the biodegradable polymer includes, without limitation, one or more of a polyester, a polyanhydride, a polyamide, a phosphorous-based polymer, a poly(cyanoacrylate), a polyurethane, a polyorthoester, a polydihydropyran, a polyacetal, combinations thereof, or the like.

In some embodiments, the polyester includes, without limitation, one or more of polylactic acid, polyglycolic acid, poly(hydroxybutyrate), poly(c-caprolactone), poly(β-malic acid), poly(dioxanones), combinations thereof, or the like. In some embodiments, the polyanhydride includes, without limitation, one or more of poly(sebacic acid), poly(adipic acid), poly(terpthalic acid), combinations thereof, or the like. In yet other embodiments, the polyamide includes, without limitation, one or more of poly(imino carbonates), polyaminoacids, combinations thereof, or the like.

According to some embodiments, the phosphorous-based polymer includes, without limitation, one or more of a polyphosphate, a polyphosphonate, a polyphosphazene, combinations thereof, or the like. Further, in some embodiments, the biodegradable polymer further includes a polymer that is responsive to a stimulus. In some embodiments, the stimulus includes, without limitation, one or more of pH, radiation, ionic strength, oxidation, reduction, temperature, an alternating magnetic field, an alternating electric field, combinations thereof, or the like. In some embodiments, the stimulus includes an alternating magnetic field.

In still further embodiments, the material from which the particles are formed includes a non-wetting agent. According to another embodiment, the material is a liquid material in a single phase. In other embodiments, the liquid material includes a plurality of phases. In some embodiments, the liquid material includes, without limitation, one or more of multiple liquids, multiple immiscible liquids, surfactants, dispersions, emulsions, micro-emulsions, micelles, particulates, colloids, porogens, active ingredients, combinations thereof, or the like.

According to other embodiments, the particle can be substantially coated. The coating, for example, can be a sugar based coating where the sugar is preferably a glucose, sucrose, maltose, derivatives thereof, combinations thereof, or the like.

Therapeutic Agent and/or Functionalization

In some embodiments, the particle includes a therapeutic or diagnostic agent coupled with the particle. The therapeutic or diagnostic agent can be physically coupled or chemically coupled with the particle, encompassed within the particle, at least partially encompassed within the particle, coupled to the exterior of the particle, combinations thereof, and the like.

The therapeutic agent can be a drug, a biologic, a ligand, an oligopeptide, a cancer treating agent, a viral treating agent, a bacterial treating agent, a fungal treating agent, combinations thereof, or the like.

In some embodiments, a therapeutic agent for combination with the particles of the presently disclosed subject matter is selected from one of a drug and genetic material. In some embodiments, the genetic material includes, without limitation, one or more of a non-viral gene vector, DNA, RNA, RNAi, a viral particle, agents described elsewhere herein, combinations thereof, or the like.

In some embodiments, a pharmaceutical agent can be combined with the particle material. The pharmaceutical agent can be, but is not limited to, a drug, a peptide, RNAi, DNA, combinations thereof, or the like. In other embodiments, the tag is selected from the group including a fluorescence tag, a radiolabeled tag, a contrast agent, combinations thereof, or the like. In some embodiments, the ligand includes a cell targeting peptide, or the like.

According to some embodiments, the particle is hydrophilic such that the particle avoids clearance by biological organism, such as a human.

In yet other embodiments, the particle can include a functional location such that the particle can be used as an analytical material. According to such embodiments, a particle includes a functional molecular imprint. The functional molecular imprint can include functional monomers arranged as a negative image of a functional template. The functional template, for example, can be but is not limited to, chemically functional and size and shape equivalents of an enzyme, a protein, an antibiotic, an antigen, a nucleotide sequence, an amino acid, a drug, a biologic, nucleic acid, combinations thereof, or the like. In other embodiments, the particle itself, for example, can be, but is not limited to, an artificial functional molecule. In one embodiment, the artificial functional molecule is a functionalized particle that has been molded from a molecular imprint. As such, a molecular imprint is generated in accordance with methods and materials of the presently disclosed subject matter and then a particle is formed from the molecular imprint, in accordance with further methods and materials of the presently disclosed subject matter. Such an artificial functional molecule includes substantially similar steric and chemical properties of a molecular imprint template. In one embodiment, the functional monomers of the functionalized particle are arranged substantially as a negative image of functional groups of the molecular imprint.

In some embodiments, additional components are included with the material of the particle to functionalize the particle. According to these embodiments the additional components can be encased within the isolated structures, partially encased within the isolated structures, on the exterior surface of the isolated structures, combinations thereof, or the like. Additional components can include, but are not limited to, drugs, biologics, more than one drug, more than one biologic, combinations thereof, and the like.

In some embodiments, the drug is a psychotherapeutic agent. In other embodiments, the psychotherapeutic agent is used to treat depression and can include, for example, sertraline, venlafaxine hydrochloride, paroxetine, bupropion, citalopram, fluoxetine, mirtazapine, escitalopram, and the like. In some embodiments, the psychotherapeutic agent is used to treat schizophrenia and can include, for example, olanazapine, risperidone, quetiapine, aripiprazole, ziprasidone, and the like. According to other embodiments, the psychotherapeutic agent is used to treat attention deficit disorder (ADD) or attention deficit hyperactivity disorder (ADHD), and can include, for example, methylphenidate, atomoxetine, amphetamine, dextroamphetamine, and the like. In some other embodiments, the drug is a cholesterol drug and can include, for example, atorvastatin, simvastatin, pravastatin, ezetimibe, rosuvastatin, fenofibrate fluvastatin, and the like. In yet some other embodiments, the drug is a cardiovascular drug and can include, for example, amlodipine, valsartan, losartan, hydrochlorothiazide, metoprolol, candesartan, ramipril, irbesartan, amlodipine, benazepril, nifedipine, carvedilol, enalapril, telemisartan, quinapril, doxazosin mesylate, felodipine, lisinopril, and the like. In some embodiments, the drug is a blood modifier and can include, for example, epoetin aifa, darbepoetin alfa, epoetin beta, clopidogrel, pegfilgrastim, filgrastim, enoxaparin, Factor VIIA, antihemophilic factor, immune globulin, and the like. According to a further embodiment, the drug can include a combination of the above listed drugs.

In some embodiments, the material of the particles or the additional components included with the particles of the presently disclosed subject matter can include, but are not limited, to anti-infective agents. In some embodiments, the anti-infective agent is used to treat bacterial infections and can include, for example, azithromycin, amoxicillin, clavulanic acid, levofloxacin, clarithromycin, ceftriaxone, ciprofloxacin, piperacillin, tazobactam sodium, imipenem, cilastatin, linezolid, meropenem, cefuroxime, moxitloxacin, and the like. In some embodiments the anti-infective agent is used to treat viral infections and can include, for example, lamivudine, zidovudine, valacyclovir, peginterferon, lopinavir, ritonavir, tenofovir, efavirenz, abacavir, lamivudine, zidovudine, atazanavir, and the like. In other embodiments, the anti-infective agent is used to treat fungal infections and can include, for example, terbinafine, fluconazole, itraconazole, caspofungin acetate, and the like. In some embodiments, the drug is a gastrointestinal drug and can include, for example, esomeprazole, lansoprazole, omeprazole, pantoprazole, rabeprazole, ranitidine, ondansetron, and the like. According to yet other embodiments, the drug is a respiratory drug and can include, for example, fluticasone, salmeterol, montelukast, budesonide, formoterol, fexofenadine, cetirizine, desloratadine, mometasone furoate, tiotropium, albuterol, ipratropium, palivizumab, and the like. In yet other embodiments, the drug is an antiarthritic drug and can include, for example, celecoxib, infliximab, etanercept, rofecoxib, valdecoxib, adalimumab, meloxicam, diclofenac, fentanyl, and the like. According to a further embodiment, the drug can include a combination of the above listed drugs.

According to alternative embodiments, the material of the particles or the additional components included with the particles of the presently disclosed subject matter can include, but are not limited to an anticancer agent and can include, for example, nitrogen mustard, cisplatin, doxorubicin, docetaxel, anastrozole, trastuzumab, capecitabine, letrozole, leuprolide, bicalutamide, goserelin, rituximab, oxaliplatin, bevacizumab, irinotecan, paclitaxel, carboplatin, imatinib, gemcitabine, temozolomide, gefitinib, and the like. In some embodiments, the drug is a diabetes drug and can include, for example, rosiglitazone, pioglitazone, insulin, glimepiride, voglibose, and the like. In other embodiments, the drug is an anticonvulsant and can include, for example, gabapentin, topiramate, oxcarbazepine, carbamazepine, lamotrigine, divalproex, levetiracetam, and the like. In some embodiments, the drug is a bone metabolism regulator and can include, for example, alendronate, raloxifene, risedronate, zoledronic, and the like. In some embodiments, the drug is a multiple sclerosis drug and can include, for example, interferon, glatiramer, copolymer-1, and the like. In other embodiments, the drug is a hormone and can include, for example, somatropin, norelgestromin, norethindrone, desogestrel, progestin, estrogen, octreotide, levothyroxine, and the like. In yet other embodiments, the drug is a urinary tract agent, and can include, for example, tamsulosin, finasteride, tolterodine, and the like. In some embodiments, the drug is an immunosuppressant and can include, for example, mycophenolate mofetil, cyclosporine, tacrolimus, and the like. In some embodiments, the drug is an ophthalmic product and can include, for example, latanoprost, dorzolamide, botulinum, verteporfin, and the like. In some embodiments, the drug is a vaccine and can include, for example, pneumococcal, hepatitis, influenza, diphtheria, and the like. In other embodiments, the drug is a sedative and can include, for example, zolpidem, zaleplon, eszopiclone, and the like. In some embodiments, the drug is an Alzheimer disease therapy and can include, for example, donepexil, rivastigmine, tacrine, and the like. In some embodiments, the drug is a sexual dysfunction therapy and can include, for example, sildenafil, tadalafil, alprostadil, levothyroxine, and the like. In an alternative embodiment, the drug is an anesthetic and can include, for example, sevoflurane, propofol, mepivacaine, bupivacaine, ropivacaine, lidocaine, nesacaine, etidocaine, and the like. In some embodiments, the drug is a migraine drug and can include, for example, sumatriptan, almotriptan, rizatriptan, naratriptan, and the like. In some embodiments, the drug is an infertility agent and can include, for example, follitropin, choriogonadotropin, menotropin, follicle stimulating hormone (FSH), and the like. In some embodiments, the drug is a weight control product and can include, for example, orlistat, dexfenfluramine, sibutramine, and the like. According to a further embodiment, the drug can include a combination of the above listed drugs. According to other embodiments, one or more other drugs can be included with the particles of the presently disclosed subject matter and can be found in Physician's Desk Reference, Thomson Healthcare, 59th Bk&Cr edition (2004), which is incorporated herein by reference in its entirety.

In some embodiments, one or more additional components are included with the particles. The additional components can include: targeting ligands such as cell-targeting peptides, cell-penetrating peptides, integrin receptor peptide (GRGDSP), melanocyte stimulating hormone, vasoactive intestinal peptide, anti-Her2 mouse antibodies and antibody fragments, and the like; vitamins; viruses; polysaccharides; cyclodextrins; liposomes; proteins; oligonucleotides; aptamers; optical nanoparticles such as CdSe for optical applications; borate nanoparticles to aid in boron neutron capture therapy (BNCT) targets; combinations thereof; and the like.

In use, the particles of the presently disclosed subject matter can be used as treatment devices. In such uses, the particle is administered in a therapeutically effective amount to a patient.

Controlled or Timed Release

According to some embodiments, the particles can be controlled or time-release drug delivery vehicles. A co-constituent of the particle, such as a polymer for example, can be cross-linked to varying degrees. Depending upon the amount of cross-linking of the polymer, another co-constituent of the particle, such as an active agent, can be configured to be released from the particle as desired. The active can be released with no restraint, controlled release, or can be completely restrained within the particle. In some embodiments, the particle can be functionalized to methods and materials disclosed herein, to target a specific biological site, cell, tissue, agent, combinations thereof, or the like. Upon interaction with the targeted biological stimulus, a co-constituent of the particle can be broken down to begin releasing the active co-constituent of the particle. In one example, the polymer can be poly(ethylene glycol) (PEG), which can be cross-linked between about 5% and about 100%. The active co-constituent that can be doxorubicin that is included in the cross-linked PEG particle. In one embodiment, when the PEG co-constituent is cross-linked about 100%, no doxorubicin leaches out of the particle.

In certain embodiments, the particle includes a composition of material that imparts controlled, delayed, immediate, or sustained release of cargo of the particle or composition, such as for example, sustained drug release. According to some embodiments, materials and methods used to form controlled, delayed, immediate, or sustained release characteristics of the particles of the present invention include the materials, methods, and formulations disclosed in U.S. Patent Application nos. 2006/0099262; 2006/0104909; 200610110462; 2006/0127484; 200410175428; 2004/0166157; and U.S. Pat. No. 6,964,780, each of which are incorporated herein by reference in their entirety.

Particle Design

In some embodiments, the particle fabrication process provides control of particle matrix composition, the ability for the particle to carry a wide variety of cargos, the ability to functionalize the particle for targeting and enhanced circulation, and/or the versatility to configure the particle into different dosage forms, such as inhalation, dermatological, injectable, and oral, to name a few.

According to some embodiments, the matrix composition is tailored to provide control over biocompatibility. In some embodiments, the matrix composition is tailored to provide control over cargo release. The matrix composition, in some embodiments, contains biocompatible materials with solubility and/or philicity, controlled mesh density and charge, stimulated degradation, and/or shape and size specificity while maintaining relative monodispersity.

According to further embodiments, the method for making particles containing cargo does not require the cargo to be chemically modified. In one embodiment, the method for producing particles is a gentle processing technique that allows for high cargo loading without the need for covalent bonding. In one embodiment, cargo is physically entrapped within the particle due to interactions such as Van der Waals forces, electrostatic, hydrogen bonding, other other intra- and inter-molecular forces, combinations thereof, and the like.

In some embodiments, the particles are functionalized for targeting and enhanced circulation. In some embodiments, these features allow for tailored bioavailability. In one embodiment, the tailored bioavailability increases delivery effectiveness. In one embodiment, the tailored bioavailability reduces side effects.

In some embodiments, a non-sperical particle has a surface area that is greater than the surface area of spherical particle of the same volume. In some embodiments, the number of surface ligands on the particle is greater than the number of surface ligands on a spherical particle of the same volume.

In some embodiments, one or more particles contain chemical moiety handles for the attachment of protein. In some embodiments, the protein is avidin. In some embodiments biotinylated reagents are subsequently bound to the avidin. In some embodiments the protein is a cell penetrating protein. In some embodiments, the protein is an antibody fragment. In one embodiment, the particles are used for specific targeting (e.g., breast tumors in female subjects). In some embodiments, the particles contain chemotherapeutics. In some embodiments, the particles are composed of a cross link density or mesh density designed to allow slow release of the chemotherapeutic. The term crosslink density means the mole fraction of prepolymer units that are crosslink points. Prepolymer units include monomers, macromonomers and the like.

In some embodiments, the physical properties of the particle are varied to enhance cellular uptake. In some embodiments, the size (e.g., mass, volume, length or other geometric dimension) of the particle is varied to enhance cellular uptake. In some embodiments, the charge of the particle is varied to enhance cellular uptake. In some embodiments, the charge of the particle ligand is varied to enhance cellular uptake. In some embodiments, the shape of the particle is varied to enhance cellular uptake.

In some embodiments, the physical properties of the particle are varied to enhance biodistribution. In some embodiments, the size (e.g., mass, volume, length or other geometric dimension) of the particle is varied to enhance biodistribution. In some embodiments, the charge of the particle matrix is varied to enhance biodistribution. In some embodiments, the charge of the particle ligand is varied to enhance biodistribution. In some embodiments, the shape of the particle is varied to enhance biodistribution. In some embodiments, the aspect ratio of the particles is varied to enhance biodistribution.

In some embodiments, the physical properties of the particle are varied to enhance cellular adhesion. In some embodiments, the size (e.g., mass, volume, length or other geometric dimension) of the particle is varied to enhance cellular adhesion. In some embodiments, the charge of the particle matrix is varied to enhance cellular adhesion. In some embodiments, the charge of the particle ligand is varied to enhance cellular adhesion. In some embodiments, the shape of the particle is varied to enhance cellular adhesion.

In some embodiments, the particles are configured to degrade in the presence of an intercellular stimulus. In some embodiments, the particles are configured to degrade in a reducing environment. In some embodiments, the particles contain crosslinking agents that are configured to degrade in the presence of an external stimulus. In some embodiments, the crosslinking agents are configured to degrade in the presence of a pH condition, a radiation condition, an ionic strength condition, an oxidation condition, a reduction condition, a temperature condition, an alternating magnetic field condition, an alternating electric field condition, combinations thereof, or the like. In some embodiments, the particles contain crosslinking agents that are configured to degrade in the presence of an external stimulus and/or a therapeutic agent.

In some embodiments, the particles contain crosslinking agents that are configured to degrade in the presence of an external stimulus, a targeting ligand, and a therapeutic agent. In some embodiments, the therapeutic agent is a drug or a biologic. In some embodiments the therapeutic agent is DNA, RNA, or siRNA.

In some embodiments, particles are configured to degrade in the cytoplasm of a cell. In some embodiments, particles are configured to degrade in the cytoplasm of a cell and release a therapeutic agent. In some embodiments, the therapeutic agent is a drug or a biologic. In some embodiments the therapeutic agent is DNA, RNA, or siRNA. In some embodiments, the particles contain poly(ethylene glycol) and crosslinking agents that degrade in the presence of an external stimulus.

In some embodiments, the particles are used for ultrasound imaging. In some embodiments, the particles used for ultrasound imaging are composed of bioabsorbable polymers. In some embodiments, particles used for ultrasound imaging are porous. In some embodiments, particles used for ultrasound imaging are composed of poly(lactic acid), poly(D,L-lactic acid-co-glycolic acid), and combinations thereof.

In some embodiments, the particles contain magnetite and are used as contrast agents. In some embodiments, the particles contain magnetite and are functionalized with linker groups and are used as contrast agents. In some embodiments, the particles, are functionalized with a protein. In some embodiments, the particles are functionalized with N-hydroxysuccinimidyl ester groups. In some embodiments, avidin is bound to the particles. In some embodiments, particles containing magnetite are covalently bound to avidin and exposed to a biotinylated reagent.

Particles to Mimic Natural Structures

In some embodiments, the particles are shaped to mimic natural structures. In some embodiments, the particles are shaped to mimic natural structures and contain a therapeutic agent, a contrast agent, a targeting ligand, combination thereof, and the like.

Particles, materials of particles, and methods of making particles, make it feasible to study physiological questions about the restriction of particle movement in the interstitial and perivascular space in brain. The size range and shape capabilities of the presently disclosed particles increase the likelihood of gathering this information.

Mechano-chemico functionality plays a role in the biodistribution and intracellular trafficking of carriers, such as the particles described herein. Designing specific bio-distribution and intracellular trafficking carries can make for a more efficacious diagnosis, and can lead to superior therapeutic and prevention strategies to fight disease. These specifically designed carries and methods can be extended to mimic biological systems and, to manipulate biological systems.

Figure 5A:
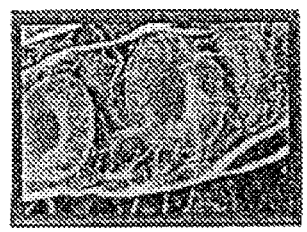
FIGS. 5A-5C are schematic representations of red blood cells.
Figure 5B:
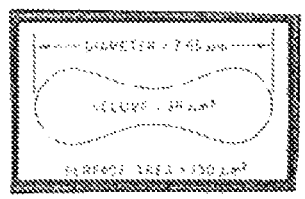
Figure 5C:

Referring to FIG. 5, mammalian red blood cells are composed of a lipid membrane coupled to a flexible cytoskeleton. The disc shape of red blood cells provides a large surface-to-volume ratio which may aid in absorption or exchange of oxygen and carbon dioxide. Red blood cells can pass through capillaries as small as 3 μm, having reversible elastic deformation with strains less than 100%. Red blood cells severely deform through Intercellular gaps of sinusoids in the spleen, where stiffened and aged red blood cells are removed after 120 days.

Enhanced rigidification of red blood cells is a key feature of the biology and pathophysiology of malaria (Miller, et al. *Nature* (2002); Cooke, et al. *Adv. Parasitology* (2001); and Glenister, et. al *Blood* (2002); each of which is incorporated herein by reference). Sickle cell anemia is another RBC-based condition which is caused by elogated RBCs. PEGylation of RBCs has been used to camouflage the blood group antigens to make universal RBCs (Nacharaju et al. *Transfusion* (2005), which is incorporated herein by reference).

Figure 6:
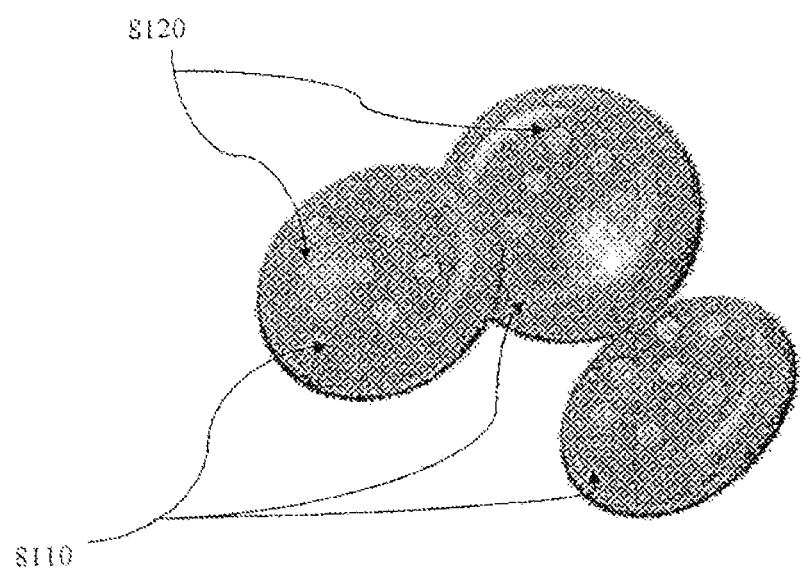
FIG. 6 is a schematic representation of a substantially disc-shaped particle with cargo.

Referring to FIG. 6, in some embodiments, particles 8110 are substantially cell-shaped. In some embodiments, particles 8110 are substantially red blood cell-shaped. In some embodiments, particles 8110 are substantially red blood cell-shaped and composed of a matrix with a modulus less than about 1 MPa. In some embodiments, the modulus can be selected from, for example, the modulus of elasticity, Young's modulus, or the like. In some embodiments, particles 8110 are substantially disc shaped.

According to some embodiments, particles 8110 have dimensions substantially similar to red blood cells. In some embodiments, particle 8110 has a largest linear dimension of about 5 μm to about 10 μm; preferably about 8 μm.

According to some embodiments, particle 8110 has a surface area of about 130 μm$^2$. According to some embodiments, particle 8110 has a volume of about 98 μm$^3$.

According to some embodiments, particles 8110 within a given plurality of particles are monodisperse as described herein.

According to some embodiments, particle 8110 is configured to mimic the properties of a red blood cell. According to some embodiments, particle 8110 has a modulus of less than about 1 MPa. In some embodiments, particle 8110 has a modulus of less than about 1 MPa such that particle 8110 can pass through a tube having an inner diameter of less than about 3 µm. In some embodiments, the tube may be a blood vessel. The modulus of particle 8110 may be varied using porogens to create pores in particle 8110.

According to some embodiments, particle 8110 includes polyethylene glycol. In some embodiments, particle 8110 includes perfluororopolyether. In some embodiments, particle 8110 is hydrophilic. In some embodiments, the blood gas permeability of particle 8110 is substantially similar to a red blood cell. In some embodiments, particle 8110 comprises a material with high oxygen permeability.

Figure 7:
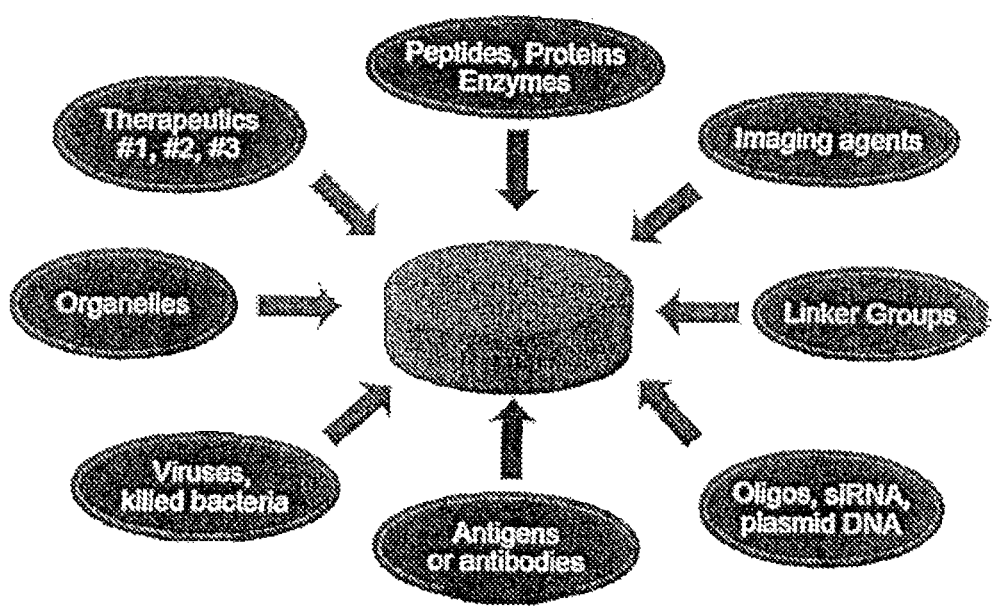
FIG. 7 is a schematic representation of various cargo and functionalization which may be applied to a particle.

Referring to FIG. 6, particle 8110 may have a surface functionality and/or cargo. In some embodiments, the surface functionality and/or cargo is added to particle 8110 for a therapeutic or imaging purpose. Surface functionality and/or cargo may include petides, proteins, enzymes, imaging agents, linker groups, oliogos, siRNA, plasmid DNA, antigens or antibodies, viruses, killed bacteria, organelles, and therapeutics. See also FIG. 7.

In some embodiments, particle 8110 includes surface functionality. The surface functionalization may include, for example, a natural mimic for extended delivery or imaging, PEGylation, or blood type antigens.

In some embodiments, particle 8110 includes cargo 8120. In some embodiments, cargo 8120 is capable of binding and/or releasing oxygen. In some embodiments, cargo 8120 is capable of binding and/or releasing carbon dioxide. In some embodiments, cargo 8120 is capable of binding and/or releasing oxygen and carbon dioxide. Cargo 8120 may include, but is not limited to, a therapeutic agent, hemoglobin, or an imaging agent. In some embodiments, cargo 8120 comprises a surface functionality. In other embodiments, cargo 8120 is distributed throughout particle 8110. In some embodiments, cargo 8120 is on a surface of particle 8120.

In some embodiments, particle 8110 is loaded with mitochondria. Relevant properties and uses of mitochondria are described in "Mitochondrial DNA Isolation Kit", BioVision Research Products, available at http://www.blovision.com/pdf/K280-50.pdf, which is incorporated by reference in its entirety. Mitochondria are known to aid in aerobic respiration, the creation of the eukaryotic cell, and eventually complex multicellular organisms. Recent reports have found that mitochondria play essential roles in aging and determining lifespan. A variety of heritable and acquired diseases have been linked to mitochondrial dysfunction. In the article, "Mitochondrial Transfer Between Cells Can Rescue Aerobic Respiration," Tulane University Health Sciences Center, PNAS, vol. 102, no. 5, Jan. 31, 2006, available at http://www.pnas.org/cgi/content/full/103/5/1283; http://www.futurepundit.com/mt/mt-altcomments.cgi?entry_id=2396, which is incorporated by reference in its entirety, Jeffrey L. Spees et al. report that mitochondria are more dynamic than previously considered: mitochondria or mtDNA can move between cells. The active transfer from adult stem cells and somatic cells can rescue aerobic respiration in mammalian cells with nonfunctional mitochondria.

Bid is a BH3 only member of the Bcl-2 family that regulates cell death at the level of mitochondrial membranes. Bid appears to link the mitochondrial pathway with the death receptor mediated pathway of cell death. It is generally assumed that the f.l. (fulllength) protein becomes activated after proteolytic cleavage, especially by apical caspases like caspase 8. The cleaved protein then relocates to mitochondria and promotes membrane permeabilization, presumably by interaction with mitochondrial lipids and other Bcl-2 proteins that facilitate the release of apoptogenic proteins like cytochrome c. Although the major action may reside in the C terminus part, tBid (cleaved Bid), un-cleaved Bid also has pro apoptotic potential when ectopically expressed in cells or in vitro. This pro apoptotic action of fl. Bid has remained unexplained, especially at the biochemical level. In the article, "Pro-apoptotic Bid Induces Membrane Perturbation by Inserting Selected Lysolipids into the Biolayer," The University of Manchetser, Biochem. J., 387, pp. 109-118, 2005, available at http://www.pubmedcentral.nih.gov/articlerender.fcgi?artid=1134938, which is incorporated by reference in its entirety, Goonesinghe et al. explain that f.l. (full-length) Bid can insert specific lysolipids into the membrane surface, thereby priming mitochondria for the release of apoptogenic factors. This is reported to be most effective for lysophosphatidylcholine species to accumulate in mitochondria during apoptosis induction. A Bid mutant that is not pro-apoptotic in vivo is defective in lysophosphatidylcholine mediated membrane perturbation in vitro. Results of this study provide a biochemical explanation for the pro-apoptotic action of f.l. Bid.

In some embodiments, particle 8110 is used to trigger cell death. Particle 8110 may be configured to trigger cell death by a variety of means. According to some embodiments, cell death may be triggered by the incorporation of Cytochrome C into particle 8110 to trigger apoptosis by combining with Apaf-1 (Tang, et. al Cell 2006), membrane attack complex (MAC) or tear/saliva enzymes to punch holes in cells, salts, and therapeutics such as doxorubicin.

In some embodiments, the particles 8110 are configured to elicit an immune response. In some embodiments, particles 8110 are configured to elicit an immune response by at least one of the following methods: delivering antibodies for temporary immune protection in long-circulating carriers; delivering monokines and lymphokines to regulate immune response; using antigens to trigger immunological response; and the delivery of viruses.

Figure 8:
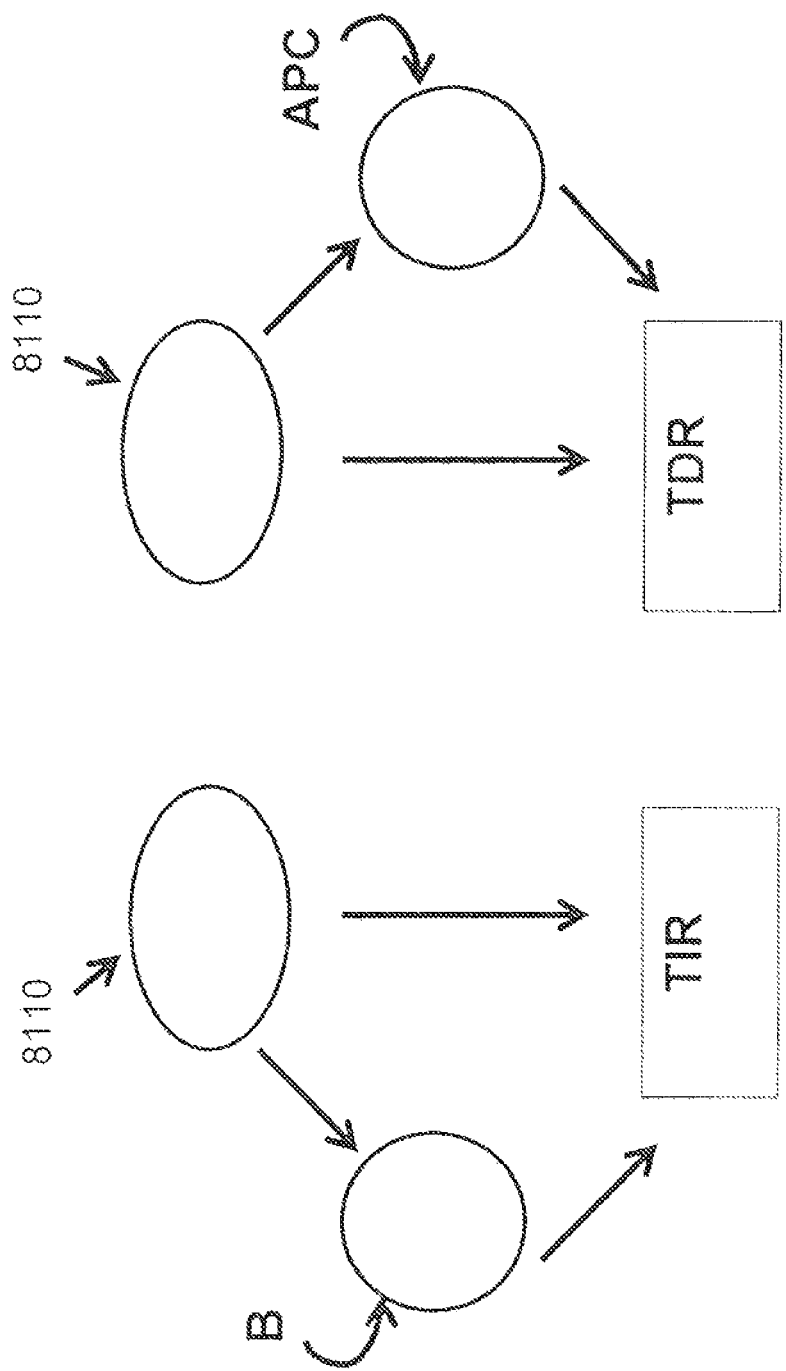
FIG. 8 is a schematic representation of the use of particles for immune response.

Referring to FIG. 8, particles 8110 may include epitope replicas:

T-independent response TIR: In some embodiments, particles 8110 evoke an antibody response. In some embodiments, particles 8110 stimulate B-cells B directly.

T-dependent response TDR: In some embodiments, particles 8110 are targeted to antigen-presenting cells APC (for example, dendritic cells) that are taken up via receptor mediated endocytosis. In some embodiments, bone marrow derived dendritic cells can be treated with particles of varying cargos/ligands and measure their uptake and antigen presenting competence.

In some embodiments, particles 8110 are configured to stimulate B-cells B. In some embodiments, B-cells B are stimulated by targeting ligands covalently bound to particles 8110. In some embodiments, B-cells B are stimulated by haptens bound to particles 8110. In some embodiments, the B-cells are stimulated by antigens bound to particles 8110.

Figure 9:
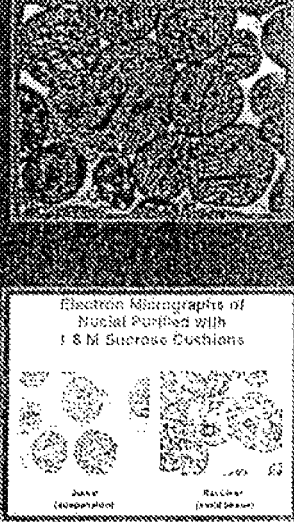
FIG. 9 is a schematic addressing use of particles to deliver organelles.

Referring to FIG. 9, particles 8110 of FIG. 6 can also be used to readily deliver organelles.

In some embodiments, particles 8110 are functionalized with targeting ligands. In some embodiments, particles 8110 are functionalized to target tumors. In some embodiments, particles 8110 are functionalized to target breast tumors. In some embodiments, particles 8110 are functionalized to target the HER2 receptor. In some embodiments, particles 8110 are functionalized to target breast tumors and contain a chemotherapeutic. In some embodiments, particles 8110 are functionalized to target dendritic cells.

According to some embodiments, particles 8110 have a predetermined zeta-potential.

IB. Introduction of Particle Precursor to Patterned Templates

According to some embodiments, the recesses of the patterned templates can be configured to receive a substance to be molded. According to such embodiments, variables such as, for example, the surface energy of the patterned template, the volume of the recess, the permeability of the patterned template, the viscosity of the substance to be molded as well as other physical and chemical properties of the substance to be molded interact and affect the willingness of the recess to receive the substance to be molded.

II. Functionalization of Particles

In some embodiments, the presently disclosed subject matter provides a method for functionalizing isolated micro- and/or nanoparticles.

Figure 10A:
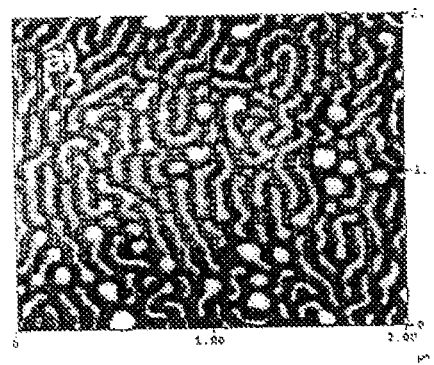
FIGS. 10A and 10B are an atomic force micrograph of mold fabrication from brush polymer masters.
Figure 10B:
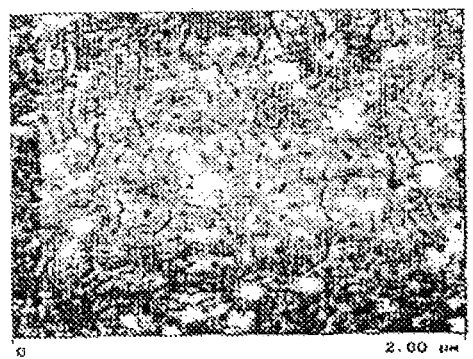
Figure 11A:
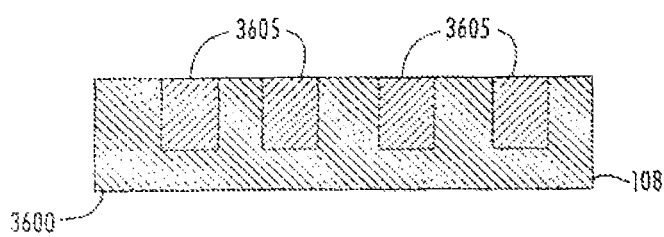
FIGS. 11A-11D are schematic representations of one embodiment of a method for functionalizing particles of the presently disclosed subject matter.
Figure 11B:
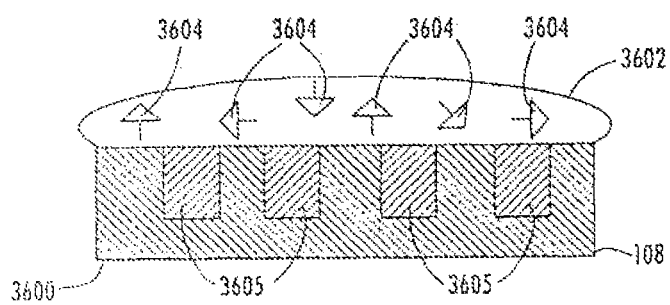

In one embodiment, the functionalization includes introducing chemical functional groups to a surface either physically or chemically. In some embodiments, the method of functionalization includes introducing at least one chemical functional group to at least a portion of microparticles and/or nanoparticles. In some embodiments, particles 3605 are at least partially functionalized while particles 3605 are in contact with an article 3600. In one embodiment, the particles 3605 to be functionalized are located within a mold or patterned template 108 (FIGS. 10A-11D). In some embodiments, particles 3605 to be functionalized are attached to a substrate (e.g., substrate 4010 of FIGS. 12A-12D). In some embodiments, at least a portion of the exterior of the particles 3605 can be chemically modified by performing the steps illustrated in FIGS. 11A-11D. In one embodiment, the particles 3605 to be functionalized are located within article 3600 as illustrated in FIGS. 11A and 12A. As illustrated in FIGS. 11A-11D and 12A-12D, some embodiments include contacting an article 3600 containing particles 3605 with a solution 3602 containing a modifying agent 3604.

Figure 11C:
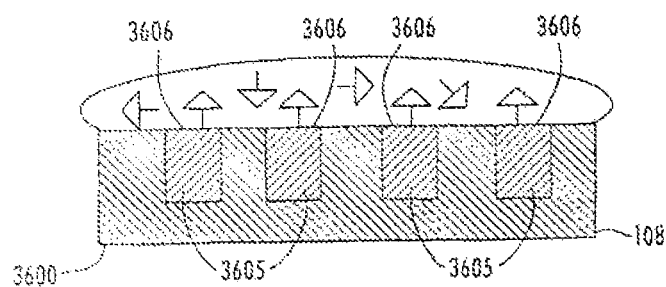
Figure 12A:
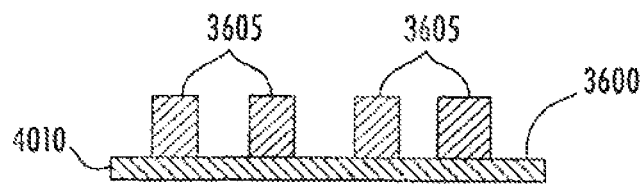
FIGS. 12A-12D are schematic representations of one embodiment of one process of the presently disclosed subject matter for harvesting particles from an article.
Figure 12B:
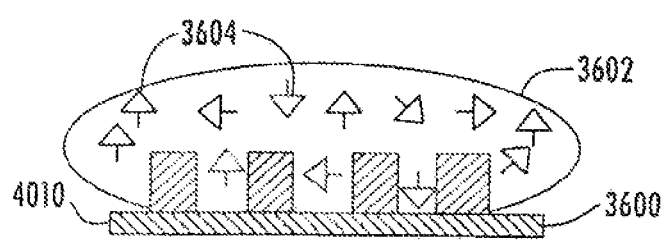
Figure 12C:
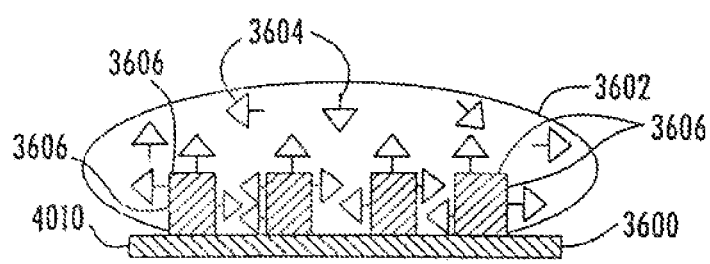

In one embodiment, illustrated in FIGS. 11C and 12C, modifying agent 3604 attaches (e.g., chemically) to exposed particle surface 3606 by chemically reacting with or physically adsorbing to a linker group on particle surface 3606. In one embodiment, the linker group on particle 3606 is a chemical functional group that can attach to other species via chemical bond formation or physical affinity. In some embodiments, modifying agents 3611 are contained within or partially within particles 3605. In some embodiments, the linker group includes a functional group that includes, without limitation, sulfides, amines, carboxylic acids, acid chlorides, alcohols, alkenes, alkyl halides, isocyanates, compounds disclosed elsewhere herein, combinations thereof, or the like.

Figure 11D:
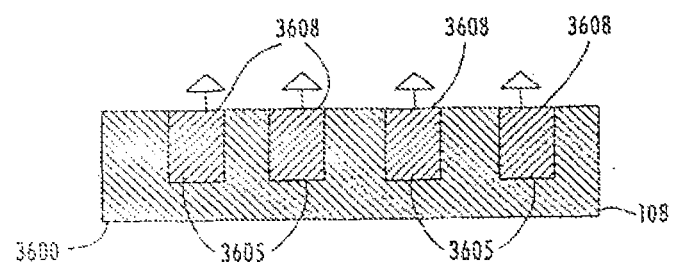
Figure 12D:
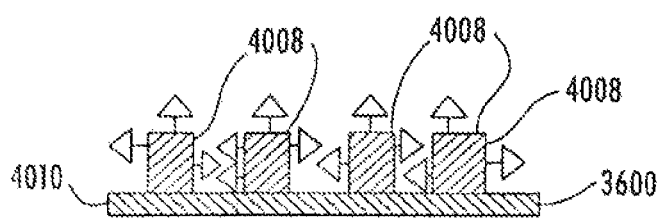

In one embodiment, illustrated in FIGS. 11D and 12D, excess solution is removed from article 3600 while particle 3605 remains in communication with article 3600. In some embodiments, excess solution is removed from the surface containing the particles. In some embodiments, excess solution is removed by rinsing with or soaking in a liquid, by applying an air stream, or by physically shaking or scraping the surface. In some embodiments, the modifying agent includes an agent selected from the group including dyes, fluorescent tags, radiolabeled tags, contrast agents, ligands, peptides, pharmaceutical agents, proteins, DNA, RNA, siRNA, compounds and materials disclosed elsewhere herein, combinations thereof, and the like.

In one embodiment, functionalized particles 3608, 4008 are harvested from article 3600 using, for example, methods described herein. In some embodiments, functionalizing and subsequently harvesting particles that reside on an article (e.g., a substrate, a mold or patterned template) have advantages over other methods (e.g., methods in which the particles must be functionalized while in solution). In one embodiment of the presently disclosed subject matter, fewer particles are lost in the process, giving a high product yield. In one embodiment of the presently disclosed subject matter, a more concentrated solution of the modifying agent can be applied in lower volumes. In one embodiment of the presently disclosed subject matter, where particles are functionalized while they remain associated with article 3600, functionalization does not need to occur in a dilute solution. In one embodiment, the use of more concentrated solution facilitates, for example, the use of lower volumes of modifying agent and/or lower times to functionalize. According to another embodiment, the functionalized particles are uniformly functionalized and each has substantially an identical physical load. In some embodiments, particles in a tight, 2-dimensional array, but not touching, are susceptible to application of thin, concentrated solutions for faster functionalization. In some embodiments, lower volume/higher concentration modifying agent solutions are useful, for example, in connection with modifying agents that are difficult and expensive to make and handle (e.g., biological agents such as peptides, DNA, or RNA). In some embodiments, functionalizing particles that remain connected to article 3600 eliminates difficult and/or time-consuming steps to remove excess unreacted material (e.g., dialysis, extraction, filtration and column separation). In one embodiment of the presently disclosed subject matter, highly pure functionalized product can be produced at a reduced effort and cost. Because the particles are molded in a substantially inert polymer mold, the contents of the particle can be controlled, thereby yielding a highly pure (e.g., greater than 95%) functionalized product.

In some embodiments, the liquid material from which the particles will be formed, or particle precursor, is selected from the group including a polymer, a solution, a monomer, a plurality of monomers, a polymerization initiator, a polymerization catalyst, an inorganic precursor, an organic material, a natural product, a metal precursor, a pharmaceutical agent, a tag, a magnetic material, a paramagnetic material, a superparamagnetic material, a ligand, a cell penetrating peptide, a porogen, a surfactant, a plurality of immiscible liquids, a solvent, a pharmaceutical agent with a binder, a charged species, combinations thereof, and the like. In some embodiments, the pharmaceutical agent Is selected from the group including a drug, a peptide, RNAi, DNA, combinations thereof, and the like. In some embodiments, the tag is selected from the group including a fluorescence tag, a radiolabeled tag, a contrast agent, combinations thereof, and the like. In some embodiments, the ligand includes a cell targeting peptide.

III. Removing/Harvesting the Patterned Structures from the Patterned Template and/or Substrate In some embodiments, the patterned structure (e.g., a patterned micro- or nanostructure) is removed from at least one of the patterned template and/or the substrate. This can be accomplished by a number of approaches, including but not limited to applying the surface element containing the patterned structure to a surface that has an affinity for the patterned structure; applying the surface element containing the patterned structure to a material that when hardened has a chemical and/or physical interaction with the patterned structure; deforming the surface element containing the patterned structure such that the patterned structure is released from the surface element; swelling the surface element containing the patterned structure with a first solvent to extrude the patterned structure; and washing the surface element containing the patterned structure with a second solvent that has an affinity for the patterned structure.

In some embodiments, a surface has an affinity for the particles. The affinity of the surface can be a result of, in some embodiments, an adhesive or sticky surface, such as for example but not limitation, carbohydrates, epoxies, waxes, polyvinyl alcohol, polyvinyl pyrrolidone, polybutyl acrylate, polycyano acrylates, polyhydroxyethyl methacrylate, polymethyl methacrylate, combinations thereof, and the like. In some embodiments, the liquid is water that is cooled to form ice. In some embodiments, the water is cooled to a temperature below the Tm of water but above the Tg of the particle. In some embodiments the water is cooled to a temperature below the Tg of the particles but above the Tg of the mold or substrate. In some embodiments, the water is cooled to a temperature below the Tg of the mold or substrate.

In some embodiments, the first solvent includes supercritical fluid carbon dioxide. In some embodiments, the first solvent includes water. In some embodiments, the first solvent includes an aqueous solution including water and a detergent. In embodiments, the deforming the surface element is performed by applying a mechanical force to the surface element. In some embodiments, the method of removing the patterned structure further includes a sonication method.

IV. Method of Patterning Natural and Synthetic Structures

In some embodiments, the presently disclosed subject matter describes methods and processes, and products by processes, for generating surfaces and molds from natural structures, single molecules, or self-assembled structures. Accordingly, in some embodiments, the presently disclosed subject matter describes a method of patterning a natural structure, single molecule, and/or a self-assembled structure. In some embodiments, the method further includes replicating the natural structure, single molecule, and/or a self-assembled structure. In some embodiments, the method further includes replicating the functionality of the natural structure, single molecule, and/or a self-assembled structure.

More particularly, in some embodiments, the method further includes taking the impression or mold of a natural structure, single molecule, and/or a self-assembled structure. In some embodiments, the impression or mold is taken with a low surface energy polymeric precursor. In some embodiments, the low surface energy polymeric precursor includes a perfluoropolyether (PFPE) functionally terminated diacrylate. In some embodiments, the natural structure, single molecule, and/or self-assembled structure includes, without limitation, one or more of enzymes, viruses, antibodies, micelles, tissue surfaces, combinations thereof, or the like.

In some embodiments, the impression or mold is used to replicate the features of the natural structure, single molecule, and/or a self-assembled structure into an isolated object or a surface. In some embodiments, a non-wetting imprint lithography method is used to impart the features into a molded part or surface. In some embodiments, the molded part or surface produced by this process can be used in many applications, including, but not limited to, drug delivery, medical devices, coatings, catalysts, or mimics of the natural structures from which they are derived. In some embodiments, the natural structure includes biological tissue. In some embodiments, the biological tissue includes tissue from a bodily organ, such as a heart. In some embodiments, the biological tissue includes vessels and bone. In some embodiments, the biological tissue includes tendon or cartilage. For example, in some embodiments, the presently disclosed subject matter can be used to pattern surfaces for tendon and cartilage repair. Such repair typically requires the use of collagen tissue, which comes from cadavers and must be machined for use as replacements. Most of these replacements fail because one cannot lay down the primary pattern that is required for replacement. The soft lithographic methods described herein alleviate this problem.

In some embodiments, the presently disclosed subject matter can be applied to tissue regeneration using stem cells. Almost all stem cell approaches known in the art require molecular patterns for the cells to seed and then grow, thereby taking the shape of an organ, such as a liver, a kidney, or the like. In some embodiments, the molecular scaffold is cast and used as crystals to seed an organ in a form of transplant therapy. In some embodiments, the stem cell and nano-substrate is seeded into a dying tissue, e.g., liver tissue, to promote growth and tissue regeneration. In some embodiments, the material to be replicated in the mold includes a material that is similar to or the same as the material that was originally molded. In some embodiments, the material to be replicated in the mold includes a material that is different from and/or has different properties than the material that was originally molded. This approach could play an important role in addressing the organ transplant shortage.

In some embodiments, the presently disclosed subject matter is used to take the impression of one of an enzyme, a bacterium, and a virus. In some embodiments, the enzyme, bacterium, or virus is then replicated into a discrete object or onto a surface that has the shape reminiscent of that particular enzyme, bacterium, or virus replicated into it. In some embodiments, the mold itself is replicated on a surface, wherein the surface-attached replicated mold acts as a receptor site for an enzyme, bacterium, or virus particle. In some embodiments, the replicated mold is useful as a catalyst, a diagnostic sensor, a therapeutic agent, a vaccine, combinations thereof, and the like. In some embodiments, the surface-attached replicated mold is used to facilitate the discovery of new therapeutic agents.

In some embodiments, the macromolecular, e.g., enzyme, bacterial, or viral, molded "mimics" serve as non-self-replicating entities that have the same surface topography as the original macromolecule, bacterium, or virus. In some embodiments, the molded mimics are used to create biological responses, e.g., an allergic response, to their presence, thereby creating antibodies or activating receptors. In some embodiments, the molded mimics function as a vaccine. In some embodiments, the efficacy of the biologically-active shape of the molded mimics is enhanced by a surface modification technique.

According to embodiments of the present invention, a substance disclosed herein, for example, a drug, DNA, RNA, a biological molecule, a super absorptive material, combinations thereof, and the like can be a substance that is deposited into recesses and molded into particle 8110. According to still further embodiments, a substance to be molded is, but is not limited to, a polymer, a solution, a monomer, a plurality of monomers, a polymerization initiator, a polymerization catalyst, an inorganic precursor, a metal precursor, a pharmaceutical agent, a tag, a magnetic material, a paramagnetic material, a ligand, a cell penetrating peptide, a porogen, a surfactant, a plurality of immiscible liquids, a solvent, a charged species, combinations thereof, and the like. In still further embodiments, particle 8110 is, but is not limited to, organic polymers, charged particles, polymer electrets (poly (vinylidene fluoride), Teflon-fluorinated ethylene propylene, polytetrafluoroethylene), therapeutic agents, drugs, non-viral gene vectors, RNAi, viral particles, polymorphs, combinations thereof, and the like.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Representative Procedure for Synthesis and Curing Photocurable Perfluoropolyethers In some embodiments, the synthesis and curing of PFPE materials of the presently disclosed subject matter is performed by using the method described by Rolland, J. P., et al., *J. Am. Chem. Soc.*, 2004, 126, 2322-2323. Briefly, this method involves the methacrylate-functionalization of a commercially available PFPE diol ($M_n$=3800 g/mol) with isocyanatoethyl methacrylate. Subsequent photocuring of the material is accomplished through blending with 1 wt % of 2,2-dimethoxy-2-phenylacetophenone and exposure to UV radiation ($\lambda$=365 nm).

More particularly, in a typical preparation of perfluoropolyether dimethacrylate (PFPE DMA), poly(tetrafluoroethylene oxide-co-difluoromethylene oxide)$\alpha,\omega$ diol (ZDOL, average $M_n$ ca. 3,800 g/mol, 95%, Aldrich Chemical Company, Milwaukee, Wis., United States of America) (5.7227 g, 1.5 mmol) was added to a dry 50 mL round bottom flask and purged with argon for 15 minutes. 2-isocyanatoethyl methacrylate (EIM, 99%, Aldrich) (0.43 mL, 3.0 mmol) was then added via syringe along with 1,1,2-trichlorotrifluoroethane (Freon 113 99%, Aldrich) (2 mL), and dibutyltin diacetate (DBTDA, 99%, Aldrich) (50 μL). The solution was immersed in an oil bath and allowed to stir at 50° C. for 24 h. The solution was then passed through a chromatographic column (alumina, Freon 113, 2×5 cm). Evaporation of the solvent yielded a clear, colorless, viscous oil, which was further purified by passage through a 0.22-μm polyethersulfone filter.

In a representative curing procedure for PFPE DMA, 1 wt % of 2,2-dimethoxy-2-phenyl acetophenone (DMPA, 99% Aldrich), (0.05 g, 2.0 mmol) was added to PFPE DMA (5 g, 1.2 mmol) along with 2 mL Freon 113 until a clear solution was formed. After removal of the solvent, the cloudy viscous oil was passed through a 0.22-μm polyethersulfone filter to remove any DMPA that did not disperse into the PFPE DMA. The filtered PFPE DMA was then irradiated with a UV source (Electro-Lite Corporation, Danbury, Conn., United States of America, UV curing chamber model no. 81432-ELC-500, $\lambda$=365 nm) while under a nitrogen purge for 10 min. This resulted in a clear, slightly yellow, rubbery material.

Example 2

Representative Fabrication of a PFPE DMA Device

In some embodiments, a PFPE DMA device, such as a stamp, was fabricated according to the method described by Rolland, J. P. et al., *J. Am. Chem. Soc.*, 2004, 126, 2322-2323. Briefly, the PFPE DMA containing a photoinitiator, such as DMPA, was spin coated (800 rpm) to a thickness of 20 μm onto a Si wafer containing the desired photoresist pattern. This coated wafer was then placed into the UV curing chamber and irradiated for 6 seconds. Separately, a thick layer (about 5 mm) of the material was produced by pouring the PFPE DMA containing photoinitiator into a mold surrounding the Si wafer containing the desired photoresist pattern. This wafer was irradiated with UV light for one minute. Following this, the thick layer was removed. The thick layer was then placed on top of the thin layer such that the patterns in the two layers were precisely aligned, and then the entire device was irradiated for 10 minutes. Once complete, the entire device was peeled from the Si wafer with both layers adhered together.

Example 3

Figure 13:
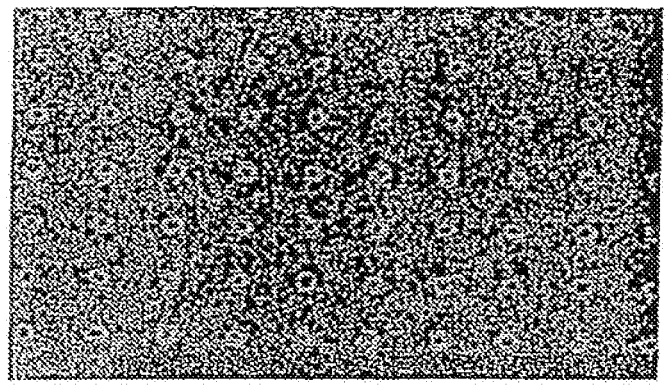
FIG. 13 is a scanning electron micrograph of a silicon master including 200 nm trapezoidal patterns.
Figure 14:
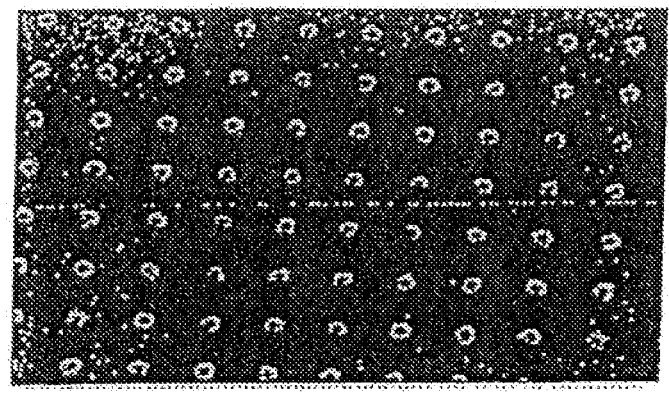
FIG. 14 is a scanning electron micrograph of 200-nm isolated trapezoidal particles of poly(ethylene glycol) (PEG) diacrylate.

Fabrication of Isolated Particles Using Non-Wetting Imprint Lithography 3.1 Fabrication of 200-nm Trapezoidal PEG Particles A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (See FIG. 13). A poly(dimethylsiloxane) mold is used to confine the liquid PFPE-DMA to the desired area. The apparatus was then subjected to UV light ($\lambda$=365 nm) for 10 minutes while under a nitrogen purge. The fully cured PFPE-DMA mold was then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 μL of PEG diacrylate is then placed on the treated silicon wafer and the patterned PFPE mold placed on top of it. The substrate is then placed in a molding apparatus and a small pressure is applied to push out excess PEG-diacrylate. The pressure used was at least about 100 N/cm$^2$. The entire apparatus was then subjected to UV light ($\lambda$=365 nm) for ten minutes while under a nitrogen purge. Particles are observed after separation of the PFPE mold and the treated silicon wafer using scanning electron microscopy (SEM) (see FIG. 14).

3.2 Fabrication of 500-nm Conical PEG Particles

Figure 15:
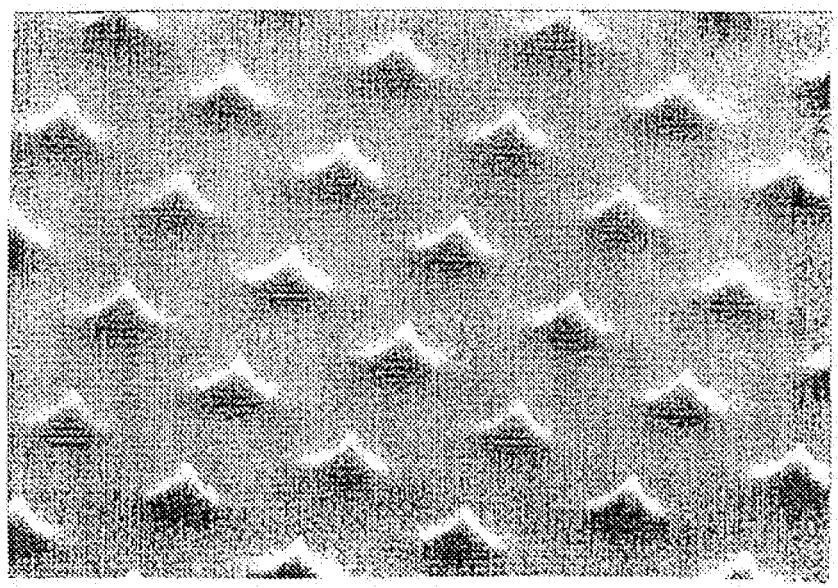
FIG. 15 is a scanning electron micrograph of a silicon master including 500 nm conical patterns that are <50 nm at the tip.
Figure 16:
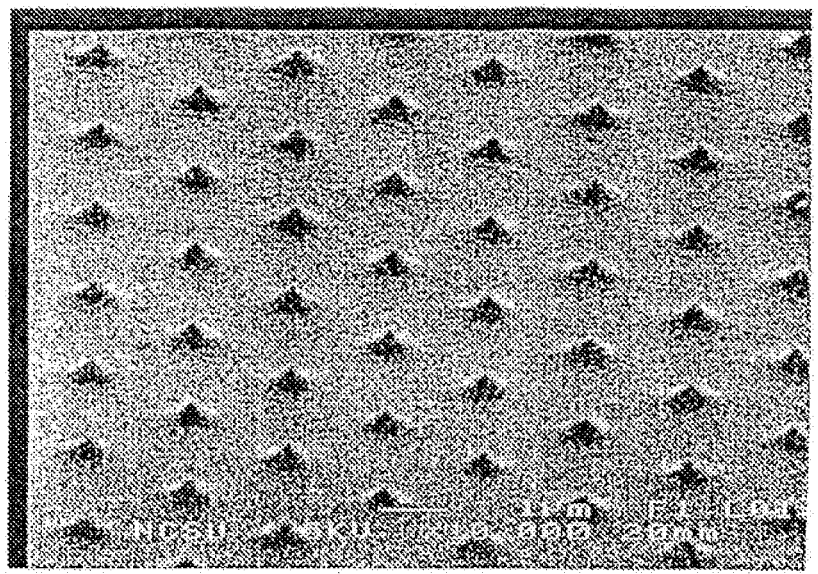
FIG. 16 is a scanning electron micrograph of 500-nm isolated conical particles of PEG diacrylate.

A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 15). A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro (1H, 1H, 2H, 2H-perfluorooctyl) silane via vapor deposition in a desiccator for 20 minutes. Following this, 50 μL of PEG diacrylate is then placed on the treated silicon wafer and the patterned PFPE mold placed on top of it. The substrate is then placed in a molding apparatus and a small pressure is applied to push out excess PEG-diacrylate. The entire apparatus is then subjected to UV light ($\lambda$=365 nm) for ten minutes while under a nitrogen purge. Particles are observed after separation of the PFPE mold and the treated silicon wafer using scanning electron microscopy (SEM) (see FIG. 16).

3.3 Fabrication of 3-µm Arrow-Shaped PEG Particles

Figure 17:
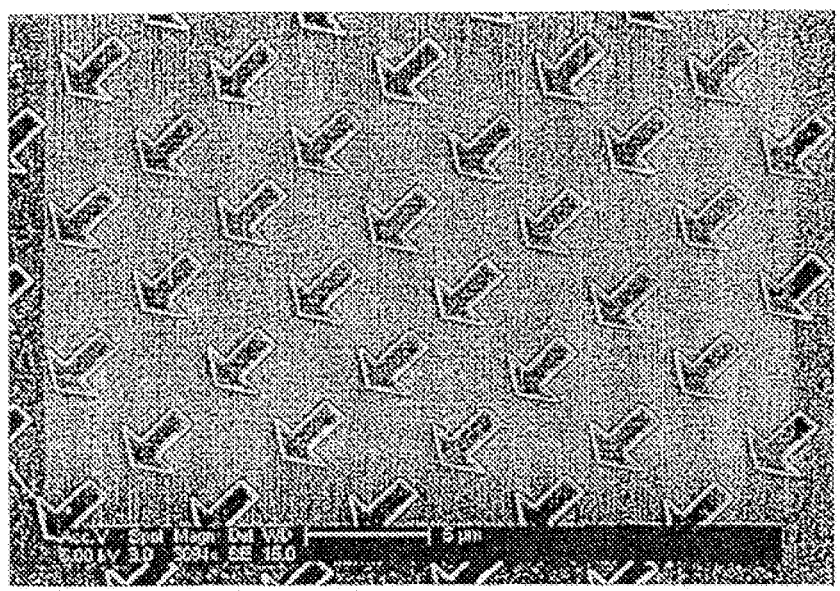
FIG. 17 is a scanning electron micrograph of a silicon master including 3-μm arrow-shaped patterns.
Figure 18:
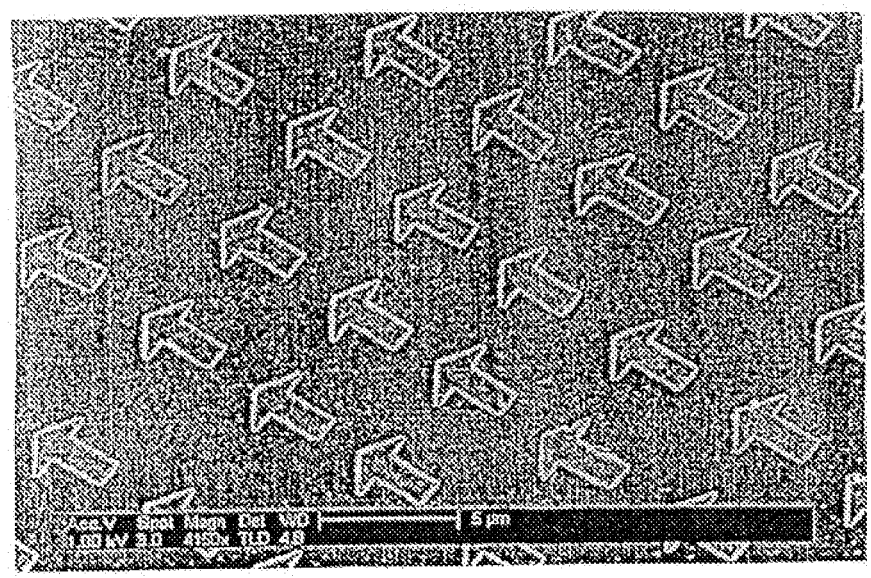
FIG. 18 is a scanning electron micrograph of 3-μm isolated arrow-shaped particles of PEG diacrylate.

A patterned perfluoropolyether (PFPE) mold is generated by pouring a PFPE-dimethacrylate (PFPE-DMA) containing 1-hydroxycyclohexyl phenyl ketone over a silicon substrate patterned with 3-µm arrow shapes (see FIG. 17). A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro (1H, 1H, 2H, 2H-perfluorooctyl) silane via vapor deposition in a desiccator for 20 minutes. Following this, 50 µL of PEG diacrylate is then placed on the treated silicon wafer and the patterned PFPE mold placed on top of it. The substrate is then placed in a molding apparatus and a small pressure is applied, to push out excess PEG-diacrylate. The entire apparatus is then subjected to UV light ($\lambda$=365 nm) for ten minutes while under a nitrogen purge. Particles are observed after separation of the PFPE mold and the treated silicon wafer using scanning electron microscopy (SEM) (see FIG. 18).

3.4 Fabrication of 200-nm×750-nm×250-nm Rectangular PEG Particles

Figure 19:
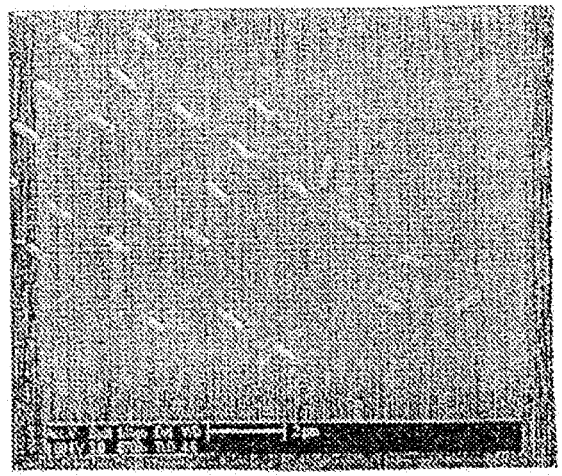
FIG. 19 is a scanning electron micrograph of 200-nm×750-nm×250-nm rectangular shaped particles of PEG diacrylate.

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm×750-nm×250-nm rectangular shapes. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 µL of PEG diacrylate is then placed on the treated silicon wafer and the patterned PFPE mold placed on top of it. The substrate is then placed in a molding apparatus and a small pressure is applied to push out excess PEG-diacrylate. The entire apparatus is then subjected to UV light ($\lambda$=365 nm) for ten minutes while under a nitrogen purge. Particles are observed after separation of the PFPE mold and the treated silicon wafer using scanning electron microscopy (SEM) (see FIG. 19).

Figure 20:
FIG. 20 is a scanning electron micrograph of 200-nm isolated trapezoidal particles of trimethylolpropane triacrylate (TMPTA).

3.5 Fabrication of 200-nm Trapezoidal Trimethylopropane Triacrylate (TMPTA) Particles A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light ($\lambda$=365 nm) for ten minutes while under a nitrogen purge. Particles are observed after separation of the PFPE mold and the treated silicon wafer using scanning electron microscopy (SEM) (see FIG. 20).

Figure 21:
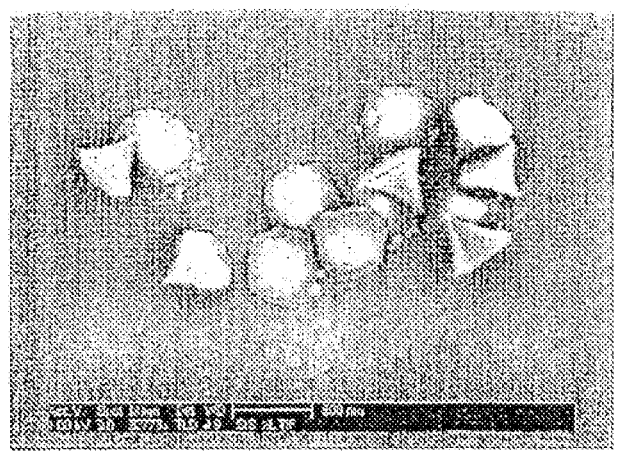
FIG. 21 is a scanning electron micrograph of 500-nm isolated conical particles of TMPTA.
Figure 22:
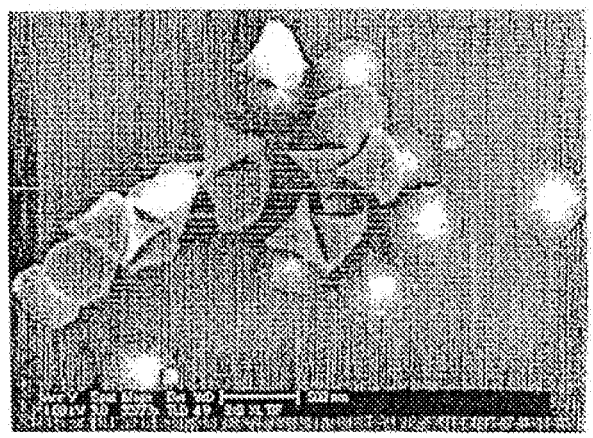
FIG. 22 is a scanning electron micrograph of 500-nm isolated conical particles of TMPTA, which have been printed using an embodiment of the presently described non-wetting imprint lithography method and harvested mechanically using a doctor blade.

3.6 Fabrication of 500-nm Conical Trimethyloporopane Triacrylate (TMPTA) Particles A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 15). A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light ($\lambda$=365 nm) for ten minutes while under a nitrogen purge. Particles are observed after separation of the PFPE mold and the treated silicon wafer using scanning electron microscopy (SEM) (see FIG. 21). Further, FIG. 22 shows a scanning electron micrograph of 500-nm isolated conical particles of TMPTA, which have been printed using an embodiment of the presently described non-wetting imprint lithography method and harvested mechanically using a doctor blade. The ability to harvest particles in such a way offers conclusive evidence for the absence of a "scum layer."

3.7 Fabrication of 3-µm Arrow-Shaped TMPTA Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 3-µm arrow shapes (see FIG. 17). A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light (λ=365 nm) for ten minutes while under a nitrogen purge. Particles are observed after separation of the PFPE mold and the treated silicon wafer using scanning electron microscopy (SEM).

3.8 Fabrication of 200-nm Trapezoidal Poly(Lactic Acid) (PLA) Particles

Figure 23:
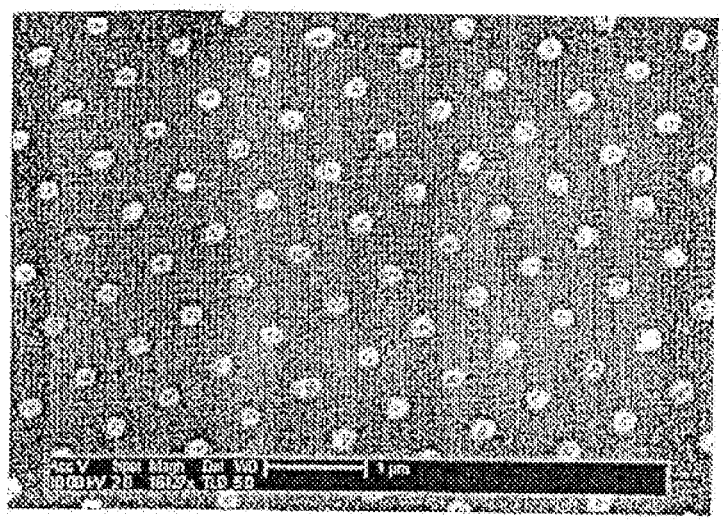
FIG. 23 is a scanning electron micrograph of 200-nm isolated trapezoidal particles of poly(lactic acid) (PLA).
Figure 24:
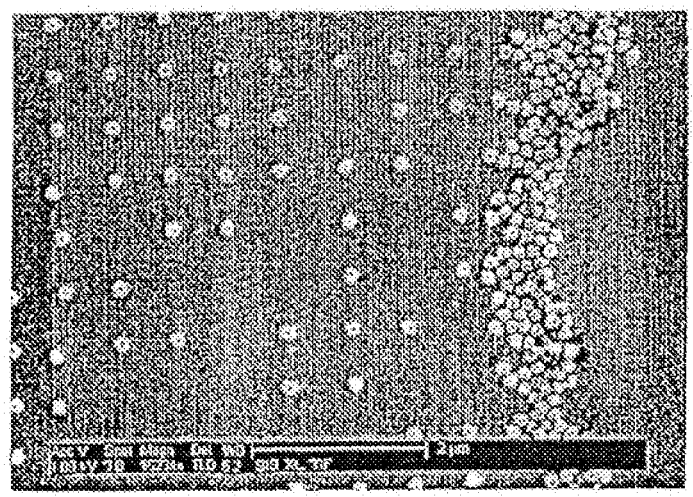
FIG. 24 is a scanning electron micrograph of 200-nm isolated trapezoidal particles of poly(lactic acid) (PLA), which have been printed using an embodiment of the presently described non-wetting imprint lithography method and harvested mechanically using a doctor blade.

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, one gram of (3S)-cis-3,6-dimethyl-1,4-dioxane-2,5-dione (LA) is heated above its melting temperature (92° C.) to 110° C. and approximately 20 μL of stannous octoate catalyst/initiator is added to the liquid monomer. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 μL of molten LA containing catalyst is then placed on the treated silicon wafer preheated to 110° C. and the patterned PFPE mold is placed on top of it. The substrate is then placed in a molding apparatus and a small pressure is applied to push out excess monomer. The entire apparatus is then placed in an oven at 110° C. for 15 hours. Particles are observed after cooling to room temperature and separation of the PFPE mold and the treated silicon wafer using scanning electron microscopy (SEM) (see FIG. 23). Further, FIG. 24 is a scanning electron micrograph of 200-nm isolated trapezoidal particles of poly(lactic acid) (PLA), which have been printed using an embodiment of the presently described non-wetting imprint lithography method and harvested mechanically using a doctor blade. The ability to harvest particles in such a way offers conclusive evidence for the absence of a "scum layer."

3.9 Fabrication of 3-μm Arrow-Shaped (PLA) Particles

Figure 25:
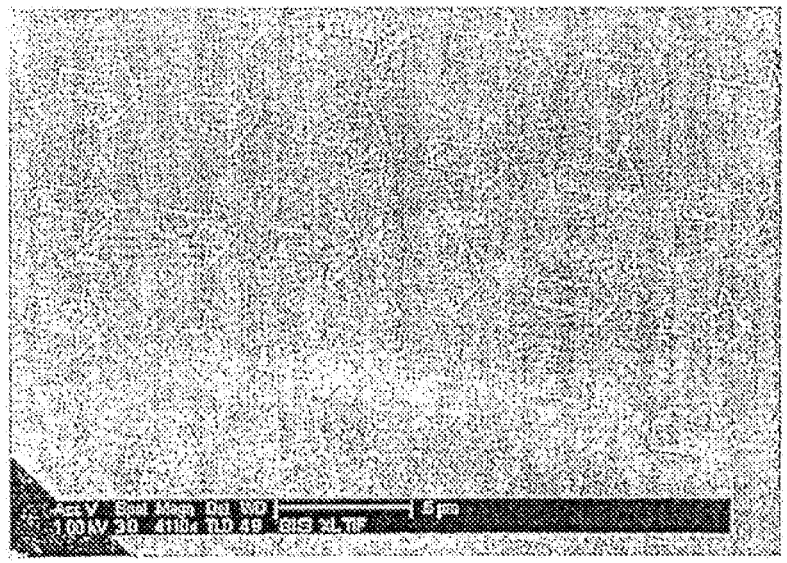
FIG. 25 is a scanning electron micrograph of 3-μm isolated arrow-shaped particles of PLA.

A patterned perfluoropolyether (PFPE) mold is generated by pouring a PFPE-dimethacrylate (PFPE-DMA) containing 1-hydroxycyclohexyl phenyl ketone over a silicon substrate patterned with 3-μm arrow shapes (see FIG. 17). A poly (dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, one gram of (3S)-cis-3,6-dimethyl-1,4-dioxane-2,5-dione (LA) is heated above its melting temperature (92° C.) to 110° C. and approximately 20 μL of stannous octoate catalyst/initiator is added to the liquid monomer. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 μL of molten LA containing catalyst is then placed on the treated silicon wafer preheated to 110° C. and the patterned PFPE mold is placed on top of it. The substrate is then placed in a molding apparatus and a small pressure is applied to push out excess monomer. The entire apparatus is then placed in an oven at 110° C. for 15 hours. Particles are observed after cooling to room temperature and separation of the PFPE mold and the treated silicon wafer using scanning electron microscopy (SEM) (see FIG. 25).

3.10 Fabrication of 500-nm Conical Shaped (PLA Particles

Figure 26:
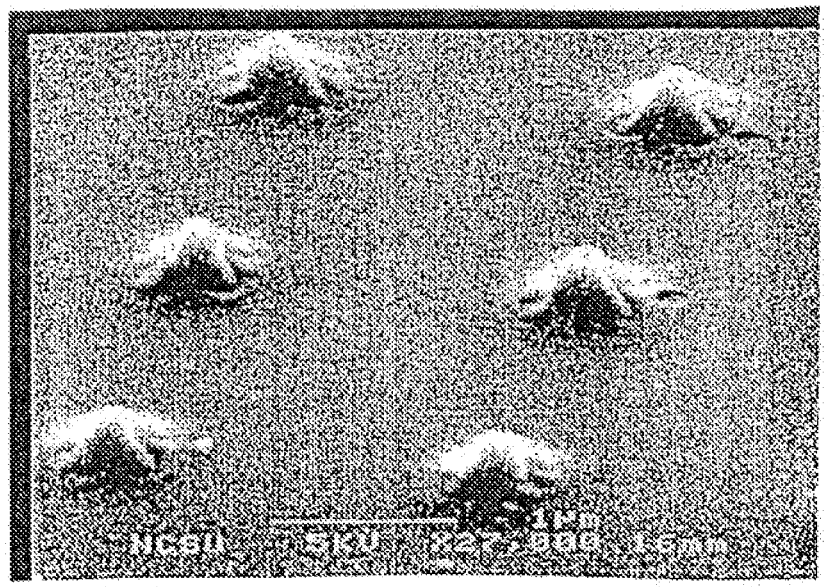
FIG. 26 is a scanning electron micrograph of 500-nm isolated conical-shaped particles of PLA.

A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 15). A poly (dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, one gram of (3S)-cis-3,6-dimethyl-1,4-dioxane-2,5-dione (LA) is heated above its melting temperature (92° C.) to 110° C. and approximately 20 μL of stannous octoate catalyst/initiator is added to the liquid monomer. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 μL of molten LA containing catalyst is then placed on the treated silicon wafer preheated to 110° C. and the patterned PFPE mold is placed on top of it. The substrate is then placed in a molding apparatus and a small pressure is applied to push out excess monomer. The entire apparatus is then placed in an oven at 110° C. for 15 hours. Particles are observed after cooling to room temperature and separation of the PFPE mold and the treated silicon wafer using scanning electron microscopy (SEM) (see FIG. 26).

3.11 Fabrication of 200-nm Trapezoidal Poly(Pyrrole) (Ppy) Particles

Figure 27:
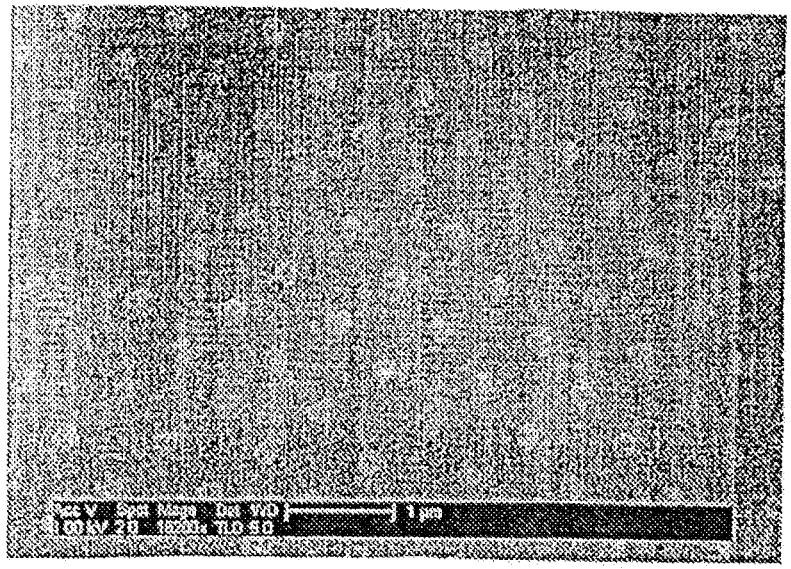
FIG. 27 is a scanning electron micrograph of 200-nm isolated trapezoidal particles of poly(pyrrole) (Ppy).

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Separately, 50 μL of a 1:1 v:v solution of tetrahydrofuran:pyrrole is added to 50 μL of 70% perchloric acid (aq). A clear, homogenous, brown solution quickly forms and develops into black, solid, polypyrrole in 15 minutes. A drop of this clear, brown solution (prior to complete polymerization) is placed onto a treated silicon wafer and into a stamping apparatus and a pressure is applied to remove excess solution. The apparatus is then placed into a vacuum oven for 15 h to remove the THF and water. Particles are observed using scanning electron microscopy (SEM) (see FIG. 27) after release of the vacuum and separation of the PFPE mold and the treated silicon wafer.

3.12 Fabrication of 3-μm Arrow-Shaped (Ppy) Particles

Figure 28:
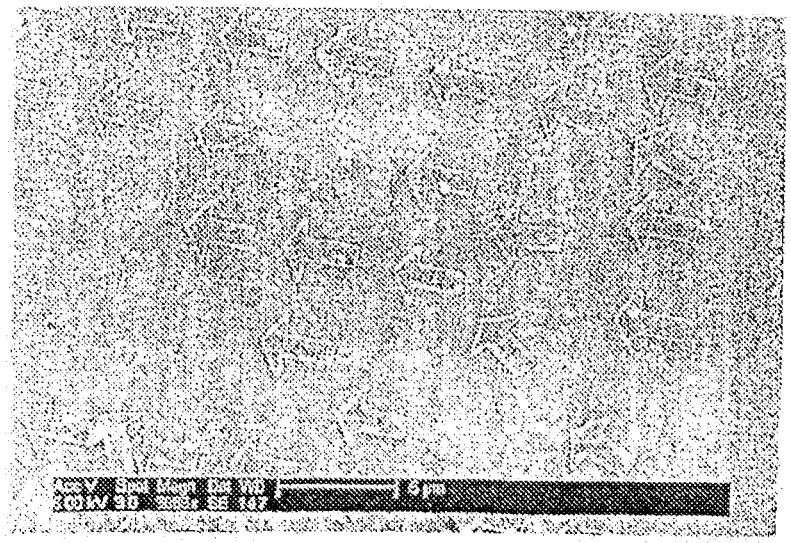
FIG. 28 is a scanning electron micrograph of 3-μm arrow-shaped Ppy particles.

A patterned perfluoropolyether (PFPE) mold is generated by pouring a PFPE-dimethacrylate (PFPE-DMA) containing 1-hydroxycyclohexyl phenyl ketone over a silicon substrate patterned with 3-μm arrow shapes (see FIG. 17). A poly (dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Separately, 50 μL of a 1:1 v:v solution of tetrahydrofuran:pyrrole is added to 50 μL of 70% perchloric acid (aq). A clear, homogenous, brown solution quickly forms and develops into black, solid, polypyrrole in 15 minutes. A drop of this clear, brown solution (prior to complete polymerization) is placed onto a treated silicon wafer and into a stamping apparatus and a pressure is applied to remove excess solution. The apparatus is then placed into a vacuum oven for 15 h to remove the THF and water. Particles are observed using scanning electron microscopy (SEM) (see FIG. 28) after release of the vacuum and separation of the PFPE mold and the treated silicon wafer.

3.13 Fabrication of 500-nm Conical (Ppy) Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 15). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Separately, 50 μL of a 1:1 v:v solution of tetrahydrofuran:pyrrole is added to 50 μL of 70% perchloric acid (aq). A clear, homogenous, brown solution quickly forms and develops into black, solid, polypyrrole in 15 minutes. A drop of this clear, brown solution (prior to complete polymerization) is placed onto a treated silicon wafer and into a stamping apparatus and a pressure is applied to remove excess solution. The apparatus is then placed into a vacuum oven for 15 h to remove the THF and water. Particles are observed using scanning electron microscopy (SEM) (see FIG. 29) after release, of the vacuum and separation of the PFPE mold and the treated silicon wafer.

3.14 Encapsulation of Fluorescently Tagged DNA Inside 200-nm Trapezoidal PEG Particles A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. 20 μL of water and 20 μL of PEG diacrylate monomer are added to 8 nanomoles of 24 bp DNA oligonucleotide that has been tagged with a fluorescent dye, CY-3. Flat, uniform, non-wetting surfaces are generated by treating a silicon wafer cleaned with "piranha" solution (1:1 concentrated sulfuric acid: 30% hydrogen peroxide (aq) solution) with trichloro (1H, 1H, 2H, 2H-perfluorooctyl) silane via vapor deposition in a desiccator for 20 minutes. Following this, 50 μL of the PEG diacrylate solution is then placed on the treated silicon wafer and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for ten minutes while under a nitrogen purge. Particles are observed after separation of the PFPE mold and the treated silicon wafer using confocal fluorescence microscopy (see FIG. 30). Further, FIG. 30A shows a fluorescent confocal micrograph of 200-nm trapezoidal PEG nanoparticles, which contain 24-mer DNA strands that are tagged with CY-3. FIG. 30B is optical micrograph of the 200-nm isolated trapezoidal particles of PEG diacrylate that contain fluorescently tagged DNA. FIG. 30C is the overlay of the images provided in FIGS. 30A and 30B, showing that every particle contains DNA.

3.15 Encapsulation of Magnetite Nanoparticles Inside 500-nm Conical PEG Particles A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 15). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Separately, citrate capped magnetite nanoparticles were synthesized by reaction of ferric chloride (40 mL of a 1 M aqueous solution) and ferrous chloride (10 mL of a 2 M aqueous hydrochloric acid solution) which is added to ammonia (500 mL of a 0.7 M aqueous solution). The resulting precipitate is collected by centrifugation and then stirred in 2 M perchloric acid. The final solids are collected by centrifugation. 0.290 g of these perchlorate-stabilized nanoparticles are suspended in 50 mL of water and heated to 90° C. while stirring. Next, 0.106 g of sodium citrate is added. The solution is stirred at 90° C. for 30 min to yield an aqueous solution of citrate-stabilized iron oxide nanoparticles. 50 μL of this solution is added to 50 μL of a PEG diacrylate solution in a microtube. This microtube is vortexed for ten seconds. Following this, 50 μL of this PEG diacrylate/particle solution is then placed on the treated silicon wafer and the patterned PFPE mold placed on top of it. The substrate is then placed in a molding apparatus and a small pressure is applied to push out excess PEG-diacrylate/particle solution. The entire apparatus is then subjected to UV light ($\lambda$=365 nm) for ten minutes while under a nitrogen purge. Nanoparticle-containing PEG-diacrylate particles are observed after separation of the PFPE mold and the treated silicon wafer using optical microscopy.

3.16 Fabrication of Isolated Particles on Glass Surfaces Using "Double stamping"

Figure 31:
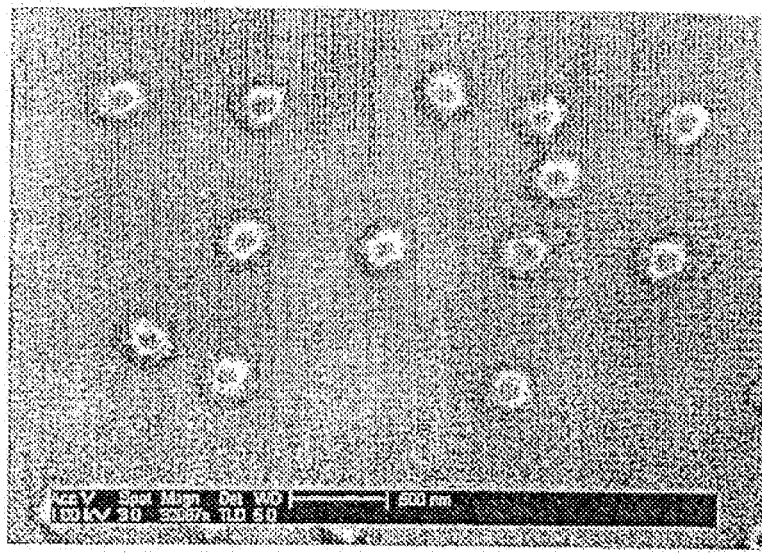
FIG. 31 is a scanning electron micrograph of fabrication of 200-nm PEG-diacrylate nanoparticles using "double stamping."

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. A flat, non-wetting surface is generated by photocuring a film of PFPE-DMA onto a glass slide, according to the procedure outlined for generating a patterned PFPE-DMA mold. 5 μL of the PEG-diacrylate/photoinitiator solution is pressed between the PFPE-DMA mold and the flat PFPE-DMA surface, and pressure is applied to squeeze out excess PEG-diacrylate monomer. The PFPE-DMA mold is then removed from the flat PFPE-DMA surface and pressed against a clean glass microscope slide and photocured using UV radiation ($\lambda$=365 nm) for 10 minutes while under a nitrogen purge. Particles are observed after cooling to room temperature and separation of the PFPE mold and the glass microscope slide, using scanning electron microscopy (SEM) (see FIG. 31).

3.17. Encapsulation of Viruses in PEG-Diacrylate Nanoparticles.

A patterned perfluoropolyether (PFPE) mold is generated by pouring PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Fluorescently-labeled or unlabeled Adenovirus or Adeno-Associated Virus suspensions are added to this PEG-diacrylate monomer solution and mixed thoroughly. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 µL of the PEG diacrylate/virus solution is then placed on the treated silicon wafer and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for ten minutes while under a nitrogen purge. Virus-containing particles are observed after separation of the PFPE mold and the treated silicon wafer using transmission electron microscopy or, in the case of fluorescently-labeled viruses, confocal fluorescence microscopy.

3.18 Encapsulation of Proteins in PEG-Diacrylate Nanoparticles.

A patterned perfluoropolyether (PFPE) mold is generated by pouring PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Fluorescently-labeled or unlabeled protein solutions are added to this PEG-diacrylate monomer solution and mixed thoroughly. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 µL of the PEG diacrylate/virus solution is then placed on the treated silicon wafer and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for ten minutes while under a nitrogen purge. Protein-containing particles are observed after separation of the PFPE mold and the treated silicon wafer using traditional assay methods or, in the case of fluorescently-labeled proteins, confocal fluorescence microscopy.

3.19 Fabrication of 200-nm Titania Particles

A patterned perfluoropolyether (PFPE) mold can be generated by pouring a PFPE-dimethacrylate (PFPE-DMA) containing 1-hydroxycyclohexyl phenyl ketone over a silicon substrate patterned with 200-nm trapezoidal shapes, such as shown in FIG. 13. A poly(dimethylsiloxane) mold can be used to confine the liquid PFPE-DMA to the desired area. The apparatus can then be subjected to UV light ($\lambda$=365 nm) for 10 minutes while under a nitrogen purge. The fully cured PFPE-DMA mold is then released from the silicon master. Separately, 1 g of Pluronic P123 is dissolved in 12 g of absolute ethanol. This solution was added to a solution of 2.7 mL of concentrated hydrochloric acid and 3.88 mL titanium (IV) ethoxide. Flat, uniform, non-wetting surfaces can be generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 µL of the sol-gel solution can then be placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. After solidification of the sol-gel precursor, the silicon wafer can be removed from the patterned PFPE and particles will be present.

3.20 Fabrication of 200-nm Silica Particles

A patterned perfluoropolyether (PFPE) mold can be generated by pouring a PFPE-dimethacrylate (PFPE-DMA) containing 1-hydroxycyclohexyl phenyl ketone over a silicon substrate patterned with 200-nm trapezoidal shapes, such as shown in FIG. 13. A poly(dimethylsiloxane) mold can then be used to confine the liquid PFPE-DMA to the desired area. The apparatus can then be subjected to UV light ($\lambda$=365 nm) for 10 minutes while under a nitrogen purge. The fully cured PFPE-DMA mold is then released from the silicon master. Separately, 2 g of Pluronic P123 is dissolved in 30 g of water and 120 g of 2 M HCl is added while stirring at 35° C. To this solution, add 8.50 g of TEOS with stirring at 35° C. for 20 h. Flat, uniform, non-wetting surfaces can be generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. Particles should be observed after separation of the PFPE mold and the treated silicon wafer using scanning electron microscopy (SEM).

3.21 Fabrication of 200-nm Europium-Doped Titania Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 1 g of Pluronic P123 and 0.51 g of $EuCl_3.6H_2O$ are dissolved in 12 g of absolute ethanol. This solution is added to a solution of 2.7 mL of concentrated hydrochloric acid and 3.88 mL titanium (IV) ethoxide. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. Next, after the sol-gel precursor has solidified, the PFPE mold and the treated silicon wafer are separated and particles should be observed using scanning electron microscopy (SEM).

3.22 Encapsulation of CdSe Nanoparticles Inside 200-nm PEG Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Separately, 0.5 g of sodium citrate and 2 mL of 0.04 M cadmium perchlorate are dissolved in 45 mL of water, and the pH is adjusted to of the solution to 9 with 0.1 M NaOH. The solution is bubbled with nitrogen for 15 minutes. 2 mL of 1 M N,N-dimethylselenourea is added to the solution and heated in a microwave oven for 60 seconds. 50 µL of this solution is added to 50 µL of a PEG diacrylate solution in a microtube. This microtube is vortexed for ten seconds. 50 µL of this PEG diacrylate/CdSe particle solution is placed on the treated silicon wafer and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for ten minutes while under a nitrogen purge. PEG-diacrylate particles with encapsulated CdSe nanoparticles will be observed after separation of the PFPE mold and the treated silicon wafer using TEM or fluorescence microscopy.

3.23 Synthetic Replication of Adenovirus Particles Using Non-Wetting Imprint Lithography A template, or "master," for perfluoropolyether-dimethacrylate (PFPE-DMA) mold fabrication is generated by dispersing adenovirus particles on a silicon wafer. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro (1H, 1H, 2H, 2H-perfluorooctyl) silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light ($\lambda$=365 nm) for ten minutes while under a nitrogen purge. Synthetic virus replicates are observed after separation of the PFPE mold and the treated silicon wafer using scanning electron microscopy (SEM) or transmission electron microscopy (TEM).

3.24 Synthetic Replication Of Earthworm Hemoglobin Protein Using Non-Wetting Imprint Lithography A template, or "master," for perfluoropolyether-dimethacrylate (PFPE-DMA) mold fabrication is generated by dispersing earthworm hemoglobin protein on a silicon wafer. This master can be used to template a patterned mold by pouring PFPE-DMA containing 1-hydroxycyclohexyl phenyl ketone over the patterned area of the master. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light ($\lambda$=365 nm) for ten minutes while under a nitrogen purge. Synthetic protein replicates are observed after separation of the PFPE mold and the treated silicon wafer using scanning electron microscopy (SEM) or transmission electron microscopy (TEM).

3.25 Combinatorial Engineering of 100-nm Nanoparticle Therapeutics

A patterned perfluoropolyether (PFPE) mold is generated by pouring a PFPE-dimethacrylate (PFPE-DMA) containing 1-hydroxycyclohexyl phenyl ketone over a silicon substrate patterned with 100-nm cubic shapes. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Other therapeutic agents (i.e., small molecule drugs, proteins, polysaccharides, DNA, etc.), tissue targeting agents (cell penetrating peptides and ligands, hormones, antibodies, etc.), therapeutic release/transfection agents (other controlled-release monomer formulations, cationic lipids, etc.), and miscibility enhancing agents (cosolvents, charged monomers, etc.) are added to the polymer precursor solution in a combinatorial manner. Flat, uniform, non-wetting surfaces are generated by treating a silicon wafer cleaned with "piranha" solution (1:1 concentrated sulfuric acid:30% hydrogen peroxide (aq) solution) with trichloro (1H, 1H, 2H, 2H-perfluorooctyl) silane via vapor deposition in a desiccator for 20 minutes. Following this, 50 µL of the combinatorially-generated particle precursor solution is then placed on the treated silicon wafer and the patterned PFPE mold placed on top of it. The substrate is then placed in a molding apparatus and a small pressure is applied to push out excess solution. The entire apparatus is then subjected to UV light ($\lambda$=365 nm) for ten minutes while under a nitrogen purge. The PFPE-DMA mold is then separated from the treated wafer, particles can be harvested, and the therapeutic efficacy of each combinatorially generated nanoparticle is established. By repeating this methodology with different particle formulations, many combinations of therapeutic agents, tissue targeting agents, release agents, and other important compounds can be rapidly screened to determine the optimal combination for a desired therapeutic application.

3.26 Fabrication of a Shape-Specific PEG Membrane

A patterned perfluoropolyether (PFPE) mold is generated by pouring a PFPE-dimethacrylate (PFPE-DMA) containing 1-hydroxycyclohexyl phenyl ketone over a silicon substrate patterned with 3-µm cylindrical holes that are 5 µm deep. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro(1H, 1H, 2H, 2H-perfluorooctyl) silane via vapor deposition in a desiccator for 20 minutes. Following this, 50 µL of PEG diacrylate is then placed on the treated silicon wafer and the patterned PFPE mold placed on top of it. The substrate is then placed in a molding apparatus and a small pressure is applied to push out excess PEG-diacrylate. The entire apparatus is then subjected to UV light ($\lambda$=365 nm) for ten minutes while under a nitrogen purge. An interconnected membrane will be observed after separation of the PFPE mold and the treated silicon wafer using scanning electron microscopy (SEM). The membrane will release from the surface by soaking in water and allowing it to lift off the surface.

3.27 Harvesting of PEG Particles by Ice Formation

A patterned perfluoropolyether (PFPE) mold is generated by pouring a PFPE-dimethacrylate (PFPE-DMA) containing 1-hydroxycyclohexyl phenyl ketone over a silicon substrate patterned with 5-µm cylinder shapes. The substrate is then subjected to a nitrogen purge for 10 minutes, then UV light ($\lambda$=365 nm) is applied for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by coating a glass slide with PFPE-DMA containing 1-hydroxycyclohexyl phenyl ketone. The slide is then subjected to a nitrogen purge for 10 minutes, then UV light ($\lambda$=365 nm) is applied for 10 minutes while under a nitrogen purge. The flat, fully cured PFPE-DMA substrate is released from the slide. Following this, 0.1 mL of PEG diacrylate is then placed on the flat PFPE-DMA substrate and the patterned PFPE mold placed on top of it. The substrate is then placed in a molding apparatus and a small pressure is applied to push out excess PEG-diacrylate. The entire apparatus is then purged with nitrogen for 10 minutes, then subjected to UV light ($\lambda$=365 nm) for 10 minutes while under a nitrogen purge. PEG particles are observed after separation of the PFPE-DMA mold and substrate using optical microscopy. Water is applied to the surface of the substrate and mold containing particles. A gasket is used to confine the water to the desired location. The apparatus is then placed in the freezer at a temperature of −10° C. for 30 minutes. The ice containing PEG particles is peeled off the PFPE-DMA mold and substrate and allowed to melt, yielding an aqueous solution containing PEG particles.

3.28 Harvesting of PEG Particles with Vinyl Pyrrolidone

A patterned perfluoropolyether (PFPE) mold is generated by pouring a PFPE-dimethacrylate (PFPE-DMA) containing 1-hydroxycyclohexyl phenyl ketone over a silicon substrate patterned with 5-µm cylinder shapes. The substrate is then subjected to a nitrogen purge for 10 minutes, and then UV light ($\lambda$=365 nm) is applied for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by coating a glass slide with PFPE-DMA containing 1-hydroxycyclohexyl phenyl ketone. The slide is then subjected to a nitrogen purge for 10 minutes, then UV light ($\lambda$=365 nm) is applied for 10 minutes while under a nitrogen purge. The flat, fully cured PFPE-DMA substrate is released from the slide. Following this, 0.1 mL of PEG diacrylate is then placed on the flat PFPE-DMA substrate and the patterned PFPE mold placed on top of it. The substrate is then placed in a molding apparatus and a small pressure is applied to push out excess PEG-diacrylate. The entire apparatus is then purged with nitrogen for 10 minutes, then subjected to UV light ($\lambda$=365 nm) for 10 minutes while under a nitrogen purge. PEG particles are observed after separation of the PFPE-DMA mold and substrate using optical microscopy. In some embodiments, the material includes an adhesive or sticky surface. In some embodiments, the material includes carbohydrates, epoxies, waxes, polyvinyl alcohol, polyvinyl pyrrolidone, polybutyl acrylate, polycyano acrylates, polymethyl methacrylate. In some embodiments, the harvesting or collecting of the particles includes cooling water to form ice (e.g., in contact with the particles) drop of n-vinyl-2-pyrrolidone containing 5% photoinitiator, 1-hydroxycyclohexyl phenyl ketone, is placed on a clean glass slide. The PFPE-DMA mold containing particles is placed patterned side down on the n-vinyl-2-pyrrolidone drop. The slide is subjected to a nitrogen purge for 5 minutes, then UV light ($\lambda$=365 nm) is applied for 5 minutes while under a nitrogen purge. The slide is removed, and the mold is peeled away from the polyvinyl pyrrolidone and particles. Particles on the polyvinyl pyrrolidone were observed with optical microscopy. The polyvinyl pyrrolidone film containing particles was dissolved in water. Dialysis was used to remove the polyvinyl pyrrolidone, leaving an aqueous solution containing 5 µm PEG particles.

3.29 Harvesting of PEG Particles with Polyvinyl Alcohol

A patterned perfluoropolyether (PFPE) mold is generated by pouring a PFPE-dimethacrylate (PFPE-DMA) containing 1-hydroxycyclohexyl phenyl ketone over a silicon substrate patterned with 5-µm cylinder shapes. The substrate is then subjected to a nitrogen purge for 10 minutes, then UV light ($\lambda$=365 nm) is applied for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by coating a glass slide with PFPE-DMA containing 1-hydroxycyclohexyl phenyl ketone. The slide is then subjected to a nitrogen purge for 10 minutes, then UV light ($\lambda$=365 nm) is applied for 10 minutes while under a nitrogen purge. The flat, fully cured PFPE-DMA substrate is released from the slide. Following this, 0.1 mL of PEG diacrylate is then placed on the flat PFPE-DMA substrate and the patterned PFPE mold placed on top of it. The substrate is then placed in a molding apparatus and a small pressure is applied to push out excess PEG-diacrylate. The entire apparatus is then purged with nitrogen for 10 minutes, then subjected to UV light (λ=365 nm) for 10 minutes while under a nitrogen purge. PEG particles are observed after separation of the PFPE-DMA mold and substrate using optical microscopy. Separately, a solution of 5 weight percent polyvinyl alcohol (PVOH) in ethanol (EtOH) is prepared. The solution is spin coated on a glass slide and allowed to dry. The PFPE-DMA mold containing particles is placed patterned side down on the glass slide and pressure is applied. The mold is then peeled away from the PVOH and particles. Particles on the PVOH were observed with optical microscopy. The PVOH film containing particles was dissolved in water. Dialysis was used to remove the PVOH, leaving an aqueous solution containing 5 μm PEG particles.

3.30 Fabrication of 200 Nm Phosphatidylcholine Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to a nitrogen purge for 10 minutes followed by UV light (λ=365 nm) for 10 minutes while under a nitrogen purge. The fully cured PFPE-DMA mold is then released from the silicon master. Separately, flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Following this, 20 mg of the phosphatidylcholine was placed on the treated silicon wafer and heated to 60 degrees C. The substrate is then placed in a molding apparatus and a small pressure is applied to push out excess phosphatidylcholine. The entire apparatus is then set aside until the phosphatidylcholine has solidified. Particles are observed after separation of the PFPE mold and the treated silicon wafer using scanning electron microscopy (SEM).

3.31 Functionalizing PEG Particles with FITC

Poly(ethylene glycol) (PEG) particles with 5 weight percent aminoethyl methacrylate were created. Particles are observed in the PFPE mold after separation of the PFPE mold and the PFPE substrate using optical microscopy. Separately, a solution containing 10 weight percent fluorescein isothiocyanate (FITC) in dimethylsulfoxide (DMSO) was created. Following this, the mold containing the particles was exposed to the FITC solution for one hour. Excess FITC was rinsed off the mold surface with DMSO followed by deionized (DI) water. The tagged particles were observed with fluorescence microscopy, with an excitation wavelength of 492 nm and an emission wavelength of 529 nm.

3.32 Encapsulation of Doxorubicin Inside 500 nm Conical PEG Particles

Figure 32:
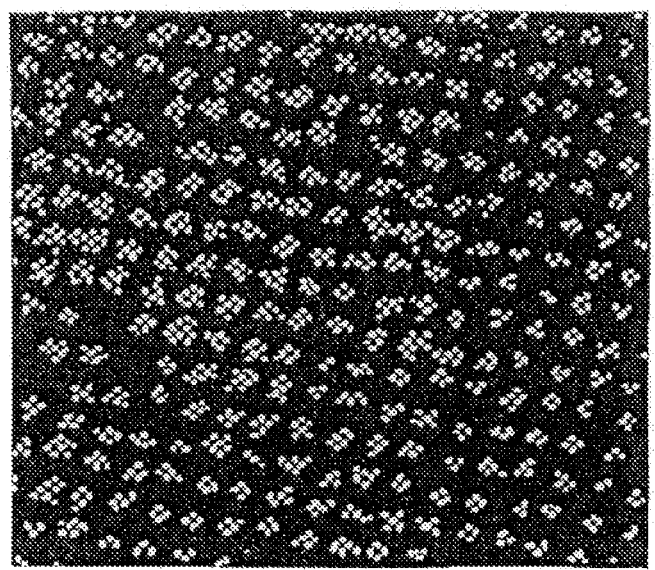
FIG. 32 shows doxorubicin containing particles after removal from a template according to an embodiment of the presently disclosed subject matter.

A patterned perfluoropolyether (PFPE) mold was generated by pouring a PFPE-dimethacrylate (PFPE-DMA) containing 1-hydroxycyclohexyl phenyl ketone over a silicon substrate patterned with 500-nm conical shapes (see FIG. 15). A poly(dimethylsiloxane) mold was used to confine the liquid PFPE-DMA to the desired area. The apparatus was then subjected to UV light (λ=365 nm) for 10 minutes while under a nitrogen purge. The fully cured PFPE-DMA mold was then released from the silicon master. Flat, uniform, non-wetting surfaces were generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Separately, a solution of 1 wt % doxorubicin in PEG diacrylate was formulated with 1 wt % photoinitiator. Following this, 50 μL of this PEG diacrylate/doxorubicin solution was then placed on the treated silicon wafer and the patterned PFPE mold placed on top of it. The substrate was then placed in a molding apparatus and a small pressure was applied to push out excess PEG-diacrylate/doxorubicin solution. The small pressure in this example was at least about 100 N/cm². The entire apparatus was then subjected to UV light (λ=365 nm) for ten minutes while under a nitrogen purge. Doxorubicin-containing PEG-diacrylate particles were observed after separation of the PFPE mold and the treated silicon wafer using fluorescent microscopy (see FIG. 32).

3.33 Encapsulation of Avidin (66 kDa) in 160 nm PEG Particles

Figure 33:
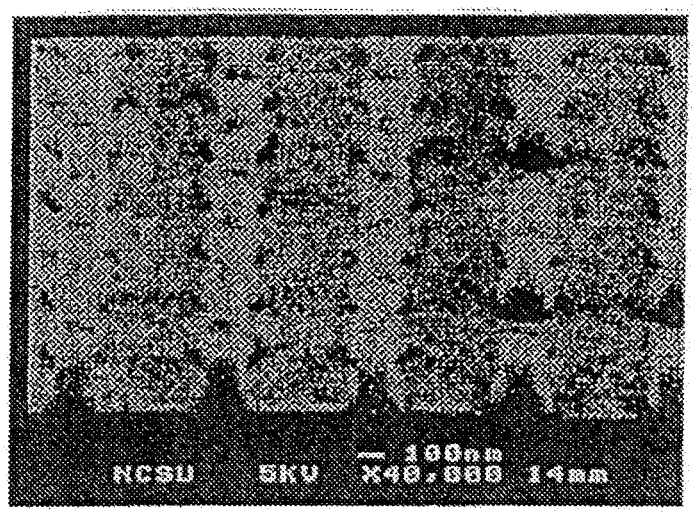
FIG. 33 shows a structure patterned with nano-cylindrical shapes according to an embodiment of the presently disclosed subject matter.

A patterned perfluoropolyether (PFPE) mold was generated by pouring a PFPE-dimethacrylate (PFPE-DMA) containing 1-hydroxycyclohexyl phenyl ketone over a silicon substrate patterned with 160-nm cylindrical shapes (see FIG. 33). A poly(dimethylsiloxane) mold was used to confine the liquid PFPE-DMA to the desired area. The apparatus was then subjected to UV light (λ=365 nm) for 10 minutes white under a nitrogen purge. The fully cured PFPE-DMA mold was then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro (1H, 1H, 2H, 2H-perfluorooctyl) silane via vapor deposition in a desiccator for 20 minutes. Separately, a solution of 1 wt % avidin in 30:70 PEG monomethacrylate:PEG diacrylate was formulated with 1 wt % photoinitiator. Following this, 50 μL of this PEG/avidin solution was then placed on the treated silicon wafer and the patterned PFPE mold placed on top of it. The substrate was then placed in a molding apparatus and a small pressure is applied to push out excess PEG-diacrylate/avidin solution. The small pressure in this example was at least about 100 N/cm². The entire apparatus was then subjected to UV light (λ=365 nm) for ten minutes while under a nitrogen purge. Avidin-containing PEG particles were observed after separation of the PFPE mold and the treated silicon wafer using fluorescent microscopy.

3.34 Encapsulation of 2-fluoro-2-deoxy-d-glucose in 80 nm PEG Particles

A patterned perfluoropolyether (PFPE) mold is generated by pouring a PFPE-dimethacrylate (PFPE-DMA) containing 1-hydroxycyclohexyl phenyl ketone over a 6 inch silicon substrate patterned with 80-nm cylindrical shapes. The substrate is then subjected to UV light (λ=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro (1H, 1H, 2H, 2H-perfluorooctyl) silane via vapor deposition in a desiccator for 20 minutes. Separately, a solution of 0.5 wt % 2-fluoro-2-deoxy-d-glucose (FDG) in 30:70 PEG monomethacrylate:PEG diacrylate is formulated with 1 wt % photoinitiator. Following this, 200 μL of this PEG/FDG solution is then placed on the treated silicon wafer and the patterned PFPE mold placed on top of it. The substrate is then placed in a molding apparatus and a small pressure is applied to push out excess PEG/FDG solution. The small pressure should be at least about 100 N/cm². The entire apparatus is then subjected to UV light (λ=365' nm) for ten minutes while under a nitrogen purge. FDG-containing PEG particles will be observed after separation of the PFPE mold and the treated silicon wafer using scanning electron microscopy.

3.35 Encapsulated DNA in 200 nm×200 nm×1 μm Bar-Shaped Poly(Lactic Acid) Particles A patterned perfluoropolyether (PFPE) mold is generated by pouring a PFPE-dimethacrylate (PFPE-DMA) containing 1-hydroxycyclohexyl phenyl ketone over a silicon substrate patterned with 200 nm×200 nm×1 μm bar shapes. The substrate is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro (1H, 1H, 2H, 2H-perfluorooctyl) silane via vapor deposition in a desiccator for 20 minutes. Separately, a solution of 0.01 wt % 24 base pair DNA and 5 wt % poly(lactic acid) in ethanol is formulated. 200 μL of this ethanol solution is then placed on the treated silicon wafer and the patterned PFPE mold placed on top of it. The substrate is then placed in a molding apparatus and a small pressure is applied to push out excess PEG/FDG solution. The small pressure should be at least about 100 N/cm$^2$. The entire apparatus is then placed under vacuum for 2 hours. DNA-containing poly(lactic acid) particles will be observed after separation of the PFPE mold and the treated silicon wafer using optical microscopy.

3.36 100 nm Paclitaxel Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 15). A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Separately, a solution of 5 wt % paclitaxel in ethanol was formulated. Following this, 100 μL of this paclitaxel solution is then placed on the treated silicon wafer and the patterned PFPE mold placed on top of it. The substrate is then placed in a molding apparatus and a small pressure is applied to push out excess solution. The pressure applied was at least about 100 N/cm$^2$. The entire apparatus is then placed under vacuum for 2 hours. Separation of the mold and surface yielded approximately 100 nm spherical paclitaxel particles, which were observed with scanning electron microscopy.

3.37 Triangular Particles Functionalized on One Side

A patterned perfluoropolyether (PFPE) mold is generated by pouring a PFPE-dimethacrylate (PFPE-DMA) containing 1-hydroxycyclohexyl phenyl ketone over a 6 inch silicon substrate patterned with 0.6 μm×0.8 μm×1 μm right triangles. The substrate is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Separately, a solution of 5 wt % aminoethyl methacrylate in 30:70 PEG monomethacrylate:PEG diacrylate is formulated with 1 wt % photoinitiator. Following this, 200 μL of this monomer solution is then placed on the treated silicon wafer and the patterned PFPE mold placed on top of it. The substrate is then placed in a molding apparatus and a small pressure is applied to push out excess solution. The small pressure should be at least about 100 N/cm$^2$. The entire apparatus is then subjected to UV light ($\lambda$=365 nm) for ten minutes while under a nitrogen purge. Aminoethyl methacrylate-containing PEG particles are observed in the mold after separation of the PFPE mold and the treated silicon wafer using optical microscopy. Separately, a solution containing 10 weight percent fluorescein isothiocyanate (FITC) in dimethylsulfoxide (DMSO) is created. Following this, the mold containing the particles is exposed to the FITC solution for one hour. Excess FITC is rinsed off the mold surface with DMSO followed by deionized (DI) water. Particles, tagged only on one face, will be observed with fluorescence microscopy, with an excitation wavelength of 492 nm and an emission wavelength of 529 nm.

3.38 Formation of an Imprinted Protein Binding Cavity and an Artificial Protein.

The desired protein molecules are adsorbed onto a mica substrate to create a master template. A mixture of PFPE-dimethacrylate (PFPE-DMA) containing a monomer with a covalently attached disaccharide, and 1-hydroxycyclohexyl phenyl ketone as a photoinitiator was poured over the substrate. The substrate is then subjected to UV light ($\lambda$=365 nm) for 10 minutes while under a nitrogen purge. The fully cured PFPE-DMA mold is then released from the mica master, creating polysaccharide-like cavities that exhibit selective recognition for the protein molecule that was imprinted. The polymeric mold was soaked in NaOH/NaClO solution to remove the template proteins.

Flat, uniform, non-wetting surfaces are generated by treating a silicon wafer cleaned with "piranha" solution (1:1 concentrated sulfuric acid: 30% hydrogen peroxide (aq) solution) with trichloro(1H, 1H, 2H, 2H-perfluorooctyl) silane via vapor deposition in a desiccator for 20 minutes. Separately, a solution of 25% (w/w) methacrylic acid (MAA), 25% diethyl aminoethylmethacrylate (DEAEM), and 48% PEG diacrylate was formulated with 2 wt % photoinitiator. Following this, 200 μL of this monomer solution is then placed on the treated silicon wafer and the patterned PFPE/disaccharide mold placed on top of it. The substrate is then placed in a molding apparatus and a small pressure is applied to push out excess solution. The entire apparatus is then subjected to UV light ($\lambda$=365 nm) for ten minutes while under a nitrogen purge. Removal of the mold yields artificial protein molecules which have similar size, shape, and chemical functionality as the original template protein molecule.

3.39 Template Filling with "Moving Drop"

A mold (6 inch in diameter) with 5×5×10 micron pattern was placed on an inclined surface that has an angle of 20 degrees to horizon. Then a set of 100 μL drops of 98% PEG-diacrylate and 2% photo initiator solution was placed on the surface of the mold at a higher end. Each drop then would slide down leaving the trace with filled cavities.

After all the drops reached the lower end the mold was put in UV oven, purged with nitrogen for 15 minutes and then cured for 15 minutes. The particles were harvested on glass slide using cyanoacrylate adhesive. No scum was detected and monodispersity of the particles was confirmed first using optical microscope and then scanning electron microscope.

3.40 Template Filling Through Dipping

A mold of size 0.5×3 cm with 3×3×8 micron pattern was dipped into the vial with 98% PEG-diacrylate and 2% photo initiator solution. After 30 seconds the mold was withdrawn at a rate of approximately 1 mm per second.

Then the mold was put into an UV oven, purged with nitrogen for 15 minutes, and then cured for 15 minutes. The particles were harvested on the glass slide using cyanoacrylate adhesive. No scum was detected and monodispersity of the particles was confirmed using optical microscope.

3.41 Template Filling by Voltage Assist

A voltage of about 3000 volts DC can be applied across a substance to be molded, such as PEG. The voltage makes the filling process easier as it changes the contact angle of substance on the patterned template.

3.42 Fabrication of 2 μm Cube-Shaped PEG Particles by Dipping

Figure 34A:
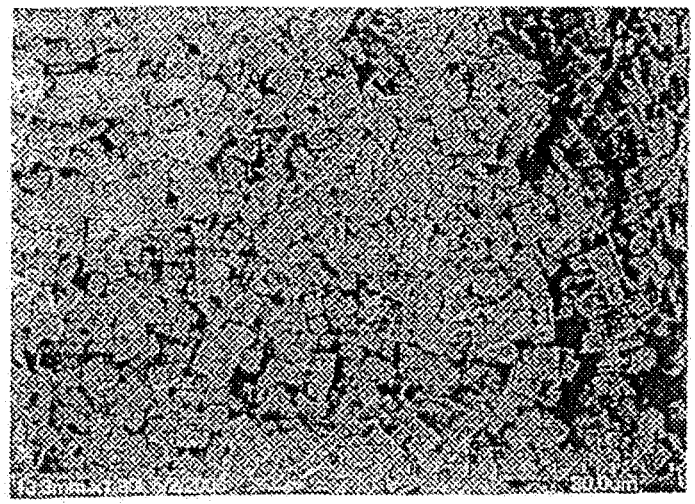
FIGS. 34A and 34B show cube-shaped PEG particles fabricated by a dipping method according to an embodiment of the present invention.
Figure 34B:
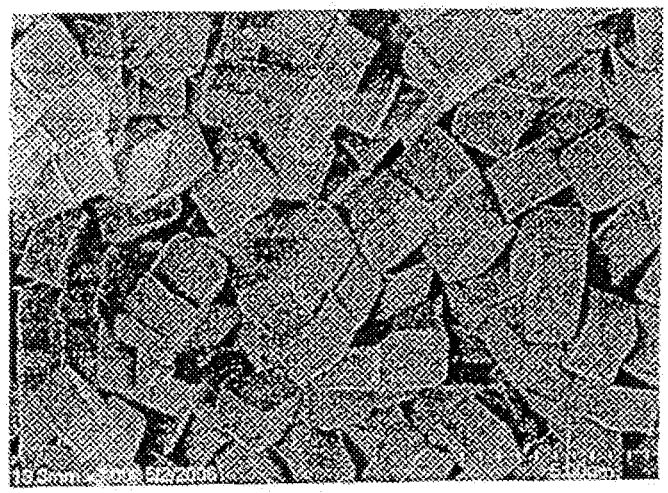

A patterned perfluoropolyether (PFPE) mold is generated by pouring a PFPE-dimethacrylate (PFPE-DMA) containing 1-hydroxycyclohexyl phenyl ketone over a silicon substrate patterned with 2-μm×2-μm×1-μm cubes. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Fluorescently-labeled methacrylate is added to this PEG-diacrylate monomer solution and mixed thoroughly. The mold is dipped into this solution and withdrawn slowly. The mold is subjected to UV light for 10 minutes under nitrogen purge. The particles are harvested by placing cyanoacrylate onto a glass slide, placing the mold in contact with the cyanoacrylate, and allowing the cyanoacrylate to cure. The mold is removed from the cured film, leaving the particles entrapped in the film. The cyanoacrylate is dissolved away using acetone, and the particles are collected in an acetone solution, and purified with centrifugation. Particles are observed using scanning electron microscopy (SEM) after drying (see FIGS. 34A and 34B).

Example 4

Figure 35:
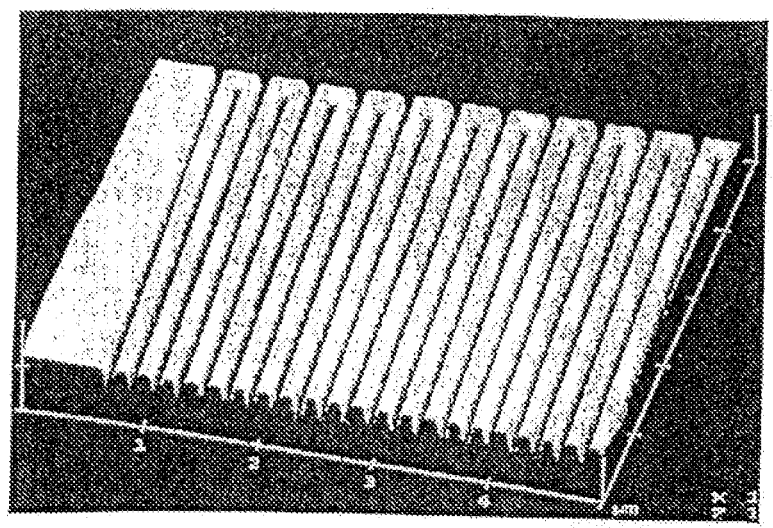
FIG. 35 is an atomic force micrograph image of 140-nm lines of TMPTA separated by distance of 70 nm that were fabricated using a PFPE mold.

Molding of Features for Semiconductor Applications 4.1 Fabrication of 140-nm Lines Separated by 70 nm in TMPTA A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, surfaces are generated by treating a silicon wafer cleaned with "piranha" solution (1:1 concentrated sulfuric acid:30% hydrogen peroxide (aq) solution) and treating the wafer with an adhesion promoter, (trimethoxysilyl propyl methacryalte). Following this, 50 μL of TMPTA is then placed on the treated silicon wafer and the patterned PFPE mold placed on top of it: The substrate is then placed in a molding apparatus and a small pressure is applied to ensure a conformal contact. The entire apparatus is then subjected to UV light ($\lambda$=365 nm) for ten minutes while under a nitrogen purge. Features are observed after separation of the PFPE mold and the treated silicon wafer using atomic force microscopy (AFM) (see FIG. 35).

4.2 Molding of a Polystyrene Solution

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, polystyrene is dissolved in 1 to 99 wt % of toluene. Flat, uniform, surfaces are generated by treating a silicon wafer cleaned with "piranha" solution (1:1 concentrated sulfuric acid:30% hydrogen peroxide (aq) solution) and treating the wafer with an adhesion promoter. Following this, 50 μL of polystyrene solution is then placed on the treated silicon wafer and the patterned PFPE mold is placed on top of it. The substrate is then placed in a molding apparatus and a small pressure is applied to ensure a conformal contact. The entire apparatus is then subjected to vacuum for a period of time to remove the solvent. Features are observed after separation of the PFPE mold and the treated silicon wafer using atomic force microscopy (AFM) and scanning electron microscopy (SEM).

4.3 Molding of Isolated Features on Microelectronics-Compatible Surfaces Using "Double Stamping"

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. A flat, non-wetting surface is generated by photocuring a film of PFPE-DMA onto a glass slide, according to the procedure outlined for generating a patterned PFPE-DMA mold. 50 μL of the TMPTA/photoinitiator solution is pressed between the PFPE-DMA mold and the flat PFPE-DMA surface, and pressure is applied to squeeze out excess TMPTA monomer. The PFPE-DMA mold is then removed from the flat PFPE-DMA surface and pressed against a clean, flat silicon/silicon oxide wafer and photocured using UV radiation ($\lambda$=365 nm) for 10 minutes while under a nitrogen purge. Isolated, poly (TMPTA) features are observed after separation of the PFPE mold and the silicon/silicon oxide wafer, using scanning electron microscopy (SEM).

4.4 Fabrication of 200-nm Titania Structures for Microelectronics

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 1 g of Pluronic P123 is dissolved in 12 g of absolute ethanol. This solution was added to a solution of 2.7 mL of concentrated hydrochloric acid and 3.88 mL titanium (IV) ethoxide. Flat, uniform, surfaces are generated by treating a silicon/silicon oxide wafer with "piranha" solution (1:1 concentrated sulfuric acid:30% hydrogen peroxide (aq) solution) and drying. Following this, 50 μL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sot-gel precursor has solidified. Oxide structures will be observed after separation of the PFPE mold and the treated silicon wafer using scanning electron microscopy (SEM).

4.5 Fabrication of 200-nm Silica Structures for Microelectronics

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 2 g of Pluronic P123 is dissolved in 30 g of water and 120 g of 2 M HCl is added while stirring at 35° C. To this solution, add 8.50 g of TEOS with stirring at 35° C. for 20 h. Flat, uniform, surfaces are generated by treating a silicon/silicon oxide wafer with "piranha" solution (1:1 concentrated sulfuric acid:30% hydrogen peroxide (aq) solution) and drying. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol gel precursor has solidified. Oxide structures will be observed after separation of the PFPE mold and the treated silicon wafer using scanning electron microscopy (SEM).

4.6 Fabrication of 200-nm Europium-Doped Titania Structures for Microelectronics A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 1 g of Pluronic P123 and 0.51 g of $EuCl_3.6H_2O$ are dissolved in 12 g of absolute ethanol. This solution was added to a solution of 2.7 mL of concentrated hydrochloric acid and 3.88 mL titanium (IV) ethoxide. Flat, uniform, surfaces are generated by treating a silicon/silicon oxide wafer with "piranha" solution (1:1 concentrated sulfuric acid:30% hydrogen peroxide (aq) solution) and drying. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. Oxide structures will be observed after separation of the PFPE mold and the treated silicon wafer using scanning electron microscopy (SEM).

4.7 Fabrication of Isolated "Scum Free" Features for Microelectronics

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, non-wetting surfaces capable of adhering to the resist material are generated by treating a silicon wafer cleaned with "piranha" solution (1:1 concentrated sulfuric acid:30% hydrogen peroxide (aq) solution) and treating the wafer with a mixture of an adhesion promoter, (trimethoxysilyl propyl methacrylate) and a non-wetting silane agent (1H, 1H, 2H, 2H-perfluorooctyl trimethoxysilane). The mixture can range from 100% of the adhesion promoter to 100% of the non-wetting silane. Following this, 50 µL of TMPTA is then placed on the treated silicon wafer and the patterned PFPE mold placed on top of it. The substrate is then placed in a molding apparatus and a small pressure is applied to ensure a conformal contact and to push out excess TMPTA. The entire apparatus is then subjected to UV light ($\lambda$=365 nm) for ten minutes while under a nitrogen purge. Features are observed after separation of the PFPE mold and the treated silicon wafer using atomic force microscopy (AFM) and scanning electron microscopy (SEM).

Example 5

Molding of Natural and Engineered Templates 5.1. Fabrication of a Perfluoropolyether-Dimethacrylate (PFPE-DMA) Mold from a Template Generated Using Electron-Beam Lithography A template, or "master," for perfluoropolyether-dimethacrylate (PFPE-DMA) mold fabrication is generated using electron beam lithography by spin coating a bilayer resist of 200,000 MW PMMA and 900,000 MW PMMA onto a silicon wafer with 500-nm thermal oxide, and exposing this resist layer to an electron beam that is translating in a pre-programmed pattern. The resist is developed in 3:1 isopropanol:methyl isobutyl ketone solution to remove exposed regions of the resist. A corresponding metal pattern is formed on the silicon oxide surface by evaporating 5 nm Cr and 15 nm Au onto the resist covered surface and lifting off the residual PMMA/Cr/Au film in refluxing acetone. This pattern is transferred to the underlying silicon oxide surface by reactive ion etching with $CF_4/O_2$ plasma and removal of the Cr/Au film in aqua regia (see FIG. 36). This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. This mold can be used for the fabrication of particles using non-wetting imprint lithography as specified in Particle Fabrication Examples 3.3 and 3.4.

5.2 Fabrication of a Perfluoropolyether-Dimethacrylate (PFPE-DMA Mold from a Template Generated Using Photolithography.

A template, or "master," for perfluoropolyether-dimethacrylate (PFPE-DMA) mold fabrication is generated using photolithography by spin coating a film of SU-8 photoresist onto a silicon wafer. This resist is baked on a hotplate at 95° C. and exposed through a pre-patterned photomask. The wafer is baked again at 95° C. and developed using a commercial developer solution to remove unexposed SU-8 resist. The resulting patterned surface is fully cured at 175° C. This master can be used to template a patterned mold by pouring PFPE-DMA containing 1-hydroxycyclohexyl phenyl ketone over the patterned area of the master. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master, and can be imaged by optical microscopy to reveal the patterned PFPE-DMA mold (see FIGS. 37A and 37B).

5.3 Fabrication of a Perfluoropolyether-Dimethacrylate PFPE-DMA) Mold from a Template Generated from Dispersed Tobacco Mosaic Virus Particles A template, or "master," for perfluoropolyether-dimethacrylate (PFPE-DMA) mold fabrication is generated by dispersing tobacco mosaic virus (TMV) particles on a silicon wafer (FIG. 38a). This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy (FIG. 38b).

5.4 Fabrication of a Perfluoropolyether-Dimethacrylate (PFPE-DMA) Mold from a Template Generated from Block-Copolymer Micelles A template, or "master," for perfluoropolyether-dimethacrylate (PFPE-DMA) mold fabrication is generated by dispersing polystyrene-polyisoprene block copolymer micelles on a freshly-cleaved mica surface. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy (see FIG. 39).

5.5 Fabrication of a Perfluoropolyether-Dimethacrylate (PFPE-DMA) Mold from a Template Generated from Brush Polymers.

A template, or "master," for perfluoropolyether-dimethacrylate (PFPE-DMA) mold fabrication is generated by dispersing poly(butyl acrylate) brush polymers on a freshly-cleaved mica surface. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy (FIG. 10).

5.6 Fabrication of a Perfluoropolyether-Dimethacrylate (PFPE-DMA) Mold from a Template Generated from Earthworm Hemoglobin Protein.

A template, or "master," for perfluoropolyether-dimethacrylate (PFPE-DMA) mold fabrication is generated by dispersing earthworm hemoglobin proteins on a freshly-cleaved mica surface. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy.

5.7 Fabrication of a Perfluoropolyether-Dimethacrylate (PFPE-DMA) Mold from a Template Generated from Patterned DNA Nanostructures.

A template, or "master," for perfluoropolyether-dimethacrylate (PFPE-DMA) mold fabrication is generated by dispersing DNA nanostructures on a freshly-cleaved mica surface. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy.

5.8 Fabrication of a Perfluoropolyether-Dimethacrylate (PFPE-DMA) Mold from a Template Generated from Carbon Nanotubes A template, or "master," for perfluoropolyether-dimethacrylate (PFPE-DMA) mold fabrication is generated by dispersing or growing carbon nanotubes on a silicon oxide wafer. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy.

Example 6

Method of Making Monodisperse Nanostructures Having a Plurality of Shapes and Sizes In some embodiments, the presently disclosed subject matter describes a novel "top down" soft lithographic technique; non-wetting imprint lithography (NoWIL) which allows completely isolated nanostructures to be generated by taking advantage of the inherent low surface energy and swelling resistance of cured PFPE-based materials.

The presently described subject matter provides a novel "top down" soft lithographic technique; non-wetting imprint lithography (NoWIL) which allows completely isolated nanostructures to be generated by taking advantage of the inherent low surface energy and swelling resistance of cured PFPE-based materials. Without being bound to any one particular theory, a key aspect of NoWIL is that both the elastomeric mold and the surface underneath the drop of monomer or resin are non-wetting to this droplet. If the droplet wets this surface, a thin scum layer will inevitably be present even if high pressures are exerted upon the mold. When both the elastomeric mold and the surface are non-wetting (i.e. a PFPE mold and fluorinated surface) the liquid is confined only to the features of the mold and the scum layer is eliminated as a seal forms between the elastomeric mold and the surface under a slight pressure. Thus, the presently disclosed subject matter provides for the first time a simple, general, soft lithographic method to produce nanoparticles of nearly any material, size, and shape that are limited only by the original master used to generate the mold.

Using NoWIL, nanoparticles composed of 3 different polymers were generated from a variety of engineered silicon masters. Representative patterns include, but are not limited to, 3-$\mu$m arrows (see FIG. 17), conical shapes that are 500 nm at the base and converge to <50 nm at the tip (see FIG. 15), and 200-nm trapezoidal structures (see FIG. 13). Definitive proof that all particles were indeed "scum-free" was demonstrated by the ability to mechanically harvest these particles by simply pushing a doctor's blade across the surface. See FIGS. 22 and 24.

Polyethylene glycol (PEG) is a material of interest for drug delivery applications because it is readily available, non-toxic, and biocompatible. The use of PEG nanoparticles generated by inverse microemulsions to be used as gene delivery vectors has previously been reported. K. McAllister et al., *Journal of the American Chemical Society* 124, 15198-15207 (Dec. 25, 2002). In the presently disclosed subject matter, NoWIL was performed using a commercially available PEG-diacrylate and blending it with 1 wt % of a photoinitiator, 1-hydroxycyclohexyl phenyl ketone. PFPE molds were generated from a variety of patterned silicon substrates using a dimethacrylate functionalized PFPE oligomer (PFPE DMA) as described previously. See J. P. Rolland, E. C. Hagberg, G. M. Denison, K. R. Carter, J. M. DeSimone, *Angewandte. Chemie-International Edition* 43, 5796-5799 (2004). In one embodiment, flat, uniform, non-wetting surfaces were generated by using a silicon wafer treated with a fluoroalkyl trichlorosilane or by casting a film of PFPE-DMA on a flat surface and photocuring. A small drop of PEG diacrylate was then placed on the non-wetting surface and the patterned PFPE mold placed on top of it. The substrate was then placed in a molding apparatus and a small pressure was applied to push out the excess PEG-diacrylate. The entire apparatus was then subjected to UV light ($\lambda$=365 nm) for ten minutes while under a nitrogen purge. Particles were observed after separation of the PFPE mold and flat, non-wetting substrate using optical microscopy, scanning electron microscopy (SEM), and atomic force microscopy (AFM).

Poly(lactic acid) (PLA) and derivatives thereof, such as poly(lactide-co-glycolide) (PLGA), have had a considerable impact on the drug delivery and medical device communities because it is biodegradable. See K. E. Uhrich, S. M. Cannizzaro, R. S. Langer, K. M. Shakesheff, *Chemical Reviews* 99, 3181-3198 (November, 1999); A. C. Albertsson, I. K. Varma, *Biomacromolecules* 4, 1466-1486 (November-December, 2003). As with PEG-based systems, progress has been made toward the fabrication of PLGA particles through various dispersion techniques that result in size distributions and are strictly limited to spherical shapes. See C. Cui, S. P. Schwendeman, *Langmuir* 34, 8426 (2001).

The presently disclosed subject matter demonstrates the use of NoWIL to generate discrete PLA particles with total control over shape and size distribution. For example, in one embodiment, one gram of (3S)-cis-3,6-dimethyl-1,4-dioxane-2,5-dione was heated above its melting temperature to 110° C. and ~20 µL of stannous octoate catalyst/initiator was added to the liquid monomer. A drop of the PLA monomer solution was then placed into a preheated molding apparatus which contained a non-wetting flat substrate and mold. A small pressure was applied as previously described to push out excess PLA monomer. The apparatus was allowed to heat at 110° C. for 15 h until the polymerization was complete. The PFPE-DMA mold and the flat, non-wetting substrate were then separated to reveal the PLA particles.

To further demonstrate the versatility of NoWIL, particles composed of a conducting polymer polypyrrole (PPy) were generated. PPy particles have been formed using dispersion methods, see M. R. Simmons, P. A. Chaloner, S. P. Armes, *Langmuir* 11, 4222 (1995), as well as "lost-wax" techniques, see P. Jiang, J. F. Bertone, V. L. Colvin, *Science* 291, 453 (2001).

The presently disclosed subject matter demonstrates for the first time, complete control over shape and size distribution of PPy particles. Pyrrole is known to polymerize instantaneously when in contact with oxidants such as perchloric acid. Dravid et al. has shown that this polymerization can be retarded by the addition of tetrahydrofuran (THF) to the pyrrole. See M. Su, M. Aslam, L. Fu, N. Q. Wu, V. P. Dravid, *Applied Physics Letters* 84, 4200-4202 (May 24, 2004).

The presently disclosed subject matter takes advantage of this property in the formation of PPy particles by NoWIL. For example, 50 µL of a 1:1 v/v solution of THF:pyrrole was added to 50 µL of 70% perchloric acid. A drop of this clear, brown solution (prior to complete polymerization) into the molding apparatus and applied pressure to remove excess solution. The apparatus was then placed into the vacuum oven overnight to remove the THF and water. PPy particles were fabricated with good fidelity using the same masters as previously described.

Importantly, the materials properties and polymerization mechanisms of PLA, PEG, and PPy are completely different. For example, while PLA is a high-modulus, semicrystalline polymer formed using a metal-catalyzed ring opening polymerization at high temperature, PEG is a malleable, waxy solid that is photocured free radically, and PPy is a conducting polymer polymerized using harsh oxidants. The fact that NoWIL can be used to fabricate particles from these diverse classes of polymeric materials that require very different reaction conditions underscores its generality and importance.

In addition to its ability to precisely control the size and shape of particles, NoWIL offers tremendous opportunities for the facile encapsulation of agents into nanoparticles. As described in Example 3-14, NoWIL can be used to encapsulate a 24-mer DNA strand fluorescently tagged with CY-3 inside the previously described 200 nm trapezoidal PEG particles. This was accomplished by simply adding the DNA to the monomer/water solution and molding them as described. We were able to confirm the encapsulation by observing the particles using confocal fluorescence microscopy (see FIG. 30). The presently described approach offers a distinct advantage over other encapsulation methods in that no surfactants, condensation agents, and the like are required. Furthermore, the fabrication of monodisperse, 200 nm particles containing DNA represents a breakthrough step towards artificial viruses. Accordingly, a host of biologically important agents, such as gene fragments, pharmaceuticals, oligonucleotides, and viruses, can be encapsulated by this method.

The method is also amenable to non-biologically oriented agents, such as metal nanoparticles, crystals, or catalysts. Further, the simplicity of this system allows for straightforward adjustment of particle properties, such as crosslink density, charge, and composition by the addition of other comonomers, and combinatorial generation of particle formulations that can be tailored for specific applications.

Accordingly, NoWIL is a highly versatile method for the production of isolated, discrete nanostructures of nearly any size and shape. The shapes presented herein were engineered non-arbitrary shapes. NoWIL can easily be used to mold and replicate non-engineered shapes found in nature, such as viruses, crystals, proteins, and the like. Furthermore, the technique can generate particles from a wide variety of organic and inorganic materials containing nearly any cargo. The method is simplistically elegant in that it does not involve complex surfactants or reaction conditions to generate nanoparticles. Finally, the process can be amplified to an industrial scale by using existing soft lithography roller technology, see Y. N. Xia, D. Qin, G. M. Whitesides, *Advanced Materials* 8, 1015-1017 (December, 1996), or silk screen printing methods.

Example 8

Synthesis of Degradable Crosslinkers for Hydrolysable PRINT Particles

Bis(ethylene methacrylate) disulfide (DEDSMA) was synthesized using methods described in Li et al. *Macromolecules* 2005, 38, 8155-8162 from 2-hyrdoxyethane disulfide and methacroyl chloride (Scheme 8). Analogously, bis(8-hydroxy-3,6-dioxaoctyl methacrylate) disulfide (TEDSMA) was synthesized from bis(8-hydroxy-3,6-dioxaoctyl) disulfide (Lana et al. *Langmuir* 1994, 10, 197-210). Methacroyl chloride (0.834 g, 8 mmole) was slowly added to a stirred solution of bis(8-hydroxy-3,6-dioxaoctyl) disulfide (0.662 g, 2 mmole) and triethylamine (2 mL) in acetonitrile (30 mL) chilled in an ice bath. The reaction was allowed to warm to room temperature and stirred for 16 hours. The mixture was diluted with 5% NaOH solution (50 mL) and stirred for an additional hour. The mixture was extracted with 2×60 mL of methylene chloride, the organic layer was washed 3×100 mL of 1 M NaOH, dried with anhydrous $K_2CO_2$, and filtered. Removal of the solvent yielded 0.860 g of the TEDSMA as a pale yellow oil. $^1$H NMR (CDCl$_3$) δ=6.11 (2H, s), 5.55 (2H, s), 4.29 (4H, t), 3.51-3.8 (16H, m), 2.85 (4H, t), 1.93 (6H, s).

Scheme 8

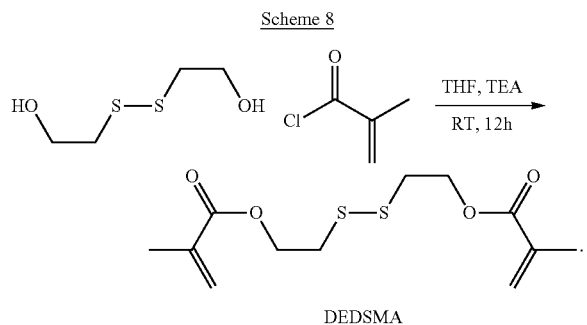

DEDSMA

8.1 Fabrication of 2 Mm Positively Charged DEDSMA Particles

Figure 40:
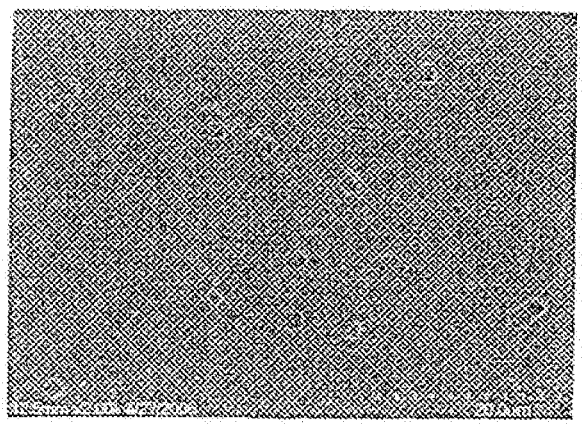
FIG. 40 shows an SEM micrograph of 2×2×1 µm positively charged DEDSMA particles according to an embodiment of the present invention.
Figure 41:
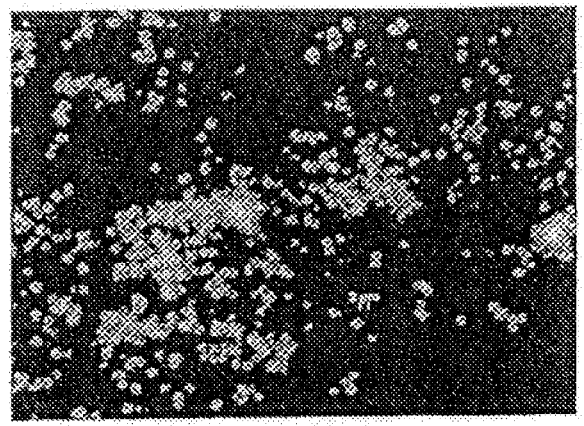
FIG. 41 shows a fluorescent micrograph of 2×2×1 µm positively charged DEDSMA particles according to an embodiment of the present invention.

A patterned perfluoropolyether (PFPE) mold was generated by pouring a PFPE-dimethacrylate (PFPE-DMA) containing 1-hydroxycyclohexyl phenyl ketone over a silicon substrate patterned with 2 µm rectangles. A poly(dimethylsiloxane) mold was used to confine the liquid PFPE-DMA to the desired area. The apparatus was then subjected to UV light ($\lambda$=365 nm) for 10 minutes while under a nitrogen purge. The fully cured PFPE-DMA mold was then released from the silicon master. Separately, a mixture composed of acryloxyethyltrimethylammonium chloride (24.4 mg), DEDSMA (213.0 mg), Polyfluor 570 (2.5 mg), diethoxyacetophenone (5.0 mg), methanol (39.0 mg), acetonitrile (39.0 mg), water (8.0 mg), and N,N-dimethylformamide (6.6 mg) was prepared. This mixture was spotted directly onto the patterned PFPE-DMA surface and covered with a separated unpatterned PFPE-DMA surface. The mold and surface were placed in molding apparatus, purge with $N_2$ for ten minutes, and placed under at least 500 N/cm$^2$ pressure for 2 hours. The entire apparatus was then subjected to UV light ($\lambda$=365 nm) for 40 minutes while maintaining nitrogen purge. DEDSMA particles were harvested on glass slide using cyanoacrylate adhesive. The particles were purified by dissolving the adhesive layer with acetone followed by centrifugation of the suspended particles (see FIGS. 40 and 41).

Figure 42:
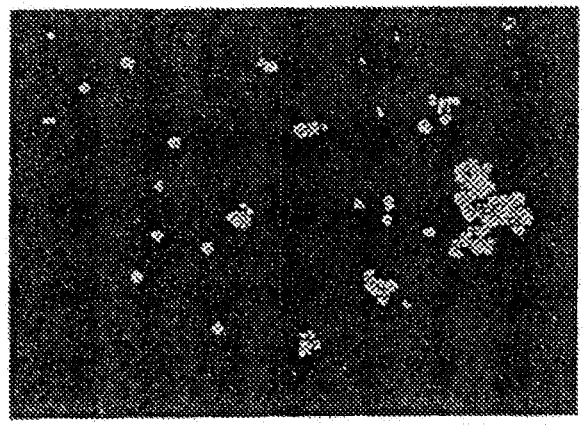
FIG. 42 shows a fluorescence micrograph of calcein cargo incorporated into 2 µm DEDSMA particles according to an embodiment of the present invention.

8.2 Encapsulation of Calcein Inside 2 µm Positively Charged DEDSMA Particles A patterned perfluoropolyether (PFPE) mold was generated by pouring a PFPE-dimethacrylate (PFPE-DMA) containing 1-hydroxycyclohexyl phenyl ketone over a silicon substrate patterned with 2 µm rectangles. A poly(dimethylsiloxane) mold was used to confine the liquid PFPE-DMA to the desired area. The apparatus was then subjected to UV light ($\lambda$=365 nm) for 10 minutes while under a nitrogen purge. The fully cured PFPE-DMA mold was then released from the silicon master. Separately, a mixture composed of acryloxyethyltrimethylammonium chloride (3.4 mg), DEDSMA (29.7 mg), calcein (0.7 mg), Polyfluor 570 (0.35 mg), diethoxyacetophenone (0.7 mg), methanol (5.45 mg), acetonitrile (5.45 mg), water (1.11 mg), and N,N-dimethylformamide (6.6 mg) was prepared. This mixture was spotted directly onto the patterned PFPE-DMA surface and covered with a separated unpatterned PFPE-DMA surface. The mold and surface were placed in molding apparatus, purge with $N_2$ for ten minutes, and placed under at least 500 N/cm$^2$ pressure for 2 hours. The entire apparatus was then subjected to UV light ($\lambda$=365 nm) for 40 minutes while maintaining nitrogen purge. Calcein containing DEDSMA particles were harvested on glass slide using cyanoacrylate adhesive. The particles were purified by dissolving the adhesive layer with acetone followed by centrifugation of the suspended particles (see FIG. 42).

8.3 Encapsulation of Plasmid DNA into Charged DEDSMA Particles

Figure 43:
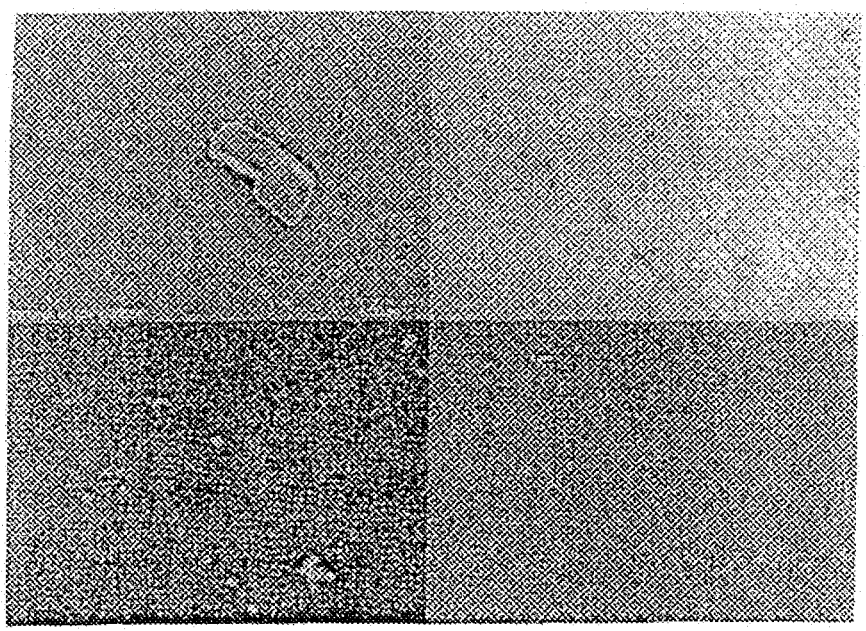
FIG. 43 shows 2×2×1 µm pDNA containing positively charged DEDSMA particles: Top Left: SEM, Top Right: DIC, Bottom Left: Particle-bound Polyfluor 570 fluorescence, Bottom Right: Fluorescein-labelled control plasmid fluorescence according to an embodiment of the present invention.

A patterned perfluoropolyether (PFPE) mold was generated by pouring a PFPE-dimethacrylate (PFPE-DMA) containing 1-hydroxycyclohexyl phenyl ketone over a silicon substrate patterned with 2 µm rectangles. A poly(dimethylsiloxane) mold was used to confine the liquid PFPE-DMA to the desired area. The apparatus was then subjected to UV light ($\lambda$=365 nm) for 10 minutes while under a nitrogen purge. The fully cured PFPE-DMA mold was then released from the silicon master. Separately, 0.5 µg of fluorescein-labelled plasmid DNA (Mirus Biotech) as a 0.25 µg/µL solution in TE buffer and a 2.0 µg of pSV β-galactosidase control vector (Promega) as a 1.0 µg/µL solution in TE buffer were sequentially added to a mixture composed of acryloxyethyltrimethylammonium chloride (1.44 mg), DEDSMA (12.7 mg), Polyfluor 570 (Polysciences, 0.08 mg), 1-hydroxycyclohexyl phenyl ketone (0.28 mg), methanol (5.96 mg), acetonitrile (5.96 mg), water (0.64 mg), and N,N-dimethylformamide (14.16 mg). This mixture was spotted directly onto the patterned PFPE-DMA surface and covered with a separated unpatterned PFPE-DMA surface. The mold and surface were placed in molding apparatus, purge with $N_2$ for ten minutes, and placed under at least 500 N/cm$^2$ pressure for 2 hours. The entire apparatus was then subjected to UV light ($\lambda$=365 nm) for 40 minutes while maintaining nitrogen purge. These particles were harvested on glass slide using cyanoacrylate adhesive. The particles were purified by dissolving the adhesive layer with acetone followed by centrifugation of the suspended particles (see FIG. 43).

8.4 Encapsulation of Plasmid DNA into PEG Particles

Figure 44:
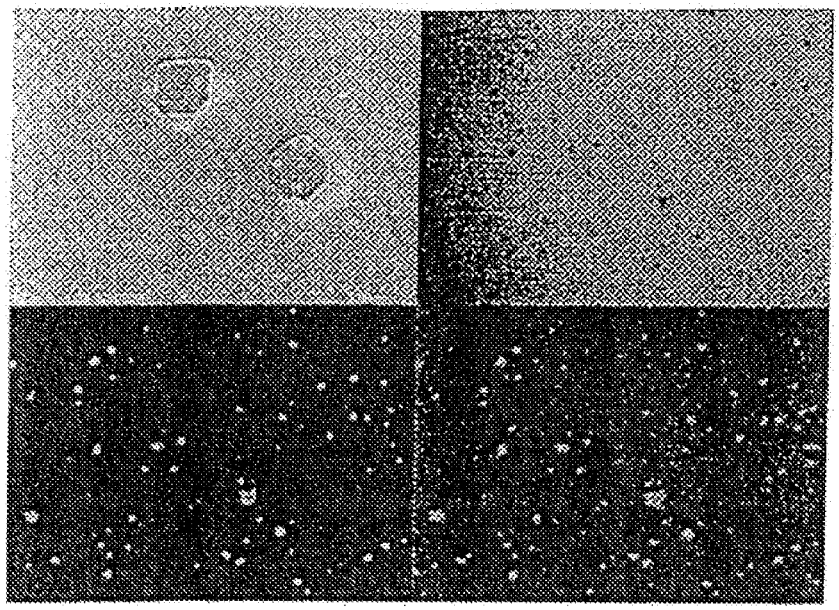
FIG. 44 shows 2×2×1 µm pDNA containing positively charged PEG particles: Top Left: SEM, Top Right: DIC, Bottom Left: Particle-bound Polyfluor 570 fluorescence, Bottom Right: Fluorescein-labelled control plasmid fluorescence according to an embodiment of the present invention.

A patterned perfluoropolyether (PFPE) mold was generated by pouring a PFPE-dimethacrylate (PFPE-DMA) containing 1-hydroxycyclohexyl phenyl ketone over a silicon substrate patterned with 2 µm rectangles. A poly(dimethylsiloxane) mold was used to confine the liquid PFPE-DMA to the desired area. The apparatus was then subjected to UV light ($\lambda$=365 nm) for 10 minutes while under a nitrogen purge. The fully cured PFPE-DMA mold was then released from the silicon master. Separately, 0.5 µg of fluorescein-labelled plasmid DNA (Mirus Biotech) as a 0.25 µg/L solution in TE buffer and a 2.0 μg of pSV β-galactosidase control vector (Promega) as a 1.0 μg/μL solution in TE buffer were sequentially added to a mixture composed of acryloxyethyltrimethylammonium chloride (1.2 mg), polyethylene glycol diacrylate (n=9) (10.56 mg), Polyfluor 570 (Polysciences, 0.12 mg), diethoxyacetophenone (0.12 mg), methanol (1.5 mg), water (0.31 mg), and N,N-dimethylformamide (7.2 mg). This mixture was spotted directly onto the patterned PFPE-DMA surface and covered with a separated unpatterned PFPE-DMA surface. The mold and surface were placed in molding apparatus, purge with $N_2$ for ten minutes, and placed under at least 500 N/cm$^2$ pressure for 2 hours. The entire apparatus was then subjected to UV light ($\lambda$=365 nm) for 40 minutes while maintaining nitrogen purge. These particles were harvested on glass slide using cyanoacrylate adhesive. The particles were purified by dissolving the adhesive layer with acetone followed by centrifugation of the suspended particles (see FIG. 44).

The following references may provide information and techniques to supplement some of the techniques and parameters of the present examples, therefore, the references are incorporated by reference herein in their entirety including any and all references cited therein. Li, Y., and Armes, S. P. Synthesis and Chemical Degradation of Branched Vinyl Polymers Prepared via ATRP: Use of a Cleavable Disulfide-Based Branching Agent. Macromolecules 2005; 38: 8155-8162; and Lang, H., Duschl, C., and Vogel, H. (1994), A new class of thiolipids for the attachment of lipid bilayers on gold surfaces. Langmuir 10, 197-210.

Example 9

Cellular Uptake of PRINT Particles

Figure 45:
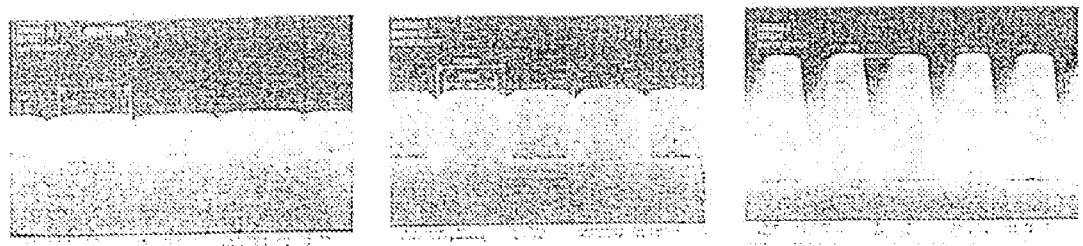
FIG. 45 shows master templates containing 200 nm cylindrical shapes with varying aspect ratios according to an embodiment of the present invention.
Figure 46:
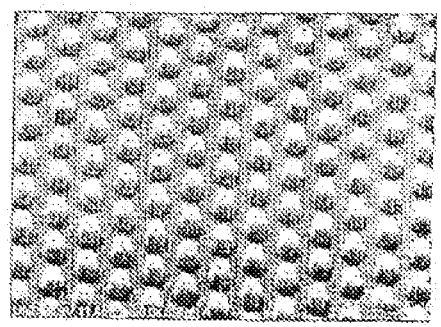
FIG. 46 shows a scanning electron micrograph (at a 45° angle) of harvested neutral PEG-composite 200 nm (aspect ratio=1:1) particles on the poly(cyanoacrylate) harvesting layer according to an embodiment of the present invention.

Effect of Charge 9.1 Fabrication of 200 nm Cylindrical Fluorescently-Tagged Neutral PEG Particles A patterned perfluoropolyether (PFPE) mold is generated by pouring a PFPE-dimethacrylate (PFPE-DMA) containing 2,2-diethoxyacetophenone over a silicon substrate patterned with 200 nm cylindrical shapes (see FIG. 45). The apparatus is then subjected to a nitrogen purge for 10 minutes before the application of UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 28 wt % PEG methacrylate (n=9), 2 wt % azobisisobutyronitrile (AIBN), and 0.25 wt % rhodamine methacrylate. Flat, uniform, non-wetting surfaces are generated by coating a glass slide with PFPE-dimethacrylate (PFPE-DMA) containing 2,2-diethoxyacetophenone. The slide is then subjected to a nitrogen purge for 10 minutes, then UV light is applied ($\lambda$=365 nm) while under a nitrogen purge. The flat, fully cured PFPE-DMA substrate is released from the slide. Following this, 0.1 mL of the monomer blend is evenly spotted onto the flat PFPE-DMA surface and then the patterned PFPE-DMA mold placed on top of it. The surface and mold are then placed in a molding apparatus and a small amount of pressure is applied to remove any excess monomer solution. The entire apparatus is purged with nitrogen for 10 minutes, then subjected to UV light ($\lambda$=365 nm) for 10 minutes while under a nitrogen purge. Neutral PEG nanoparticles are observed after separation of the PFPE-DMA mold and substrate using scanning electron microscopy (SEM). The harvesting process begins by spraying a thin layer of cyanoacrylate monomer onto the PFPE-DMA mold filled with particles. The PFPE-DMA mold is immediately placed onto a glass slide and the cyanoacrylate is allowed to polymerize in an anionic fashion for one minute. The mold is removed and the particles are embedded in the soluble adhesive layer (see FIG. 46), which provides isolated, harvested colloidal particle dispersions upon dissolution of the soluble adhesive polymer layer in acetone. Particles embedded in the harvesting layer, or dispersed in acetone can be visualized by SEM. The dissolved poly(cyanoacrylate) can remain with the particles in solution, or can be removed via centrifugation.

9.2 Fabrication of 200 nm Cylindrical Fluorescently-Tagged 14 wt % Cationically Charged PEG Particles A patterned perfluoropolyether (PFPE) mold is generated by pouring a PFPE-dimethacrylate (PFPE-DMA) containing 2,2-diethoxyacetophenone over a silicon substrate patterned with 200 nm cylindrical shapes (see FIG. 45). The apparatus is then subjected to a nitrogen purge for 10 minutes before the application of UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 14 wt % PEG methacrylate (n=9), 14 wt % 2-acryloxyethyltrimethylammonium chloride (AETMAC), 2 wt % azobisisobutyronitrile (AIBN), and 0.25 wt % rhodamine methacrylate. Flat, uniform, non-wetting surfaces are generated by coating a glass slide with PFPE-dimethacrylate (PFPE-DMA) containing 2,2-diethoxyacetophenone. The slide is then subjected to a nitrogen purge for 10 minutes, then UV light is applied ($\lambda$=365 nm) while under a nitrogen purge. The flat, fully cured PFPE-DMA substrate is released from the slide. Following this, 0.1 mL of the monomer blend is evenly spotted onto the flat PFPE-DMA surface and then the patterned PFPE-DMA mold placed on top of it. The surface and mold are then placed in a molding apparatus and a small amount of pressure is applied to remove any excess monomer solution. The entire apparatus is purged with nitrogen for 10 minutes, then subjected to UV light ($\lambda$=365 nm) for 10 minutes while under a nitrogen purge. Cationically charged PEG nanoparticles are observed after separation of the PFPE-DMA mold and substrate using scanning electron microscopy (SEM). The harvesting process begins by spraying a thin layer of cyanoacrylate monomer onto the PFPE-DMA mold filled with particles. The PFPE-DMA mold is immediately placed onto a glass slide and the cyanoacrylate is allowed to polymerize in an anionic fashion for one minute. The mold is removed and the particles are embedded in the soluble adhesive layer (see FIG. 46), which provides isolated, harvested colloidal particle dispersions upon dissolution of the soluble adhesive polymer layer in acetone. Particles embedded in the harvesting layer or dispersed in acetone can be visualized by SEM. The dissolved poly(cyanoacrylate) can remain with the particles in solution, or can be removed via centrifugation.

9.3 Fabrication of 200 nm Cylindrical Fluorescently-Tagged 28 wt % Cationically Charged PEG Particles A patterned perfluoropolyether (PFPE) mold is generated by pouring a PFPE-dimethacrylate (PFPE-DMA) containing 2,2-diethoxyacetophenone over a silicon substrate patterned with 200 nm cylindrical shapes (see FIG. 45). The apparatus is then subjected to a nitrogen purge for 10 minutes before the application of UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 28 wt % 2-acryloxyethyltrimethylammonium chloride (AETMAC), 2 wt % azobisisobutyronitrile (AIBN), and 0.25 wt % rhodamine methacrylate. Flat, uniform, non-wetting surfaces are generated by coating a glass slide with PFPE-dimethacrylate (PFPE-DMA) containing 2,2-diethoxyacetophenone.

The slide is then subjected to a nitrogen purge for 10 minutes, then UV light is applied (λ=365 nm) while under a nitrogen purge. The flat, fully cured PFPE-DMA substrate is released from the slide. Following this, 0.1 mL of the monomer blend is evenly spotted onto the flat PFPE-DMA surface and then the patterned PFPE-DMA mold placed on top of it. The surface and mold are then placed in a molding apparatus and a small amount of pressure is applied to remove any excess monomer solution. The entire apparatus is purged with nitrogen for 10 minutes, then subjected to UV light (λ=365 nm) for 10 minutes while under a nitrogen purge. Cationically charged PEG nanoparticles are observed after separation of the PFPE-DMA mold and substrate using scanning electron microscopy (SEM). The harvesting process begins by spraying a thin layer of cyanoacrylate monomer onto the PFPE-DMA mold filled with particles. The PFPE-DMA mold is immediately placed onto a glass slide and the cyanoacrylate is allowed to polymerize in an anionic fashion for one minute. The mold is removed and the particles are embedded in the soluble adhesive layer (see FIG. 46), which provides isolated, harvested colloidal particle dispersions upon dissolution of the soluble adhesive polymer layer in acetone. Particles embedded in the harvesting layer or dispersed in acetone can be visualized by SEM. The dissolved poly(cyanoacrylate) can remain with the particles in solution, or can be removed via centrifugation.

9.4 Cellular Uptake of 200 nm Cylindrically Shaped Neutral PEG PRINT Particles

Figure 47:
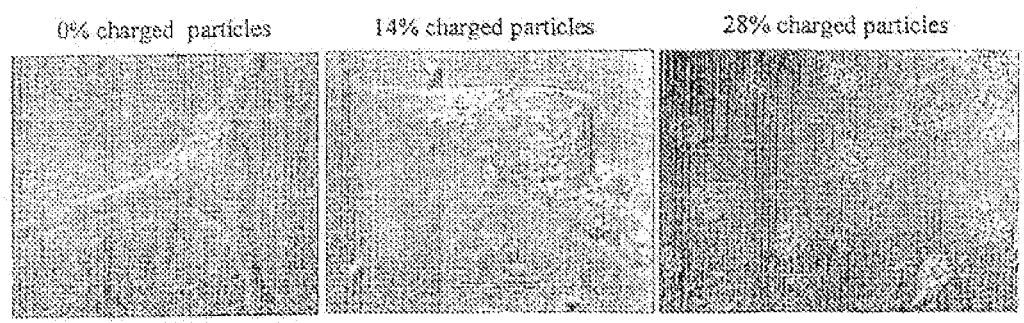
FIG. 47 shows confocal micrographs of cellular uptake of purified PRINT PEG-composite particles into NIH 3T3 cells—trends in amount of cationic charge according to an embodiment of the present invention.
Figure 48:
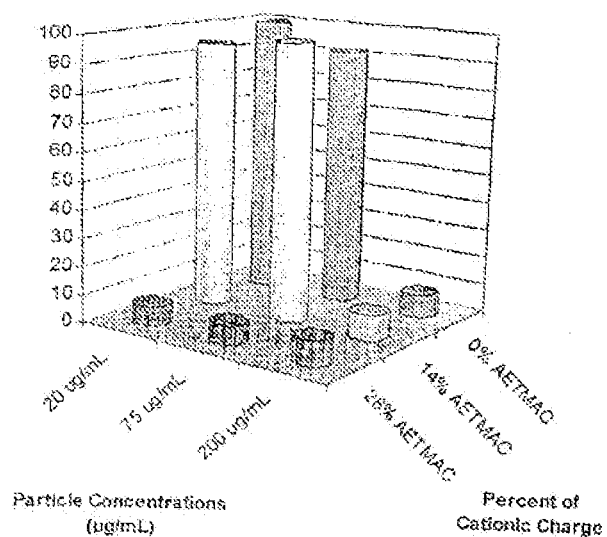
FIG. 48 shows toxicity results obtained from an MT assay on varying both the amount of cationic charge incorporated into a particle matrix, as well as an effect of particle concentration on cellular uptake according to an embodiment of the present invention.

The neutral 200 nm cylindrical PEG particles (aspect ratio=1:1, 200 nm×200 nm particles) fabricated using PRINT were dispersed in 250 μL of water to be used in cellular uptake experiments. These particles were exposed to NIH 3T3 (mouse embryonic) cells at a final concentration of particles of 60 μg/mL. The particles and cells were incubated for 4 hrs at 5% $CO_2$ at 37° C. The cells were then characterized via confocal microscopy (see FIG. 47) and cell toxicities were assessed using an MTT assay (see FIG. 48), 9.5 Cellular Uptake of 200 nm Cylindrically Shaped 14 Wt % Cationically Charged PEG PRINT Particles The 14 wt % cationically charged 200 nm cylindrical PEG particles (aspect ratio=1:1, 200 nm×200 nm particles) fabricated using PRINT were dispersed in 250 μL of water to be used in cellular uptake experiments. These particles were exposed to NIH 3T3 (mouse embryonic) cells at a final concentration of particles of 60 μg/mL. The particles and cells were incubated for 4 hrs at 5% $CO_2$ at 37° C. The cells were then characterized via confocal microscopy (see FIG. 47) and cell toxicities were assessed using an MTT assay (see FIG. 48).

9.6 Cellular Uptake of 200 nm Cylindrically Shaped 28 Wt % Cationically Charged PEG PRINT Particles The 28 wt % cationically charged 200 nm cylindrical PEG particles (aspect ratio=1:1, 200 nm×200 nm particles) fabricated using PRINT were dispersed in 250 μL of water to be used in cellular uptake experiments. These particles were exposed to NIH 3T3 (mouse embryonic) cells at a final concentration of particles of 60 μg/mL. The particles and cells were incubated for 4 hrs at 5% $CO_2$ at 37° C. The cells were then characterized via confocal microscopy (see FIG. 47) and cell toxicities were assessed using an MTT assay (see FIG. 48).

Example 10

Cellular Uptake of PRINT Particles

Effect of Size 10.1 Fabrication of 200 nm Cylindrical Fluorescently-Tagged 14 wt % Cationically Charged PEG Particles—Repeat A patterned perfluoropolyether (PFPE) mold is generated by pouring a PFPE-dimethacrylate (PFPE-DMA) containing 2,2-diethoxyacetophenone over a silicon substrate patterned with 200 nm cylindrical shapes (see FIG. 45). The apparatus is then subjected to a nitrogen purge for 10 minutes before the application of UV light (λ=365 nm) for 10 minutes while under a nitrogen purge. The fully cured PFPE-DMA mold is then released from the silicon master. Separately, a poly(ethylene glycol) (PEG) diacrylate (n=9) is blended with 14 wt % PEG methacrylate (n=9), 14 wt % 2-acryloxyethyltrimethylammonium chloride (AETMAC), 2 wt % azobisisobutyronitrile (AIBN), and 0.25 wt % rhodamine methacrylate. Flat, uniform, non-wetting surfaces are generated by coating a glass slide with PFPE-dimethacrylate (PFPE-DMA) containing 2,2-diethoxyacetophenone. The slide is then subjected to a nitrogen purge for 10 minutes, then UV light is applied (λ=365 nm) while under a nitrogen purge. The flat, fully cured PFPE-DMA substrate is released from the slide. Following this, 0.1 mL of the monomer blend is evenly spotted onto the flat PFPE-DMA surface and then the patterned PFPE-DMA mold placed on top of it. The surface and mold are then placed in a molding apparatus and a small amount of pressure is applied to remove any excess monomer solution. The entire apparatus is purged with nitrogen for 10 minutes, then subjected to UV light (λ=365 nm) for 10 minutes while under a nitrogen purge. Cationically charged PEG nanoparticles are observed after separation of the PFPE-DMA mold and substrate using scanning electron microscopy (SEM). The harvesting process begins by spraying a thin layer of cyanoacrylate monomer onto the PFPE-DMA mold filled with particles. The PFPE-DMA mold is immediately placed onto a glass slide and the cyanoacrylate is allowed to polymerize in an anionic fashion for one minute. The mold is removed and the particles are embedded in the soluble adhesive layer (see FIG. 46), which provides isolated, harvested colloidal particle dispersions upon dissolution of the soluble adhesive polymer layer in acetone. Particles embedded in the harvesting layer or dispersed in acetone can be visualized by SEM. The dissolved poly(cyanoacrylate) can remain with the particles in solution, or can be removed via centrifugation.

10.2 Fabrication of 2 μm×2 μm×1 μm Cubic Fluorescently-tagged 14 wt % Cationically Charged PEG Particles A patterned perfluoropolyether (PFPE) mold is generated by pouring a PFPE-dimethacrylate (PFPE-DMA) containing 2,2-diethoxyacetophenone over a silicon substrate patterned with 2 μm×2 μm×1 μm cubic shapes. The apparatus is then subjected to a nitrogen purge for 10 minutes before the application of UV light (λ=365 nm) for 10 minutes while under a nitrogen purge. The fully cured PFPE-DMA mold is then released from the silicon master. Separately, a poly(ethylene glycol) (PEG) diacrylate (n=9) is blended with 14 wt % PEG methacrylate (n=9), 14 wt % 2-acryloxyethyltrimethylammonium chloride (AETMAC), 2 wt % azobisisobutyronitrile (AIBN), and 0.25 wt % rhodamine methacrylate. Flat, uniform, non-wetting surfaces are generated by coating a glass slide with PFPE-dimethacrylate (PFPE-DMA) containing 2,2-diethoxyacetophenone. The slide is then subjected to a nitrogen purge for 10 minutes, then UV light is applied (λ=365 nm) while under a nitrogen purge. The flat, fully cured PFPE-DMA substrate is released from the slide. Following this, 0.1 mL of the monomer blend is evenly spotted onto the flat PFPE-DMA surface and then the patterned PFPE-DMA mold placed on top of it. The surface and mold are then placed in a molding apparatus and a small amount of pressure is applied to remove any excess monomer solution. The entire apparatus is purged with nitrogen for 10 minutes, then subjected to UV light (λ=365 nm) while under a nitrogen purge. Cationically charged PEG nanoparticles are observed after separation of the PFPE-DMA mold and substrate using scanning electron microscopy (SEM), optical and fluorescence microscopy (excitation λ=526 nm, emission λ=555 nm). The harvesting process begins by spraying a thin layer of cyanoacrylate monomer onto the PFPE-DMA mold filled with particles. The PFPE-DMA mold is immediately placed onto a glass slide and the cyanoacrylate is allowed to polymerize in an anionic fashion for one minute. The mold is removed and the particles are embedded in the soluble adhesive layer, which provides isolated, harvested colloidal particle dispersions upon dissolution of the soluble adhesive polymer layer in acetone. Particles embedded in the harvesting layer or dispersed in acetone can be visualized by SEM. The dissolved poly(cyanoacrylate) can remain with the particles in solution, or can be removed via centrifugation.

10.3 Fabrication of 5 μm×5 μm×5 μm Cubic Fluorescently-Tagged 14 wt % Cationically Charged PEG Particles A patterned perfluoropolyether (PFPE) mold is generated by pouring a PFPE-dimethacrylate (PFPE-DMA) containing 2,2-diethoxyacetophenone over a silicon substrate patterned with 5 μm×5 μm×5 μm cubic shapes. The apparatus is then subjected to a nitrogen purge for 10 minutes before the application of UV light (λ=365 nm) for 10 minutes while under a nitrogen purge. The fully cured PFPE-DMA mold is then released from the silicon master. Separately, a poly(ethylene glycol) (PEG) diacrylate (n=9) is blended with 14 wt % PEG methacrylate (n=9), 14 wt % 2-acryloxyethyltrimethylammonium chloride (AETMAC), 2 wt % azobisisobutyronitrile (AIBN), and 0.25 wt % rhodamine methacrylate. Flat, uniform, non-wetting surfaces are generated by coating a glass slide with PFPE-dimethacrylate (PFPE-DMA) containing 2,2-diethoxyacetophenone. The slide is then subjected to a nitrogen purge for 10 minutes, then UV light is applied (λ=365 nm) while under a nitrogen purge. The flat, fully cured PFPE-DMA substrate is released from the slide. Following this, 0.1 mL of the monomer blend is evenly spotted onto the flat PFPE-DMA surface and then the patterned PFPE-DMA mold placed on top of it. The surface and mold are then placed in a molding apparatus and a small amount of pressure is applied to remove any excess monomer solution. The entire apparatus is purged with nitrogen for 10 minutes, then subjected to UV light (λ=365 nm) for 10 minutes while under a nitrogen purge. Cationically charged PEG nanoparticles are observed after separation of the PFPE-DMA mold and substrate using scanning electron microscopy (SEM), optical and fluorescence microscopy (excitation λ=526 nm, emission λ=555 nm). The harvesting process begins by spraying a thin layer of cyanoacrylate monomer onto the PFPE-DMA mold filled with particles. The PFPE-DMA mold is immediately placed onto a glass slide and the cyanoacrylate is allowed to polymerize in an anionic fashion for one minute. The mold is removed and the particles are embedded in the soluble adhesive layer, which provides isolated, harvested colloidal particle dispersions upon dissolution of the soluble adhesive polymer layer in acetone. Particles embedded in the harvesting layer, or dispersed in acetone can be visualized by SEM. The dissolved poly(cyanoacrylate) can remain with the particles in solution, or can be removed via centrifugation.

Figure 49:
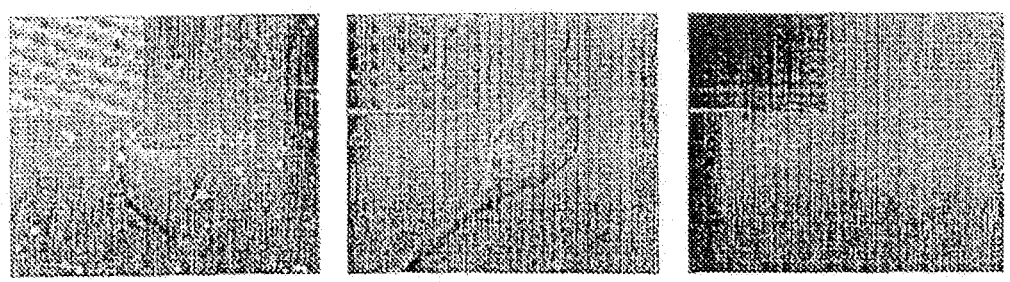
FIG. 49 shows confocal micrographs of cellular uptake of PRINT PEG particles into NIH 3T3 cells while the inserts show harvested particles on medical adhesive layers prior to cellular treatment according to an embodiment of the present invention.

10.4 Cellular Uptake of 200 nm Cylindrically Shaped 14 Wt % Cationically Charged PEG PRINT Particles—Repeat The 14 wt % cationically charged 200 nm cylindrical PEG particles (aspect ratio=1:1, 200 nm×200 nm particles) fabricated using PRINT were dispersed in 250 μL of water to be used in cellular uptake experiments. These particles were exposed to NIH 3T3 (mouse embryonic) cells at a final concentration of particles of 60 μg/mL. The particles and cells were incubated for 4 hrs at 5% $CO_2$ at 37° C. The cells were then characterized via confocal microscopy (see FIG. 49).

10.5 Cellular Uptake of 2 μm×2 μm×1 μm Cubic Shaped 14 wt % Cationically Charged PEG PRINT Particles The 14 wt % cationically charged 2 μm×2 μm×1 μm cubic PEG particles fabricated using PRINT were dispersed in 250 μL of water to be used in cellular uptake experiments. These particles were exposed to NIH 3T3 (mouse embryonic) cells at a final concentration of particles of 60 μg/mL. The particles and cells were incubated for 4 hrs at 5% $CO_2$ at 37° C. The cells were then characterized via confocal microscopy (see FIG. 49).

10.6 Cellular Uptake of 5 μm×5 μm×5 μm Cubic Shaped 14 wt % Cationically Charged PEG PRINT Particles The 14 wt % cationically charged 5 μm×5 μm×5 μm cubic PEG particles fabricated using PRINT were dispersed in 250 μL of water to be used in cellular uptake experiments. These particles were exposed to NIH 3T3 (mouse embryonic) cells at a final concentration of particles of 60 μg/mL. The particles and cells were incubated for 4 hrs at 5% $CO_2$ at 37° C. The cells were then characterized via confocal microscopy (see FIG. 49).

Example 11

Cellular Uptake of DEDSMA PRINT Particles 11.1 Cellular Uptake of DEDSMA PRINT Particles The DEDSMA particles fabricated using PRINT were dispersed in 250 μL of water to be used in cellular uptake experiments. These particles were exposed to NIH 3T3 (mouse embryonic) cells at a final concentration of particles of 60 μg/mL. The particles and cells were incubated for 4 hrs at 5% $CO_2$ at 37° C. The cells were then characterized via confocal microscopy.

Example 12

Figure 50:
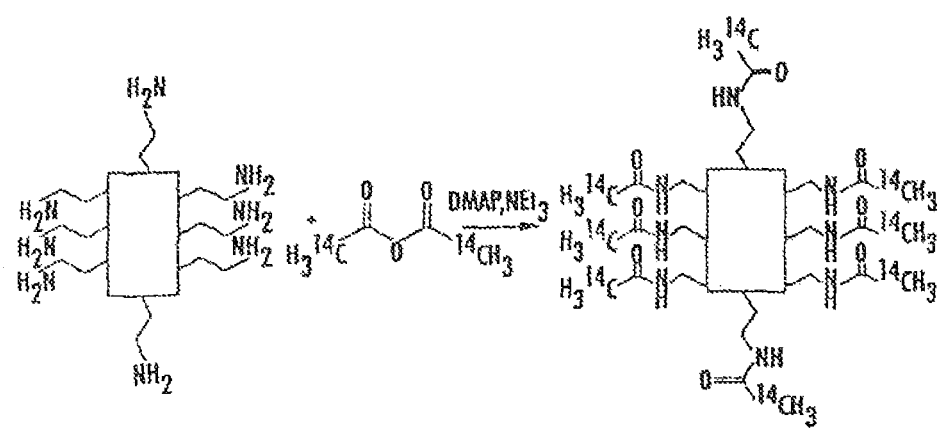
FIG. 50 shows a reaction scheme for conjugation of a radioactively labeled moiety to PRINT particles according to an embodiment of the present invention.

Radiolabeling PRINT Particles 12.1 Synthesis of $^{14}C$ radiolabeled 2 μm×2 μm×1 μm Cubic PRINT Particles A patterned perfluoropolyether (PFPE) mold is generated by pouring a PFPE-dimethacrylate (PFPE-DMA) containing 2,2-diethoxyacetophenone over a silicon substrate patterned with 2 μm×2 μm×1 μm cubic shapes. The apparatus is then subjected to a nitrogen purge for 10 minutes before the application of UV light (λ=365 nm) for 10 minutes while under a nitrogen purge. The fully cured PFPE-DMA mold is then released from the silicon master. Separately, a poly(ethylene glycol) (PEG) diacrylate (n=9) is blended with 30 wt % 2-aminoethylmethacrylate hydrochloride (AEM), and 1 wt % 2,2-diethoxyacetophenone. The monomer solution is applied to the mold by spraying a diluted (10×) blend of the monomers with isopropyl alcohol. A polyethylene sheet is placed onto the mold, and any residual air bubbles are pushed out with a roller. The sheet is slowly pulled back from the mold at a rate of 1 inch/minute. The mold is then subjected to a nitrogen purge for 10 minutes, then UV light is applied (λ=365 nm) while under a nitrogen purge. The harvesting process begins by spraying a thin layer of cyanoacrylate monomer onto the PFPE-DMA mold filled with particles. The PFPE-DMA mold is immediately placed onto a glass slide and the cyanoacrylate is allowed to polymerize in an anionic fashion for one minute. The mold is removed and the particles are embedded in the soluble adhesive layer, which provides isolated, harvested colloidal particle dispersions upon dissolution of the soluble adhesive polymer layer in acetone. Particles embedded in the harvesting layer, or dispersed in acetone can be visualized by SEM, and optical microscopy. The dissolved poly(cyanoacrylate) can remain with the particles in solution, or can be removed via centrifugation. The dry, purified particles are then exposed to $^{14}$C-acetic anhydride in dry dichloromethane in the presence of triethylamine, and 4-dimethylaminopyridine for 24 hours (see FIG. 50). Unreacted reagents are removed via centrifugation. Efficiency of the reaction is monitored by measured the emitted radioactivity in a scintillation vial.

12.2 Synthesis of $^{14}$C Radiolabeled 200 nm Cylindrical PRINT Particles

A patterned perfluoropolyether (PFPE) mold is generated by pouring a PFPE-dimethacrylate (PFPE-DMA) containing 2,2-diethoxyacetophenone over a silicon substrate patterned with 200 nm cylindrical shapes. The apparatus is then subjected to a nitrogen purge for 10 minutes before the application of UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 30 wt % 2-aminoethylmethacrylate hydrochloride (AEM), and 1 wt % 2,2-diethoxyacetophenone. The monomer solution is applied to the mold by spraying a diluted (10×) blend of the monomers with isopropyl alcohol. A polyethylene sheet is placed onto the mold, and any residual air bubbles are pushed out with a roller. The sheet is slowly pulled back from the mold at a rate of 1 inch/minute. The mold is then subjected to a nitrogen purge for 10 minutes, then UV light is applied ($\lambda$=365 nm) while under a nitrogen purge. The harvesting process begins by spraying a thin layer of cyanoacrylate monomer onto the PFPE-DMA mold filled with particles. The PFPE-DMA mold is immediately placed onto a glass slide and the cyanoacrylate is allowed to polymerize in an anionic fashion for one minute. The mold is removed and the particles are embedded in the soluble adhesive layer, which provides isolated, harvested colloidal particle dispersions upon dissolution of the soluble adhesive polymer layer in acetone. Particles embedded in the harvesting layer, or dispersed in acetone can be visualized by SEM. The dissolved poly(cyanoacrylate) can remain with the particles in solution, or can be removed via centrifugation. The dry, purified particles are then exposed to $^{14}$C-acetic anhydride in dry dichloromethane in the presence of triethylamine, and 4-dimethylaminopyridine for 24 hours (see FIG. 50). Unreacted reagents are removed via centrifugation. Efficiency of the reaction is monitored by measured the emitted radioactivity in a scintillation vial.

12.3 Fabrication of Pendant Gadolinium PEG Particles

Figure 51:
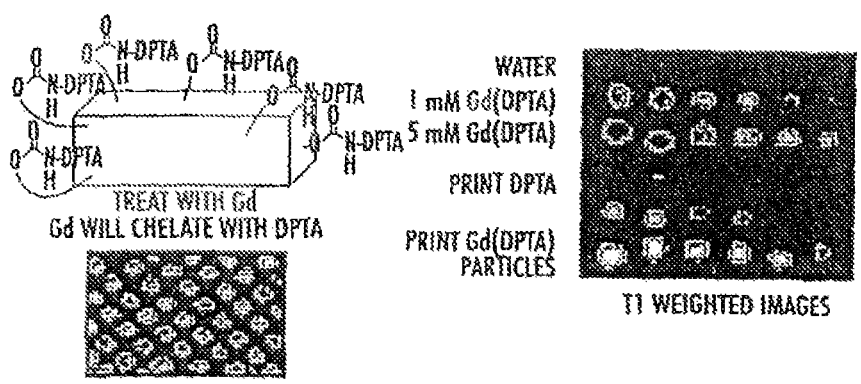
FIG. 51 shows fabrication of pendant gadolinium PEG particles according to an embodiment of the present invention.

A patterned perfluoropolyether (PFPE) mold is generated by pouring a PFPE-dimethacrylate (PFPE-DMA) containing 2,2'-diethoxy-acetophenone over a silicon substrate patterned with 3×3×11 um pillar shapes. The apparatus is then subjected to UV light ($\lambda$=365 nm) for 15 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 2,2'-diethoxy-acetophenone. 20 µL of chloroform, 70 µL of PEG diacrylate monomer and 30 uL of DPTA-PEG-acrylate are mixed. Flat, uniform, non-wetting surfaces are generated by pouring a PFPE-dimethacrylate (PFPE-DMA) containing 2,2'-diethoxy-acetophenone over a silicon wafer and then subjected to UV light ($\lambda$=365 nm) for 15 minutes while under a nitrogen purge. Following this, 50 µL of the PEG diacrylate solution is then placed on the non-wetting surface and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for 15 minutes while under a nitrogen purge. Particles are observed after separation of the PFPE mold. The particles were harvested utilizing a sacrificial adhesive layer and verified via DIC microscopy. These particles were subsequently treated with an aqueous solution of $Gd(NO_3)_3$. These particles were then dispersed in a agrose gel and TI weighted imaging profiles were examined utilizing a Siemens Allegra 3T head magnetic resonance instrument (see FIG. 51).

12.4 Forming a Particle Containing CDI Linker

Figure 52:
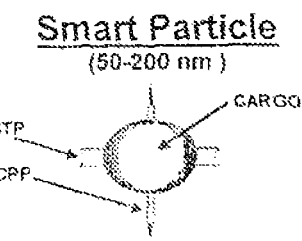
FIG. 52 shows formation of a particle containing CDI linker according to an embodiment of the present invention.

A patterned perfluoropolyether (PFPE) mold is generated by pouring a PFPE-dimethacrylate (PFPE-DMA) containing 2,2'-diethoxy-acetophenone over a silicon substrate patterned with 200 nm shapes. The apparatus is then subjected to UV light ($\lambda$=365 nm) for 15 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 2,2'-diethoxy-acetophenone. 70 µL of PEG diacrylate monomer and 30 uL of CDI-PEG monomer were mixed. Specifically, the CDI-PEG monomer was synthesized by adding 1,1'-carbonyl diimidazole (CDI) to a solution of PEG (n=400) monomethylacrylate in chloroform. This solution was allowed to stir overnight. This solution was then further purified by an extraction with cold water. The resulting CDI-PEG monomethacrylate was then isolated via vacuum. Flat, uniform, non-wetting surfaces are generated by pouring a PFPE-dimethacrylate (PFPE-DMA) containing 2,2'-diethoxy-acetophenone over a silicon wafer and then subjected to UV light ($\mu$=365 nm) for 15 minutes while under a nitrogen purge. Following this, 50 µL of the PEG diacrylate solution is then placed on the non wetting surface and the patterned PFPE mold placed on top of it. The substrate is then placed in a molding apparatus and a small pressure is applied to push out excess PEG-diacrylate solution. The entire apparatus is then subjected to UV light (h=365 nm) for 15 minutes while under a nitrogen purge. Particles are observed after separation of the PFPE mold. The particles were harvested utilizing a sacrificial adhesive layer and verified via DIC microscopy. This linker can be utilized to attach an amine containing target onto the particle (see FIG. 52).

12.5 Tethering Avidin to the CDI Linker

Figure 53:
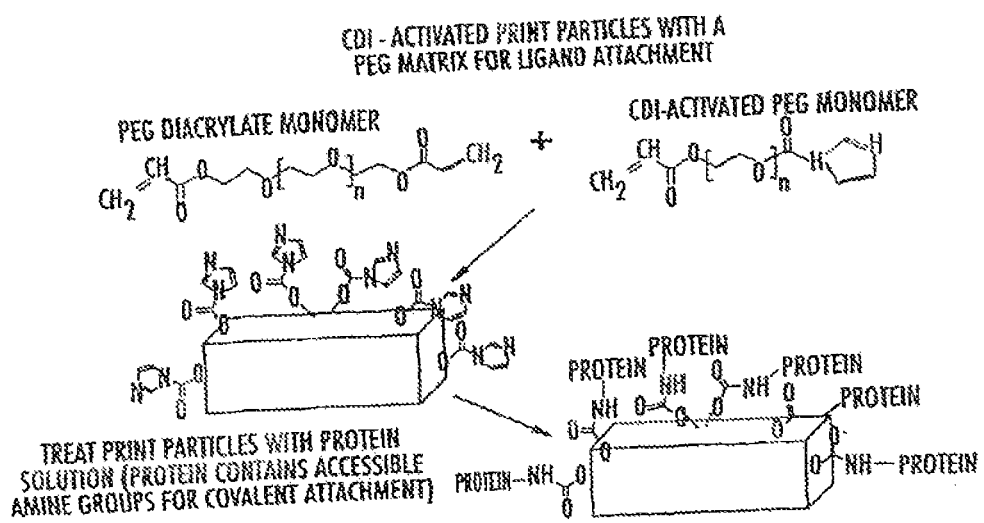
FIG. 53 shows tethering avidin to a CDI linker according to an embodiment of the present invention.

A patterned perfluoropolyether (PFPE) mold is generated by pouring a PFPE-dimethacrylate (PFPE-DMA) containing 2,2'-diethoxy-acetophenone over a silicon substrate patterned with 200 nm shapes. The apparatus is then subjected to UV light ($\lambda$=365 nm) for 15 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 2,2'-diethoxy-acetophenone. 70 µL of PEG diacrylate monomer and 30 uL of CDI-PEG monomer were mixed. Specifically, the CDI-PEG monomer was synthesized by adding 1,1'-carbonyl diimidazole (CDI) to a solution of PEG (n=400) monomethylacrylate in chloroform. This solution was allowed to stir overnight. This solution was then further purified by an extraction with cold water. The resulting CDI-PEG monomethacrylate was then isolated via vacuum. Flat, uniform, non-wetting surfaces are generated by pouring a PFPE-dimethacrylate (PFPE-DMA) containing 2,2'-diethoxy-acetophenone over a silicon wafer and then subjected to UV light ($\lambda$=365 nm) for 15 minutes while under a nitrogen purge. Following this, 50 μL of the PEG diacrylate solution is then placed on the non wetting surface and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for 15 minutes while under a nitrogen purge. Particles are observed after separation of the PFPE mold. The particles were harvested utilizing a sacrificial adhesive layer and verified via DIC microscopy. These particles containing the CDI linker group were subsequently treated with and aqueous solution of fluorescently tagged avidin. These particles were allowed to stir at room temperature for four hours. These particles were then isolated via centrifugation and rinsed with deionized water. Attachment was confirmed via confocal microscopy (see FIG. 53).

12.6 Fabrication of PEG Particles that Target the HER2 Receptor

Figure 54:
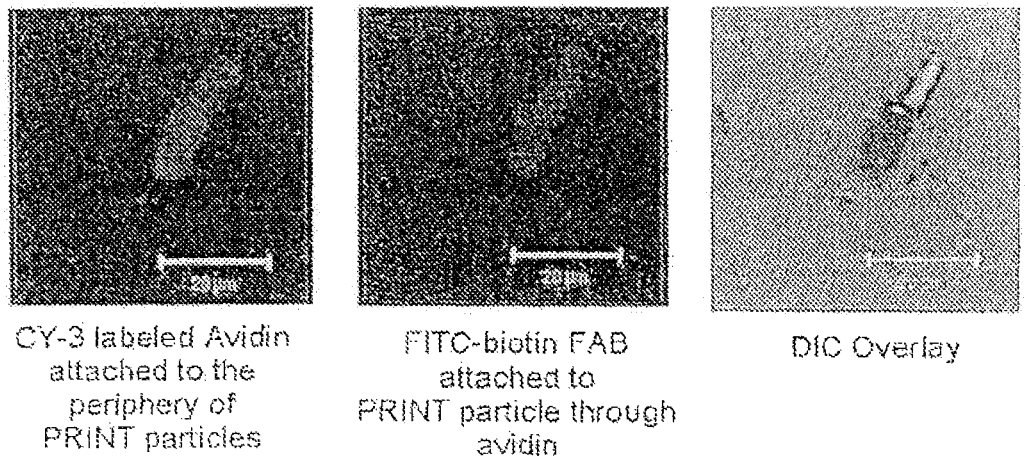
FIG. 54 shows fabrication of PEG particles that target an HER2 receptor according to an embodiment of the present invention.
Figure 54:
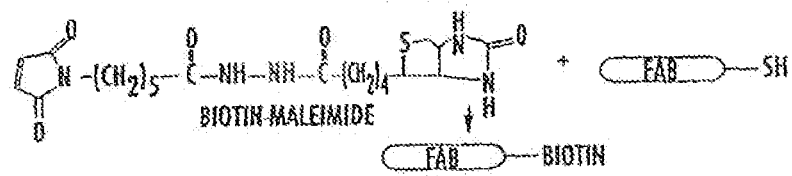

A patterned perfluoropolyether (PFPE) mold is generated by pouring a PFPE-dimethacrylate (PFPE-DMA) containing 2,2'-diethoxy-acetophenone over a silicon substrate patterned with 200 nm shapes. The apparatus is then subjected to UV light ($\lambda$=365 nm) for 15 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 2,2'-diethoxy-acetophenone. 70 μL of PEG diacrylate monomer and 30 uL of CDI-PEG monomer were mixed. Specifically, the CDI-PEG monomer was synthesized by adding 1,1'-carbonyl diimidazole (CDI) to a solution of PEG (n=400) monomethylacrylate in chloroform. This solution was allowed to stir overnight. This solution was then further purified by an extraction with cold water. The resulting CDI-PEG monomethacrylate was then isolated via vacuum. Flat, uniform, non-wetting surfaces are generated by pouring a PFPE-dimethacrylate (PFPE-DMA) containing 2,2'-diethoxy-acetophenone over a silicon wafer and then subjected to UV light ($\lambda$=365 nm) for 15 minutes while under a nitrogen purge. Following this, 50 μL of the PEG diacrylate solution is then placed on the non wetting surface and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for 15 minutes while under a nitrogen purge. Particles are observed after separation of the PFPE mold. The particles were harvested utilizing a sacrificial adhesive layer and verified via DIC microscopy. These particles containing the CDI linker group were subsequently treated with and aqueous solution of fluorescently tagged avidin. These particles were allowed to stir at room temperature for four hours. These particles were then isolated via centrifugation and rinsed with deionized water. These avidin labeled particles were then treated with biotinylated FAB fragments. Attachment was confirmed via confocal microscopy (see FIG. 54).

12.7 Fabrication of PEG Particles that Target Non-Hodgkin's Lymphoma

Figure 55:
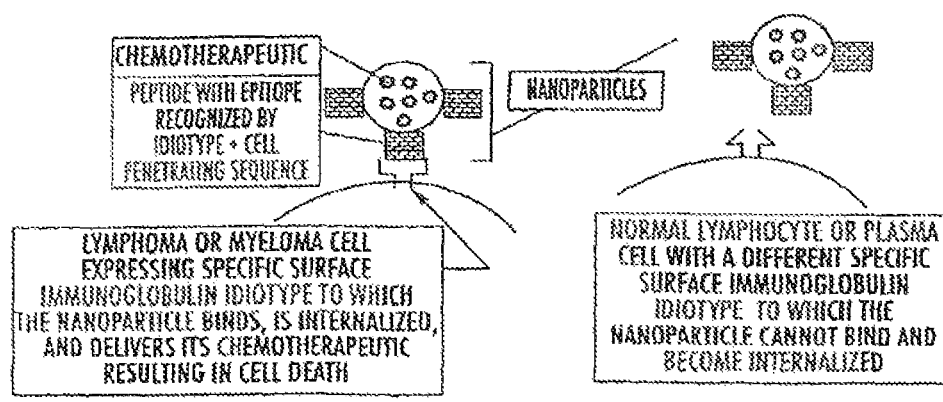
FIG. 55 shows fabrication of PEG particles that target non-Hodgkin's lymphoma according to an embodiment of the present invention.

A patterned perfluoropolyether (PFPE) mold is generated by pouring a PFPE-dimethacrylate (PFPE-DMA) containing 2,2'-diethoxy-acetophenone over a silicon substrate patterned with 200 nm shapes. The apparatus is then subjected to UV light ($\lambda$=365 nm) for 15 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 2,2'-diethoxy-acetophenone. 70 μL of PEG diacrylate monomer and 30 uL of CDI-PEG monomer were mixed. Specifically, the CDI-PEG monomer was synthesized by adding 1,1'-carbonyl diimidazole (CDI) to a solution of PEG (n=400) monomethylacrylate in chloroform. This solution was allowed to stir overnight. This solution was then further purified by an extraction with cold water. The resulting CDI-PEG monomethacrylate was then isolated via vacuum. Flat, uniform, non-wetting surfaces are generated by pouring a PFPE-dimethacrylate (PFPE-DMA) containing 2,2'-diethoxy-acetophenone over a silicon wafer and then subjected to UV light ($\lambda$=365 nm) for 15 minutes while under a nitrogen purge. Following this, 50 μL of the PEG diacrylate solution is then placed on the non wetting surface and the patterned PFPE mold placed on top of it. The substrate is then placed in a molding apparatus and a small pressure is applied to push out excess PEG-diacrylate solution. The entire apparatus is then subjected to UV light (J=365 nm) for 15 minutes while under a nitrogen purge. Particles are observed after separation of the PFPE mold. The particles were harvested utilizing a sacrificial adhesive layer and verified via DIC microscopy. These particles containing the CDI linker group were subsequently treated with and aqueous solution of fluorescently tagged avidin. These particles were allowed to stir at room temperature for four hours. These particles were then isolated via centrifugation and rinsed with deionized water. These avidin labeled particles were then treated with biotinylated-SUP-B8 (peptide specific to the specific surface immunoglobulin (sIg) known as the idiotype, which is distinct from the sIg of all of the patient's non-neoplastic cells) (see FIG. 55).

12.8 Controlled Mesh Density: Phantom Study and Cellular Uptake/MTT Assay

A patterned perfluoropolyether (PFPE) mold is generated by pouring a PFPE-dimethacrylate (PFPE-DMA) containing 2,2'-diethoxy-acetophenone over a silicon substrate patterned with 3×3×11 um pillar shapes. The apparatus is then subjected to UV light ($\lambda$=365 nm) for 15 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 2,2'-diethoxy-acetophenone. 56 μL of PEG diacrylate monomer, 19 uL of PEG monomethacrylate, 10 ug 2-acryloxyethyltrimethylammonium chloride (AETMAC), and 23 uL of a doxorubicin (26 mg/mL) are mixed. Flat, uniform, non-wetting surfaces are generated by pouring a PFPE-dimethacrylate (PFPE-DMA) containing 2,2'-diethoxy-acetophenone over a silicon wafer and then subjected to UV light ($\lambda$=365 nm) for 15 minutes while under a nitrogen purge. Following this, 50 μL of the PEG diacrylate solution is then placed on the non-wetting surface and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for 15 minutes while under a nitrogen purge. Particles are observed after separation of the PFPE mold. The particles were harvested utilizing a sacrificial adhesive layer and verified via DIC microscopy. These particles were then dispersed in an aqueous solution and exposed to NIH 3T3 mouse embryo fibroblasts cell lines at a concentration of nanoparticles of 50 ug/mL. The particles and cells were incubated for 48 hrs at 5% $CO_2$ at 37° C. The cells were then characterized via confocal and MTT assay.

12.9 Fabrication of Particles by Dipping Methods

Figure 56:
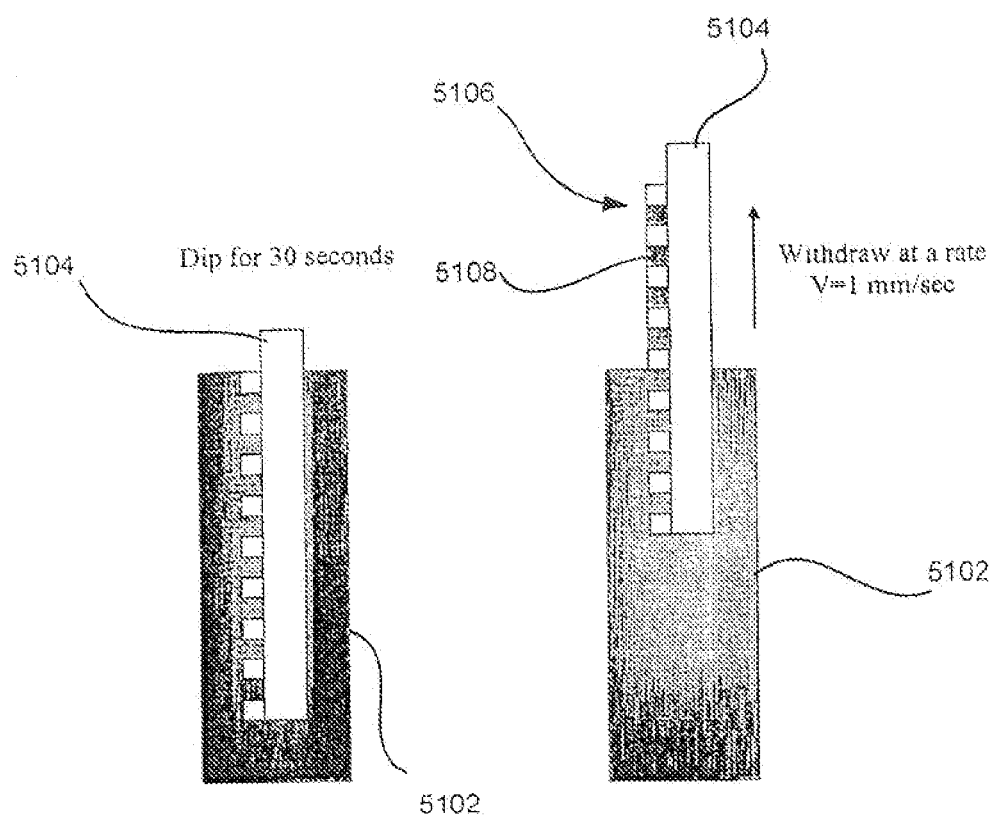
FIG. 56 shows a method of dipping a patterned template to introduce a substance into recesses of the patterned template according to an embodiment of the present invention.
Figure 57:
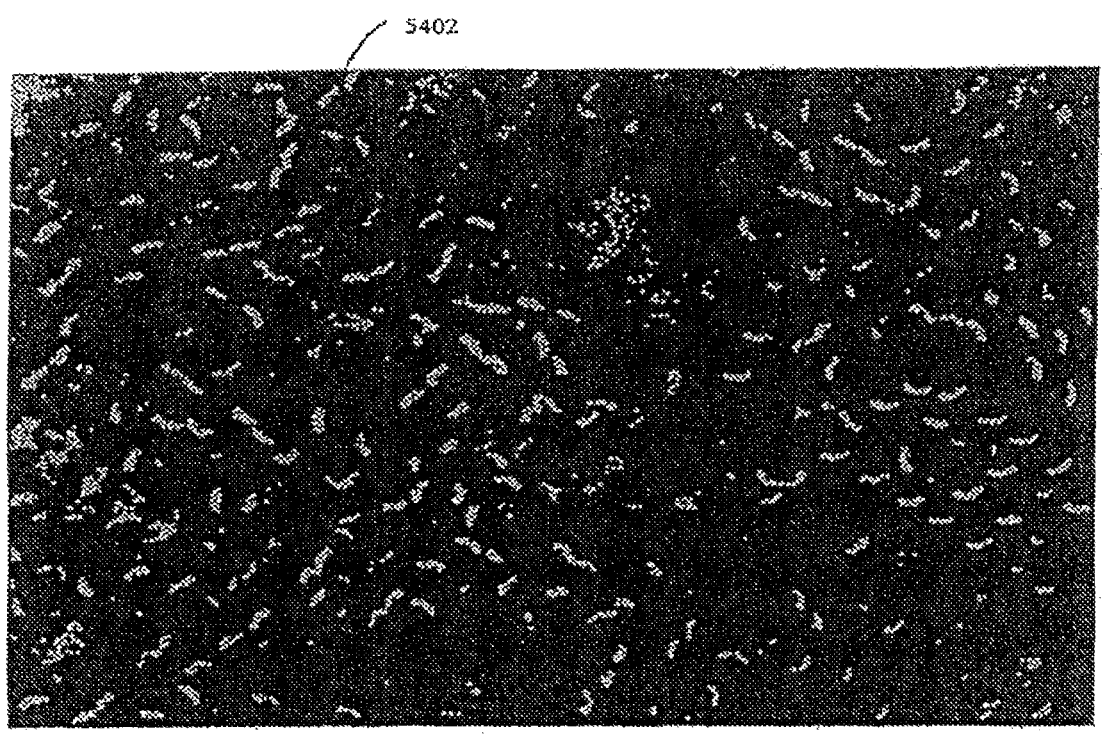
FIG. 57 shows particles formed from methods described herein and released from a mold according to an embodiment of the present invention.

A mold (5104) of size 0.5×3 cm with 3×3×8 micron patterned recesses (5106) was dipped into the vial (5102) with 98% PEG-diacrylate and 2% photo initiator solution. After 30 seconds the mold was withdrawn at a rate of approximately 1 mm per second. The process is schematically shown in FIG. 56. Next, the mold was put into a UV oven, purged with nitrogen for 15 minutes and then cured for 15 minutes. The particles were then harvested on a glass slide using cyanoacrylate adhesive. No scum was detected and monodispersity of the particles was confirmed using optical microscope, as shown in the image of FIG. 57. Furthermore, as evident in FIG. 57, the material contained in the recesses formed a meniscus with the sides of the recesses, as shown by reference number 5402. This meniscus, when cured formed a lens on a portion of the particle.

12.10 Fabrication of Particles by Droplet Moving

Figure 58:
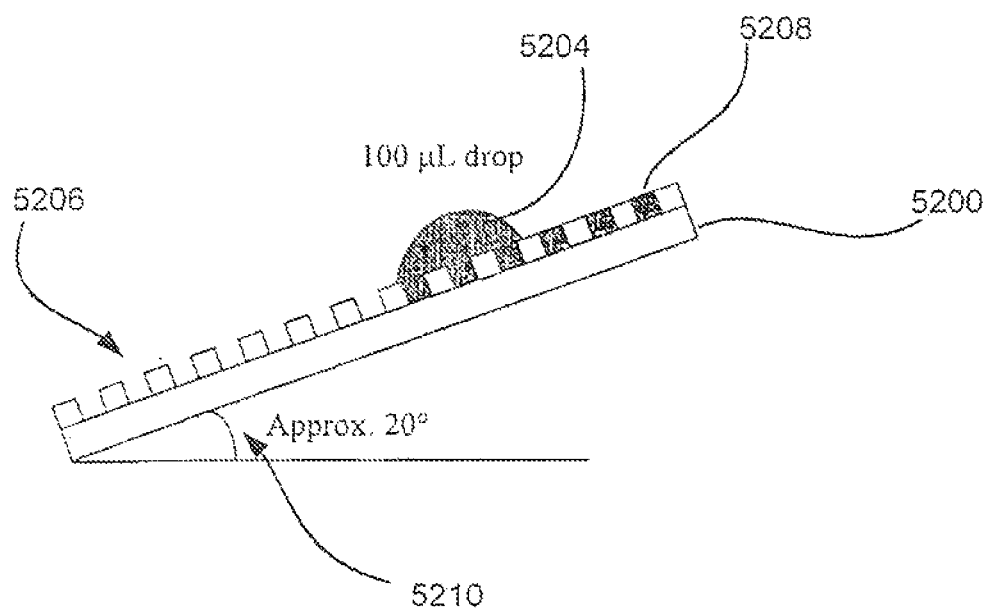
FIG. 58 shows a method of flowing a substance across a patterned template surface to introduce the substance into recesses of the patterned template according to an embodiment of the present invention.

A mold (5200), 6 inch in diameter with 5×5×10 micron pattern recesses (5206) was placed on an incline surface having an angle of 20 degrees (5210) to the horizon. Next, a set of 100 micro liter drops (5204) were placed on the surface of the mold at a higher end. Each drop slid down the mold leaving a trace of filled recesses (5208). The process is schematically shown in FIG. 58.

Figure 59:
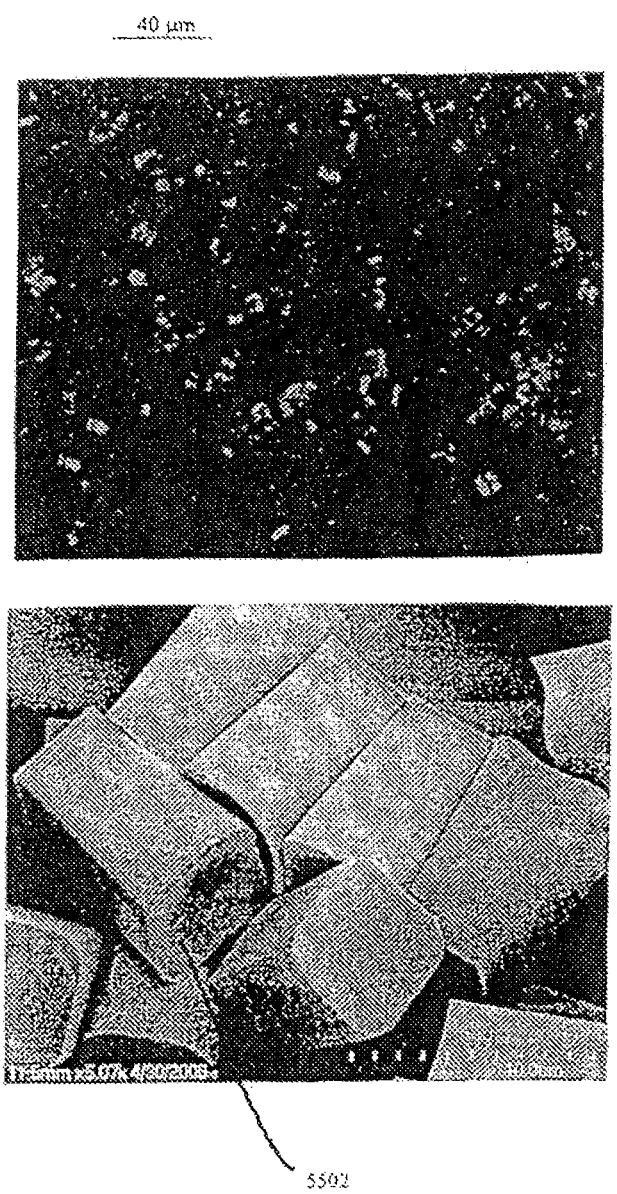
FIG. 59 shows further particles formed from methods described herein and released from a mold according to an embodiment of the present invention.

After all the drops reached the lower end of the mold, the mold was put in a UV oven, purged with nitrogen for 15 minutes and then cured for 15 minutes. The particles were harvested on a glass slide using cyanoacrylate adhesive. No scum was detected and monodispersity of the particles was confirmed first using optical microscope (FIG. 59) and then by scanning electron microscope (FIG. 59). Furthermore, as evident in FIG. 59, the material contained in the recesses formed a meniscus with the sides of the recesses, as shown by reference number 5502. This meniscus, when cured formed a lens on a portion of the particle.

Example 13

Control Mouse Studies

A patterned perfluoropolyether (PFPE) mold is generated by pouring a PFPE-dimethacrylate (PFPE-DMA) containing 2,2'-diethoxy-acetophenone over a silicon substrate patterned with 200 nm shapes. The apparatus is then subjected to UV light ($\lambda$=365 nm) for 15 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 2,2'-diethoxy-acetophenone. 70 µL of PEG diacrylate monomer and 30 uL of CDI-PEG monomer were mixed. Specifically, the CDI-PEG monomer was synthesized by adding 1,1'-carbonyl diimidazole (CDI) to a solution of PEG (n=400) monomethylacrylate in chloroform. This solution was allowed to stir overnight. This solution was then further purified by an extraction with cold water. The resulting CDI-PEG monomethacrylate was then isolated via vacuum. Flat, uniform, non-wetting surfaces are generated by pouring a PFPE-dimethacrylate (PFPE-DMA) containing 2,2'-diethoxy-acetophenone over a silicon wafer and then subjected to UV light ($\lambda$=365 nm) for 15 minutes while under a nitrogen purge. Following this, 50 µL of the PEG diacrylate solution is then placed on the non wetting surface and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for 15 minutes while under a nitrogen purge. Particles are observed after separation of the PFPE mold. The particles were harvested utilizing a sacrificial adhesive layer and verified via DIC microscopy. These particles containing the CDI linker group were subsequently treated with and aqueous solution of fluorescently tagged avidin. These particles were allowed to stir at room temperature for four hours. These particles were then isolated via centrifugation and rinsed with deionized water. These avidin labeled particles were then treated with biotin. A solution (2.5 mg avidin/biotin nanoparticles/200 uL saline) was administered to 4 Neu transgenic mice (2.5 mg avidin/biotin nanoparticles/200 uL saline) every 14 days for 2 cycles (total 28 days) versus a control group 4 Neu transgenic mice that was treated with 200 uL saline every 14 days for 2 cycles (total 28 days). Both sets of mice seemed to produce no adverse side effects from either treatment.

Example 14

Particle Fabrication 14.1 Synthesis of 200 nm Cationic PEG Particles for Pharmacokinetics A patterned perfluoropolyether (PFPE) mold is generated by pouring a PFPE-dimethacrylate (PFPE-DMA) containing 2,2'-diethoxy-acetophenone over a silicon substrate patterned with 200 nm shapes. The apparatus is purged with nitrogen for 10 minutes, and then subjected to UV light Q=365 nm) for 6 minutes while under a nitrogen purge. The fully cured PFPE-DMA mold is then released from the silicon master, and blown with air to remove dust. Separately, a solution containing 84 mol % PEG diacrylate, 5 mol % PEG monoacrylate, 10 mol % aminoethylmethacrylate hydrochloride, and 1 mol % photoinitiator was prepared. The mold was placed in a fume hood and the hydrogel-monomer solution was atomized onto mold. A polyethylene sheet was then placed over the mold and bubbles were removed by manual pressure with a roller. The polyethylene cover was slowly removed to fill the particle chambers. The mold/solution combination was placed into a UV curing chamber, purged for 10 minutes with nitrogen, and UV cured for 0.8 minutes. The particle/mold combination was placed in the spin coater and the spin coater started at approx 1000 rpm. Approx 20 mls of nitro-cellulose was put into the center of the spinning mold and left to cure for 1 minute while rotating. The nitro-cellulose is then carefully lifted off the mold with particles attached and placed in a vial. Acetone is then added to dissolve the cellulose and leave the particles. The particles were purified via centrifugation, and then strained through a 100 mesh screen. The remaining acetone is carefully aspirated and the particles dried under nitrogen.

14.2 Synthesis of 200 nm Triacrylate Particles

Molds suitable for PRINT fabrication of 200×200×200 nm particles were prepared by pooling end-functionalized PFPE dimethacrylate precursor containing 0.1% diethoxyacetophenone (DEAP) photoinitiator onto a master template containing 200×200×200 nm posts. The telechelic PFPE precursor was UV polymerized under a blanket of nitrogen into a cross-linked rubber (the "mold"). The mold was then peeled away from the master, revealing 200×200×200 nm patterned cavities in the mold. 1 part trimethylolpropane triacrylate containing 10% DEAP ("triacrylate resin") was then dissolved in 10 parts methanol and spray-coated onto the patterned side of the mold until full coverage was achieved. A thin polyethylene sheet was placed over the patterned side of the mold and sealed to the mold by manually applying a small amount of pressure. The polyethylene sheet was then slowly peeled away from the mold (~1 mm/sec), allowing capillary filling of the cavities in the mold. Excess triacrylate resin was gathered at the PFPE/polyethylene interface and removed from the mold as the polyethylene sheet was peeled away. Once the polyethylene sheet was fully peeled away from the mold, any residual macroscopic droplets of triacrylate resin were removed from the mold. The triacrylate resin filling the patterned cavities in the mold was then UV polymerized under a blanket of nitrogen for about 5 minutes. Collodion solution (Fisher Scientific) was then spin-cast onto the patterned side of the mold to produce a robust nitrocellulose-based film. This film was then peeled away from the mold to remove particles by adhesive transfer to the nitrocellulose film. The nitrocellulose film was then dissolved in acetone. The particles were purified from the dissolved nitrocellulose by a repetitive process of sedimenting the particles, decanting nitrocellulose/acetone solution, and resuspension of the particles in clean acetone. This process was repeated until all the nitrocellulose was separated from the particles.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A synthetic particle, comprising:
    a substantially disc shaped, molded synthetic polymer particle having largest linear dimension of between about 5 µm to about 10 µm and a modulus of less than about 1 MPa, wherein the particle can pass through an opening of less than about 3 µm.

2. The synthetic particle of claim 1, wherein the synthetic polymer comprises a biocompatible polymer.

3. The synthetic particle of claim 1, wherein the synthetic polymer comprises poly(ethylene glycol), poly(lactic acid), poly(lactide-co-glycolide), poly(ethylene glycol) diacrylate, or trimethylolpropane triacrylate.

4. The synthetic particle of claim 1, wherein the particle further comprises a cargo selected from the group consisting of a therapeutic agent, a biologic, a diagnostic agent, hemoglobin, and an imaging agent.

5. The synthetic particle of claim 4, wherein the cargo is capable of binding and releasing oxygen.

6. The synthetic particle of claim 1, wherein the opening is an orifice, an opening of a tube or a lumen.

7. A drug delivery particle, comprising:
    a substantially disc shaped, molded synthetic polymer particle having a largest linear dimension less than about 10 µm and a modulus of less than about 1 MPa, wherein the particle can pass through an opening less than about 60% the largest linear dimension of the particle.

8. The drug delivery particle of claim 7, wherein the particle can pass through an opening of less than about 37.5% the largest linear dimension of the particle.

9. The drug delivery particle of claim 7, wherein the particle can pass through an opening of less than about 30% the largest linear dimension of the particle.

10. The drug delivery particle of claim 7, wherein the synthetic polymer comprises a biocompatible polymer.

11. The drug delivery particle of claim 7, wherein the synthetic polymer comprises poly(ethylene glycol), poly(lactic acid), poly(lactide-co-glycolide), poly(ethylene glycol) diacrylate, or trimethylolpropane triacrylate.

12. The drug delivery particle of claim 7, wherein the particle further comprises a cargo selected from the group consisting of a therapeutic agent, a biologic, a diagnostic agent, hemoglobin, and an imaging agent.

13. The drug delivery particle of claim 7, wherein the opening is an orifice, an opening of a tube or a lumen.

* * * * *